US012233129B2

(12) United States Patent
Rezvani et al.

(10) Patent No.: US 12,233,129 B2
(45) **Date of Patent: *Feb. 25, 2025**

(54) METHODS AND COMPOSITIONS FOR THE TREATMENT OF CANCER

(71) Applicant: South Dakota Board of Regents, Pierre, SD (US)

(72) Inventors: Khosrow Rezvani, Vermillion, SD (US); Grigoriy Sereda, Vermillion, SD (US)

(73) Assignee: South Dakota Board of Regents, Pierre, SD (US)

( * ) Notice: Subject to any disclaimer, the term of this patent is extended or adjusted under 35 U.S.C. 154(b) by 89 days.

This patent is subject to a terminal disclaimer.

(21) Appl. No.: 18/192,210

(22) Filed: Mar. 29, 2023

(65) Prior Publication Data

US 2023/0414767 A1 Dec. 28, 2023

Related U.S. Application Data

(63) Continuation of application No. 17/035,293, filed on Sep. 28, 2020, now Pat. No. 11,717,573.

(60) Provisional application No. 62/907,569, filed on Sep. 28, 2019.

(51) Int. Cl.
*A61K 47/60* (2017.01)
*A61K 9/51* (2006.01)
*A61K 31/435* (2006.01)
*A61K 47/64* (2017.01)
*A61P 35/00* (2006.01)

(52) U.S. Cl.
CPC ............ *A61K 47/60* (2017.08); *A61K 9/5115* (2013.01); *A61K 9/5161* (2013.01); *A61K 9/5169* (2013.01); *A61K 31/435* (2013.01); *A61K 47/64* (2017.08); *A61K 47/645* (2017.08); *A61P 35/00* (2018.01)

(58) Field of Classification Search
CPC ...... A61K 47/60; A61K 47/645; A61K 47/64; A61K 9/5115; A61K 9/5161; A61K 9/5169; A61K 31/435; A61P 35/00
See application file for complete search history.

(56) References Cited

PUBLICATIONS

Abdullah et al (Year: 2015).*
Buescher et al (Year: 2007).*
Vaidya et al (Year: 2008).*
Luo WI, Dizin E, Yoon T, Cowan JA. Kinetic and structural characterization of human mortalin. Protein Expr Purif. 2010;72:75-81.
Dundas SR, Lawrie LC, Rooney PH, Murray GI. Mortalin is over-expressed by colorectal adenocarcinomas and correlates with poor survival. J Pathol. 2005;205(1):74-81.
Takano S, Wadhwa R, Yoshii Y, Nose T, Kaul SC, Mitsui Y. Elevated levels of mortalin expression in human brain tumors. Exp Cell Res. 1997; 237(1):38-45.
Wadhwa R, Takano S, Kaur K, Deocaris CC, Pereira-Smith OM, Reddel RR, et al. Upregulation of mortalin/mthsp70/Grp75 contributes to human carcinogenesis. Int J Cancer. 2006;118:2973-2980.
Ostermeyer AG, Runko E, Winkfield B, Ahn B, Moll UM. Cytoplasmically sequestered wild-type p53 protein in neuroblastoma is relocated to the nucleus by a C-terminal peptide. Proc Natl Acad Sci USA. 1996;93:15190-15194.
Gestl EE, Anne Bottger S. Cytoplasmic sequestration of the tumor suppressor p53 by a heat shock protein 70 family member, mortalin, in human colorectal adenocarcinoma cell lines. Biochem Biophys Res Commun. 2012;423:411-416.
Lu WJ, Lee NP, Kaul SC, Lan F, Poon RT, Wadhwa R, et al. Mortalin-p53 interaction in cancer cells is stress dependent and constitutes a selective target for cancer therapy. Cell Death Differ. 2011;6:1046-1056.
Wadhwa R, Takano S, Robert M, Yoshida A, Nomura H, Reddel RR, et al. Inactivation of tumor suppressor p53 by mot-2, a hsp70 family member. J Biol Chem. 1998;273(45):29586-29591.
Lu WJ, Lee NP, Kaul SC, Lan F, Poon RT, Wadhwa R, et al. Induction of mutant p53-dependent apoptosis in human hepatocellular carcinoma by targeting stress protein mortalin. Int J Cancer. 2011;129:1806-1814.
Iacopetta B. TP53 mutation in colorectal cancer. Hum Mutat. 2003;21:271-276.
Cheok CF, Verma CS, Baselga J, Lane DP. Translating p53 into the clinic. Nat Rev Clin Oncol. 2011;8:25-37.
Alexandru G, Graumann J, Smith GT, Kolawa NJ, Fang R, Deshaies Rj. UBXD7 binds multiple ubiquitin ligases and implicates p97 in HIF1alpha turnover. Cell. 2008;134:804-816.
Haines DS. p97-containing complexes in proliferation control and cancer: emerging culprits or guilt by association. Genes Cancer. 2010;1:753-763.
Lee JJ, Kim YM, Jeong J, Bae DS, Lee KJ. Ubiquitin-associated (UBA) domain in human Fas associated factor 1 inhibits tumor formation by promoting Hsp70 degradation. PLoS One. 2012; 7(8):e40361.
Rezvani K, Teng Y, Pan Y, Dani JA, Lindstrom J, Garcia Gras EA, et al. UBXD4, a UBX-containing protein, regulates the cell surface number and stability of alpha3-containing nicotinic acetylcholine receptors. J Neurosci. 2009;29:6883-6896.
Shaw P, Bovey R, Tardy S, Sahli R, Sordat B, Costa J. Induction of apoptosis by wild-type p53 in a human colon tumor-derived cell line. Proc Natl Acad Sci USA. 1992;89:4495-4499.

(Continued)

*Primary Examiner* — Jeffrey S Lundgren
*Assistant Examiner* — Ibrahim D Bori
(74) *Attorney, Agent, or Firm* — Fredrikson & Byron, P.A.

(57) ABSTRACT

Disclosed herein are compositions for treating cancer comprising a modified veratridine.
In certain aspects, the modified veratridine comprises a polyglutamic acid (PLE) or polyethylene glycol/polyglutamic acid (PEG-PLE) conjugated to the 4' hemiketal thereof. Further disclosed is a method of treating colorectal cancer in a subject comprising administering to a subject an effective amount of the disclosed compositions.

20 Claims, 32 Drawing Sheets
(25 of 32 Drawing Sheet(s) Filed in Color)

Specification includes a Sequence Listing.

(56) References Cited

PUBLICATIONS

Fang L, Kaake RM, Patel VR, Yang Y, Baldi P, Huang L. Mapping the protein interaction network of the human COP9 signalosome complex using a label-free QTAX strategy. Mol Cell Proteomics. 2012;11:138-147.

Rezvani K, Baalman K, Teng Y, Mee MP, Dawson SP, Wang H, et al. Proteasomal degradation of the metabotropic glutamate receptor 1alpha is mediated by Homer-3 via the proteasomal S8 ATPase: Signal transduction and synaptic transmission. J Neurochem. 2012;122:24-37.

Wadhwa R, Yaguchi T, Hasan MK, Mitsui Y, Reddel RR, Kaul SC. Hsp70 family member, mot-2/mthsp70/GRP75, binds to the cytoplasmic sequestration domain of the p53 protein. Exp Cell Res. 2002;274:246-253.

Grover A, Priyandoko D, Gao R, Shandilya A, Widodo N, Bisaria VS, et al. Withanone binds to mortalin and abrogates mortalin-p53 complex: computational and experimental evidence. Int J Biochem Cell Biol. 2012;44:496-504.

Kaul SC, Aida S, Yaguchi T, Kaur K, Wadhwa R. Activation of wild type p53 function by its mortalin-binding, cytoplasmically localizing carboxyl terminus peptides. J Biol Chem. 2005;280(47):39373-39379.

Wadhwa R, Sugihara T, Yoshida A, Nomura H, Reddel RR, Simpson R, et al. Selective toxicity of MKT-077 to cancer cells is mediated by its binding to the hsp70 family protein mot-2 and reactivation of p53 function. Cancer Res. 2000;60(24):6818-6821.

Deng WG, Kawashima H, Wu G, Jayachandran G, Xu K, Minna JD, et al. Synergistic tumor suppression by coexpression of FUS1 and p53 is associated with down-regulation of murine double minute-2 and activation of the apoptotic protease-activating factor 1-dependent apoptotic pathway in human non-small cell lung cancer cells. Cancer Res. 2007;67:709-717.

El-Deiry WS. Regulation of p53 downstream genes. Semin Cancer Biol. 1998;8:345-357.

Yang SY, Sales KM, Fuller BJ, Seifalian AM, Winslet MC. Inducing apoptosis of human colon cancer cells by an IGF-I D domain analogue peptide. Mol Cancer. 2008;7:17.

Ishii T, Fujishiro M, Masuda M, Okudela K, Kitamura H, Teramoto S, et al. Nutritional deficiency affects cell cycle status and viability in A549 cells: role of p27Kip1. Cancer Lett. 2004;213:99-109.

Schuler M, Green DR. Mechanisms of p53-dependent apoptosis. Biochem Soc Trans. 2001;29, Pt 6:684-688.

Kim WH, Yeo M, Kim MS, Chun SB, Shin EC, Park JH, et al. Role of caspase-3 in apoptosis of colon cancer cells induced by nonsteroidal anti-inflammatory drugs. Int J Colorectal Dis. 2000;15:105-111.

Burbulla LF, Schelling C, Kato H, Rapaport D, Woitalla D, Schiesling C, et al. Dissecting the role of the mitochondrial chaperone mortalin in Parkinson's disease: functional impact of disease-related variants on mitochondrial homeostasis. Hum Mol Genet. 2010; 19(22):4437-4452.

Schwitalla S, Ziegler PK, Horst D, Becker V, Kerle I, Begus-Nahrmann Y, et al. Loss of p53 in enterocytes generates an inflammatory microenvironment enabling invasion and lymph node metastasis of carcinogen-induced colorectal tumors. Cancer Cell. 2013;23:93-106.

Hwang CI, Matoso A, Corney DC, Flesken-Nikitin A, Korner S, Wang W, et al. Wild-type p53 controls cell motility and invasion by dual regulation of MET expression. Proc Natl Acad Sci USA. 2011; 108:14240-14245.

Iosefson O, Azem A. Reconstitution of the mitochondrial Hsp70 (mortalin)-p53 interaction using purified proteins-identification of additional interacting regions. FEBS Lett. 2010;584:1080-1084.

Utomo DH, Widodo N, Rifa'i M. Identifications small molecules inhibitor of p53-mortalin complex for cancer drug using virtual screening. Bioinformation. 2012;8:426-429.

Kaul SC, Reddel RR, Mitsui Y, Wadhwa R. An N-terminal region of mot-2 binds to p53 in vitro. Neoplasia. 2001;3:110-114.

Ando K, Oki E, Zhao Y, Ikawa-Yoshida A, Kitao H, Saeki H, et al. Mortalin is a prognostic factor of gastric cancer with normal p53 function. Gastric Cancer 2013. 3Print ISSN1436-3291.3291.

Luk JM, Lam CT, Siu AF, Lam BY, Ng IO, Hu MY, et al. Proteomic profiling of hepatocellular carcinoma in Chinese cohort reveals heat-shock proteins (Hsp27, Hsp70, GRP78) up-regulation and their associated prognostic values. Proteomics. 2006;6:1049-1057.

Lopergolo A, Pennati M, Gandellini P, Orlotti NI, Poma P, Daidone MG, et al. Apollon gene silencing induces apoptosis in breast cancer cells through p53 stabilisation and caspase-3 activation. Br J Cancer. 2009;100:739-746.

Pines A, Kelstrup CD, Vrouwe MG, Puigvert JC, Typas D, Misovic B, et al. Global phosphoproteome profiling reveals unanticipated networks responsive to cisplatin treatment of embryonic stem cells. Mol Cell Biol. 2011;31:4964-4977.

Zhou X, Hao Q, Liao J, Zhang Q, Lu H. Ribosomal protein S14 unties the MDM2-p53 loop upon ribosomal stress. Oncogene. 2013;32:388-396.

Vakifahmetoglu H, Olsson M, Orrenius S, Zhivotovsky B. Functional connection between p53 and caspase-2 is essential for apoptosis induced by DNA damage. Oncogene. 2006;25:5683-5692.

Noble P, Vyas M, Al-Attar A, Durrant S, Scholefield J, Durrant L. High levels of cleaved caspase-3 in colorectal tumour stroma predict good survival. Br J Cancer. 2013;108:2097-2105.

Kaul SC, Duncan EL, Englezou A, Takano S, Reddel RR, Mitsui Y, et al. Malignant transformation of NIH3T3 cells by overexpression of mot-2 protein. Oncogene. 1998;17:907-911.

Kaul SC, Reddelb RR, Sugiharac T, Mitsuia Y, Wadhwac R. Inactivation of p53 and life span extension of human diploid fibroblasts by mot-2. FEBS Lett. 2000;474:159-164.

Wadhwa R, Takano S, Kaur K, Aida S, Yaguchi T, Kaul Z, et al. Identification and characterization of molecular interactions between mortalin/mtHsp70 and HSP60. Biochem J. 2005;391, Pt 2:185-190.

Wadhwa R, Taira K, Kaul SC. An Hsp70 family chaperone, mortalin/mthsp70/PBP74/Grp75: what, when, and where. Cell Stress Chaperones. 2002;7:309-316.

Vassilev LT, Vu BT, Graves B, Carvajal D, Podlaski F, Filipovic Z, et al. In vivo activation of the p53 pathway by small-molecule antagonists of MDM2. Science. 2004;303:844-848.

Villalonga-Planells R, Coll-Mulet L, Martinez-Soler F, Castano E, Acebes JJ, Gimenez-Bonafe P, et al. Activation of p53 by nutlin-3a induces apoptosis and cellular senescence in human glioblastoma multiforme. PLoS One. 2011;6:e18588.

Zuckerman V, Lenos K, Popowicz GM, Silberman I, Grossman T, Marine JC, et al. c-Abl phosphorylates Hdmx and regulates its interaction with p53. J Biol Chem. 2009;284:4031-4039.

Chan AL, Grossman T, Zuckerman V, Campigli Di Giammartino D, Moshel O, Scheffner M, et al. c-Abl phosphorylates E6AP and regulates its E3 ubiquitin ligase activity. Biochemistry. 2013;52:3119-3129.

Buescher et al., "Microbial Biosynthesis of Polyglutamic Acid Biopolymer and Applications in the Biopharmaceutical, Biomedical and Food Industries," Critical Reviews in Biotechnology, vol. 27, No. 1, 2007, pp. 1-19.

Su CH, Zhao R, Zhang F, Qu C, Chen B, Feng YH, et al. 14-3-3sigma exerts tumor-suppressor activity mediated by regulation of COP1 stability. Cancer Res. 2011;71:884-894.

Zhang Y, Xiong Y, Yarbrough WG. ARF promotes MDM2 degradation and stabilizes p53: ARF-INK4a locus deletion impairs both the Rb and p53 tumor suppression pathways. Cell. 1998;92:725-734.

Zhang Y, Wang J, Yuan Y, Zhang W, Guan W, Wu Z, et al. Negative regulation of HDM2 to attenuate p53 degradation by ribosomal protein L26. Nucleic Acids Res. 2010;38:6544-6554.

Huang Q, Raya A, DeJesus P, Chao SH, Quon KC, Caldwell JS, et al. Identification of p53 regulators by genome-wide functional analysis. Proc Natl Acad Sci USA. 2004; 101:3456-3461.

Halaby MJ, Hakem A, Li L, El Ghamrasni S, Venkatesan S, Hande PM, et al. Synergistic interaction of Rnf8 and p53 in the protection against genomic instability and tumorigenesis. PLoS Genet. 2013;9:e1003259.

Toiyama Y, Inoue Y, Yasuda H, Saigusa S, Yokoe T, Okugawa Y, et al. DPEP1, expressed in the early stages of colon carcinogenesis, affects cancer cell invasiveness. J Gastroenterol. 2011;46:153-163.

(56) References Cited

PUBLICATIONS

Kudo T, Ikeda M, Nishikawa M, Yang Z, Ohno K, Nakagawa K, et al. The RASSF3 candidate tumor suppressor induces apoptosis and G1-S cell-cycle arrest via p53. Cancer Res. 2012;72:2901-2911.

Hsu TI, Wang MC, Chen SY, Yeh YM, Su WC, Chang WC, et al. Sp1 expression regulates lung tumor progression. Oncogene. 2012;31:3973-3988.

Goyeneche AA, Caron RW, Telleria CM. Mifepristone inhibits ovarian cancer cell growth in vitro and in vivo. Clin Cancer Res. 2007;13:3370-3379.

Sane S, Abdullah A, Boudreau DA, Autenried RK, Gupta BK, Wang X, Wang H, Schlenker EH, Zhang D, Telleria C, Huang L, Chauhan SC and Rezvani K. Ubiquitin-like (UBX)-domain-containing protein, UBXN2A, promotes cell death by interfering with the p53-Mortalin interactions in colon cancer cells. Cell Death Dis. 2014; 5:e1118.

Koya K, Li Y, Wang H, Ukai T, Tatsuta N, Kawakami M, Shishido and Chen LB. MKT-077, a novel rhodacyanine dye in clinical trials, exhibits anticarcinoma activity in preclinical studies based on selective mitochondrial accumulation. Cancer Res. 1996; 56(3):538-543.

Chen J, Liu WB, Jia WD, Xu GL, Ma JL, Huang M, Deng YR and Li JS. Overexpression of Mortalin in hepatocellular carcinoma and its relationship with angiogenesis and epithelial to mesenchymal transition. Int J Oncol. 2014; 44(1):247-255.

Boyle P and Leon ME. Epidemiology of colorectal cancer. Br Med Bull. 2002; 64:1-25.

Phan VT, Ding VW, Li F, Chalkley RJ, Burlingame A and McCormick F. The RasGAP proteins Ira2 and neurofibromin are negatively regulated by Gpb1 in yeast and ETEA in humans. Mol Cell Biol. 2010; 30(9):2264-2279.

Wu-Baer F, Ludwig T and Baer R. The UBXN1 protein associates with autoubiquitinated forms of the BRCA1 tumor suppressor and inhibits its enzymatic function. Mol Cell Biol. 2010; 11:2787-2798.

Wu PK, Hong SK, Veeranki S, Karkhanis M, Starenki D, Plaza JA and Park Ji. A mortalin/HSPA9-mediated switch in tumor-suppressive signaling of Raf/MEK/extracellular signal-regulated kinase. Mol Cell Biol. 2013; 33(20):4051-4067.

Zhang J, Wang C, Ke N, Bliesath J, Chionis J, He QS, Li QX, Chatterton JE, Wong-Staal F and Zhou D. A more efficient RNAi inducible system for tight regulation of gene expression in mammalian cells and xenograft animals. RNA. 2007; 13(8):1375-1383.

Hensley H, Devarajan K, Johnson JR, Piwnica-Worms D, Godwin AK, von Mehren M and Rink L. Evaluating new therapies in gastrointestinal stromal tumor using in vivo molecular optical imaging. Cancer Biol Ther. 2014; 15(7):911-918.

Bourin M, Chenu F and Hascoet M. Topiramate and phenytoin anti-immobility effect in the mice forced swimming test is reversed by veratrine: Implication for bipolar depression treatment. Behav Brain Res. 2009; 205(2):421-425.

Benforado JM. (1967). Physiological pharmacology, The veratrum alkaloids: pp. 331-386.

Hare JD. Purification and Quantitative Analysis of Veratridine and Cevadine by HPLC. Journal of Agricultural and Food Chemistry 1996; 44(1):149-152.

Loizzo MR, Tundis R, Menichini F and Statti GA. Hypotensive natural products: current status. Mini Rev Med Chem. 2008; 8(8):828-855.

Fraser SP, Grimes JA and Djamgoz MB. Effects of voltage-gated ion channel modulators on rat prostatic cancer cell proliferation: comparison of strongly and weakly metastatic cell lines. Prostate. 2000; 44(1):61-76.

Fraser SP, Salvador V, Manning EA, Mizal J, Altun S, Raza M, Berridge RJ and Djamgoz MB. Contribution of functional voltage-gated Na+ channel expression to cell behaviors involved in the metastatic cascade in rat prostate cancer: I. Lateral motility. J Cell Physiol. 2003; 195(3):479-487.

Jordan J, Galindo MF, Calvo S, Gonzalez-Garcia C and Cena V. Veratridine induces apoptotic death in bovine chromaffin cells through superoxide production. Br J Pharmacol. 2000; 130(7):1496-1504.

Jordan J, Galindo MF, Tornero D, Benavides A, Gonzalez C, Agapito MT, Gonzalez-Garcia C and Cena V. Superoxide anions mediate veratridine-induced cytochrome c release and caspase activity in bovine chromaffin cells. Br J Pharmacol. 2002; 137(7):993-1000.

Gomez-Lazaro M, Galindo MF, Fernandez-Gomez FJ, Prehn JH and Jordan J. Activation of p53 and the pro-apoptotic p53 target gene PUMA during depolarization- induced apoptosis of chromaffin cells. Exp Neurol. 2005; 196(1):96-103.

Sui X, Kong N, Wang X, Fang Y, Hu X, Xu Y, Chen W, Wang K, Li D, Jin W, Lou F, Zheng Y, Hu H, Gong L, Zhou X, Pan H, et al. JNK confers 5-fluorouracil resistance in p53-deficient and mutant p53-expressing colon cancer cells by inducing survival autophagy. Sci Rep. 2014; 4:4694.

Kaul Z, Yaguchi T, Kaul SC, Hirano T, Wadhwa R and Taira K. Mortalin imaging in normal and cancer cells with quantum dot immuno-conjugates. Cell Res. 2003; 13(6):503-507.

Widodo N, Deocaris CC, Kaur K, Hasan K, Yaguchi T, Yamasaki K, Sugihara T, Ishii T, Wadhwa R and Kaul SC. Stress chaperones, mortalin, and pex19p mediate 5-aza-2' deoxycytidine-induced senescence of cancer cells by DNA methylation-independent pathway. J Gerontol A Biol Sci Med Sci. 2007; 62(3):246-255.

Green DR and Kroemer G. Cytoplasmic functions of the tumour suppressor p53. Nature. 2009; 458(7242):1127-1130.

Lowe SW, Cepero E and Evan G. Intrinsic tumour suppression. Nature. 2004; 432(7015):307-315.

Gajate C, An F and Mollinedo F. Differential cytostatic and apoptotic effects of ecteinascidin-743 in cancer cells. Transcription-dependent cell cycle arrest and transcription-independent JNK and mitochondrial mediated apoptosis. J Biol Chem. 2002; 277(44):41580-41589.

Deeb KK, Trump DL and Johnson CS. Vitamin D signalling pathways in cancer: potential for anticancer therapeutics. Nat Rev Cancer. 2007; 7(9):684-700.

Yang MH, Kim J, Khan IA, Walker LA and Khan SI. Nonsteroidal anti-inflammatory drug activated gene-1 (NAG-1) modulators from natural products as anti-cancer agents. Life Sci. 2014; 100(2):75-84.

Chan JY, Phoo MS, Clement MV, Pervaiz S and Lee SC. Resveratrol displays converse dose-related effects on 5-fluorouracil-evoked colon cancer cell apoptosis: the roles of caspase-6 and p53. Cancer Biol Ther. 2008; 7 (8):1305-1312.

Kozovska Z, Gabrisova V and Kucerova L. Colon cancer: cancer stem cells markers, drug resistance and treatment. Biomed Pharmacother. 2014; 68(8):911-916.

Violette S, Poulain L, Dussaulx E, Pepin D, Faussat AM, Chambaz J, Lacorte JM, Staedel C and Lesuffleur T. Resistance of colon cancer cells to long-term 5-fluorouracil exposure is correlated to the relative level of Bcl-2 and Bcl-X(L) in addition to Bax and p53 status. Int J Cancer. 2002; 98(4):498-504.

Schmoll HJ, Buchele T, Grothey A and Dempke W. Where do we stand with 5-fluorouracil? Semin Oncol. 1999; 26(6):589-605.

Rao GH, Liu HM, Li BW, Hao JJ, Yang YL, Wang MR, Wang XH, Wang J, Jin HJ, Du L and Chen Q. Establishment of a human colorectal cancer cell line P6C with stem cell properties and resistance to chemotherapeutic drugs. Acta Pharmacol Sin. 2013; 34(6):793-804.

Kurashina K, Yamashita Y, Ueno T, Koinuma K, Ohashi J, Horie H, Miyakura Y, Hamada T, Haruta H, Hatanaka H, Soda M, Choi YL, Takada S, Yasuda Y, Nagai H and Mano H. Chromosome copy number analysis in screening for prognosis-related genomic regions in colorectal carcinoma. Cancer Sci. 2008; 99(9):1835-1840.

Shao RG, Cao CX, Nieves-Neira W, Dimanche-Boitrel MT, Solary E and Pommier Y. Activation of the Fas pathway independently of Fas ligand during apoptosis induced by camptothecin in p53 mutant human colon carcinoma cells. Oncogene. 2001; 20(15):1852-1859.

Upreti M, Lyle CS, Skaug B, Du L and Chambers TC. Vinblastine-induced apoptosis is mediated by discrete alterations in subcellular location, oligomeric structure, and activation status of specific Bcl-2 family members. J Biol Chem. 2006; 281(23):15941-15950.

(56) References Cited

PUBLICATIONS

Urra FA, Cordova-Delgado M, Pessoa-Mahana H, Ramirez-Rodriguez O, Weiss-Lopez B, Ferreira J and Araya-Maturana R. Mitochondria: a promising target for anticancer alkaloids. Curr Top Med Chem. 2013; 13(17):2171-2183.

Yang L, Guo W, Zhang Q, Li H, Liu X, Yang Y, Zuo J and Liu W. Crosstalk between Raf/MEK/ERK and PI3K/AKT in suppression of Bax conformational change by Grp75 under glucose deprivation conditions. J Mol Biol. 2011; 414(5):654-666.

Guo W, Yan L, Yang L, Liu X, E Q, Gao P, Ye X, Liu W and Zuo J. Targeting GRP75 improves HSP90 inhibitor efficacy by enhancing p53-mediated apoptosis in hepatocellular carcinoma. PLoS One. 2014; 9(1):e85766.

Saar Ray M, Moskovich O, Josefson O and Fishelson Z. Mortalin/Grp75 Binds to Complement C9 and Plays a Role in Resistance to Complement-Dependent Cytotoxicity. J Biol Chem. 2014; 289(21):15014-15022.

Ryu J, Kaul Z, Yoon AR, Liu Y, Yaguchi T, Na Y, Ahn HM, Gao R, Choi IK, Yun CO, Kaul SC and Wadhwa R. Identification and functional characterization of nuclear mortalin in human carcinogenesis. J Biol Chem. 2014; 289 (36):24832-24844.

Yoo JY, Ryu J, Gao R, Yaguchi T, Kaul SC, Wadhwa R and Yun CO. Tumor suppression by apoptotic and anti-angiogenic effects of mortalin-targeting adeno-oncolytic virus. J Gene Med. 2010; 12(7):586-595.

Wang Z and Sun Y. Targeting p53 for Novel Anticancer Therapy. Transl Oncol. 2010; 3(1):1-12.

Vidal SJ, Rodriguez-Bravo V, Galsky M, Cordon-Cardo C and Domingo-Domenech J. Targeting cancer stem cells to suppress acquired chemotherapy resistance. Oncogene. 2014; 33(36):4451-4463.

Hermann PC, Huber SL, Herrler T, Aicher A, Ellwart JW, Guba M, Bruns CJ and Heeschen C. Distinct populations of cancer stem cells determine tumor growth and metastatic activity in human pancreatic cancer. Cell Stem Cell. 2007; 1(3):313-323.

Witney TH, Kettunen MI, Hu DE, Gallagher FA, Bohndiek SE, Napolitano R and Brindle KM. Detecting treatment response in a model of human breast adenocarcinoma using hyperpolarised [1-13C]pyruvate and [1,4-13C2]fumarate. Br J Cancer. 2010; 103(9):1400-1406.

Maaser C, Schoeppner S, Kucharzik T, Kraft M, Schoenherr E, Domschke W and Luegering N. Colonic epithelial cells induce endothelial cell expression of ICAM-1 and VCAM-1 by a NF-kappaB-dependent mechanism. Clin Exp Immunol. 2001; 124(2):208-213.

Bijnsdorp IV, Giovannetti E and Peters GJ. Analysis of drug interactions. Methods Mol Biol. 2011; 731:421-434.

Vaidya et al., "Contrast-Enhanced MRI-Guided Photdynamic Cancer Therapy with a Pegylated Bifunctional Polymer Conjugate," Pharmaceutical Research, vol. 25, No. 9, Sep. 2008, pp. 2002-2011.

Abdullah et al., "A plant alkaloid, veratridine, potentiates cancer chemosensitivity by UBXN2A-dependent inhibition of an oncoprotein, mortalin-2," Oncotarget, vol. 6, No. 27, pp. 23561-23581.

Jonker et al., "Cetuximab for the Treatment of Colorectal Cancer," The New England Journal of Medicine, vol. 357, No. 20, Nov. 15, 2007, pp. 2040-2048.

\* cited by examiner

Supplement Figure 4-Sane et al.

A.

B.

C.

Input: 25% of total (Lane I)
IP: Lane II = IgG
IP: Lane III = Anti-UBXN2A.
IB: Anti-mot-2 and anti-UBXN2A antibodies

D.

Input: 25% of total (Lane III)
IP: Lane I = IgG
IP: Lane II = Anti-UBXN2A.
IB: Anti-mot-2 and anti-UBXN2A antibodies Supplement Figure 5-Sane et al.

Poly(ethylene glycol)-*block*-Poly(glutamic acid)-*graft*-Veratridine
PEG-PLE-VT (Water soluble, >1mg/ml)

SEQUENCE LISTING

```
Sequence total quantity: 4
SEQ ID NO: 1            moltype = DNA  length = 24
FEATURE                 Location/Qualifiers
source                  1..24
                        mol_type = genomic DNA
                        organism = Homo sapiens
SEQUENCE: 1
tgaggaagct cagaaggtta gttc                                           24

SEQ ID NO: 2            moltype = DNA  length = 22
FEATURE                 Location/Qualifiers
source                  1..22
                        mol_type = genomic DNA
                        organism = Homo sapiens
SEQUENCE: 2
gttgttcagt ggaacagcag ac                                             22
```

```
SEQ ID NO: 3              moltype = DNA  length = 22
FEATURE                   Location/Qualifiers
source                    1..22
                          mol_type = genomic DNA
                          organism = Homo sapiens
SEQUENCE: 3
caactacatg gtttacatgt tc                                              22

SEQ ID NO: 4              moltype = DNA  length = 18
FEATURE                   Location/Qualifiers
source                    1..18
                          mol_type = genomic DNA
                          organism = Homo sapiens
SEQUENCE: 4
gccagtggac tccacgac                                                   18
```

METHODS AND COMPOSITIONS FOR THE TREATMENT OF CANCER

CROSS-REFERENCE TO RELATED APPLICATION(S)

This application is a continuation of U.S. application Ser. No. 17/035,293, filed Sep. 28, 2020, and entitled "METHODS AND COMPOSITIONS FOR THE TREATMENT OF CANCER," which claims the benefit under 35 U.S.C. § 119(e) to U.S. Provisional Application 62/907,569, filed Sep. 28, 2019, and entitled "PROCESS WITH INTEGRATED RECYCLE FOR METHODS AND COMPOSITIONS FOR THE TREATMENT OF CANCER," which are incorporated herein by reference in their entirety for all purposes.

GOVERNMENT SUPPORT

This invention was made with government support under U54 GM128729 awarded by the National Institutes of Health. The Government has certain rights in the invention.

SEQUENCE LISTING XML

The instant application contains a sequence listing, which has been submitted in XML file format by electronic submission and is hereby incorporated by reference in its entirety. The XML file, created on Jul. 5, 2023, is named "858163USC1_Sequence_Listing.xml" and is 4,616 bytes in size.

FIELD OF THE INVENTION

Disclosed herein are methods and compositions for treating cancer, particularly colorectal cancer.

BACKGROUND OF THE INVENTION

Despite current treatment regimens, one third of patients with colorectal cancer (CRC) ultimately die from metastatic (disseminated) disease. The five-year survival rate for patients diagnosed with a primary cancer site while that cancer is still in its earliest stage is 91%; however, the survival rate for patients with metastatic disease reduces dramatically, to less than 12%. CRC is responsible for more than 50,000 deaths in the United States annually. There is an unmet need for patients with the metastatic form of colorectal cancer. Veratridine (VTD) is a non-steroidal alkaloid purified from Veratrum alkaloids found in liliaceous plants that has been shown to have power anti-cancer properties. Veratridine and its structurally similar compounds have been used for several therapeutic purposes; it has been prescribed as an emetic drug and for neuralgia. Additionally, VTD functions as an antihypertensive molecule in patients that suffer from high hypertension, and it has been used as an alternative treatment strategy for myasthenia gravis. However, VTD can induce intolerable side effects, such as nausea, vomiting, and profound hypotension, which led to a sharp decrease in its use. Furthermore, animal models indicate VTD, or its metabolites, may be neurotoxic at certain doses. Accordingly, there is a need in for a VTD with reduced toxicity that can be targeted in a tumor specific manner.

BRIEF SUMMARY OF THE INVENTION

Disclosed herein is a composition for treating cancer (e.g. colorectal cancer), comprising a compound having the structure:

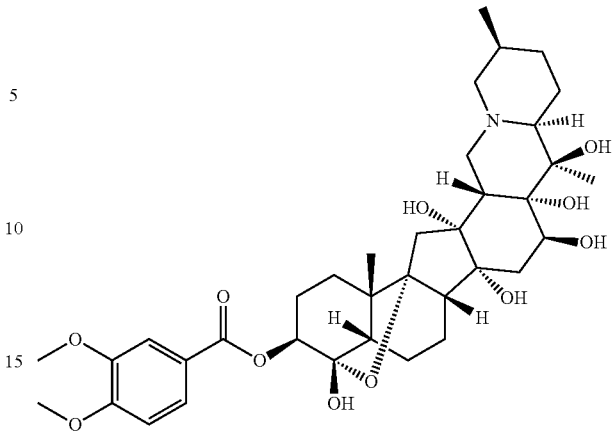

and a modification moiety of polyglutamic acid (PLE) or polyethylene glycol/polyglutamic acid (PEG-PLE) conjugated to the 4' hemiketal thereof. In certain aspect, the modification moiety is PLE. In further aspects, the modification moiety is PEG-PLE.

According to certain embodiments, the composition further comprises a pharmaceutically acceptable carrier. In certain aspects, the pharmaceutically acceptable carrier is a nanoparticle. In further aspects, the nanoparticle carrier is mesoporous silica nanoparticle. In yet further aspects, the mesoporous silica nanoparticle further comprises at least one hyaluronic acid, conjugated thereto.

Further disclosed herein is as method of treating colorectal cancer in a subject, comprising administering to the subject an effective amount of a composition disclosed herein. According to certain embodiments, the subject suffers from metastatic colorectal cancer. According to further embodiments, the composition selectively binds colorectal cancer cells. In further aspects, the disclosed composition selectively binds colorectal cancer cells via hyaluronic acid conjugated to the composition. In yet further aspects, the composition has reduced neurotoxicity relative to a comparable dose of unmodified VTD.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Figure 1:
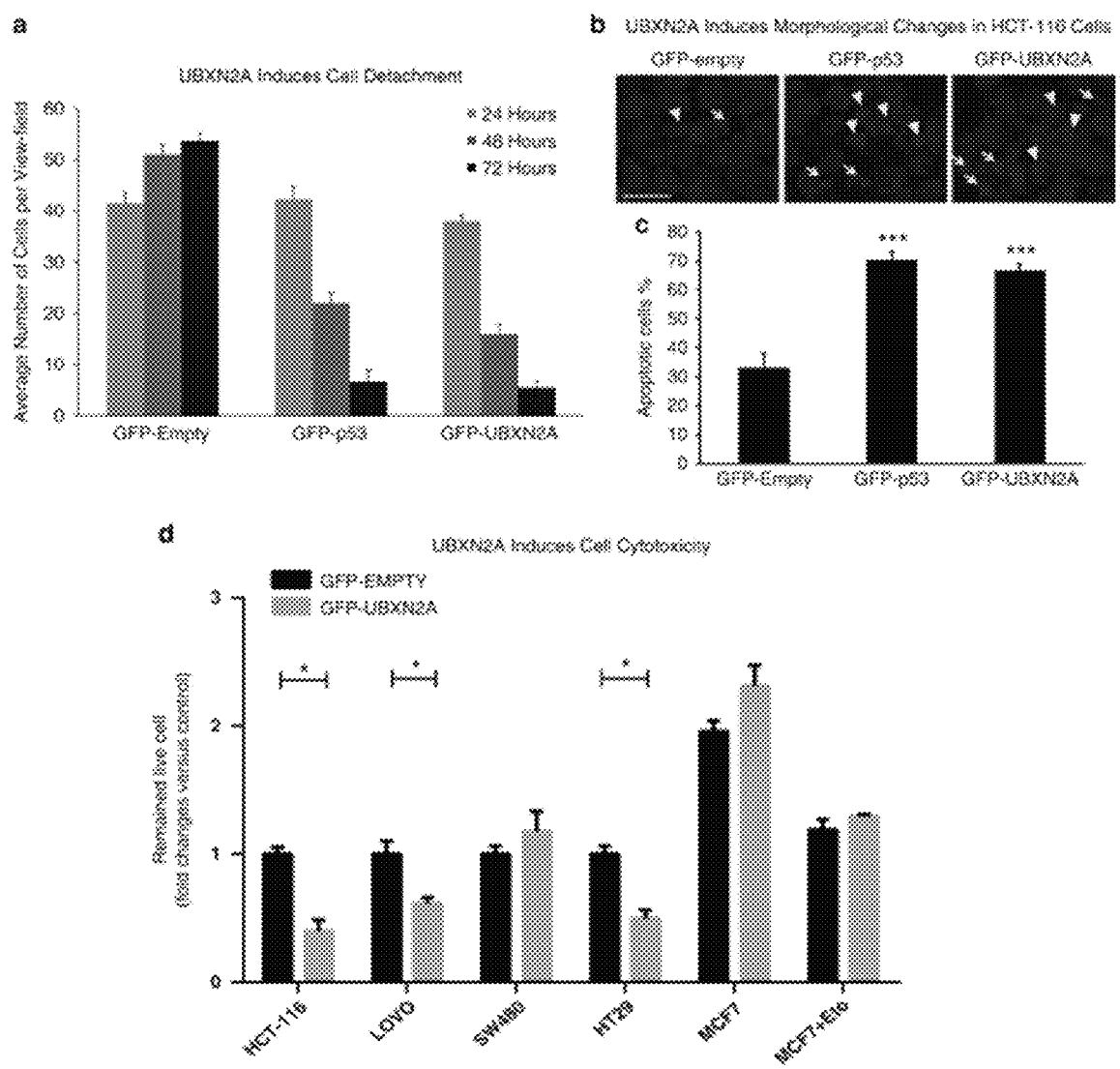
FIG. 1 shows Cytotoxicity of UBXN2A in colon cancer cells with WT-p53.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "UBXN2A enhancer" means any substance, compound, composition, or agent that elevates or increases the expression and/or activity of UBXN2A.

As used herein "veratridine" the steroid-derived alkaloid from plants in the Liliaceae family having the structure:

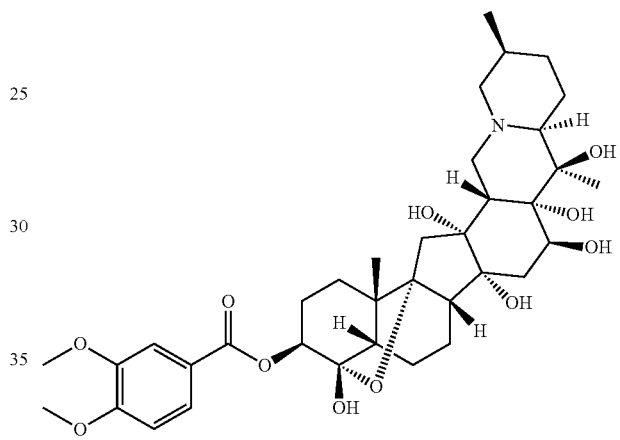

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, The term "cancer" refers to cells having the capacity for autonomous growth. Examples of such cells include cells having an abnormal state or condition characterized by rapidly proliferating cell growth. The term is meant to include cancerous growths, e.g., tumors; oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as most colon cancers, renal-cell carcinoma, prostate cancer and/or testicular tumors, non-small cell carcinoma of the lung, cancer of the small intestine, and cancer of the esophagus. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knockout of a tumor suppressor gene, and cancer caused by infections, e.g., viral infections. The term "carcinoma" is art recognized and refers to malignancies of epithelial or endocrine tissues. In some embodiments, the present methods can be used to treat a subject having an epithelial cancer, e.g., a solid tumor of epithelial origin, e.g., lung, breast, ovarian, prostate, renal, pancreatic, or colon cancer.

As used herein, the term "subject" refers to the target of administration, e.g., an animal. Thus the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more cancer disorders prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with cancer" means having been subjected to a physical examination by a person of skill, for example, a physician, and found to have a condition that can be diagnosed or treated by a compound or composition that can reduce tumor size or slow rate of tumor growth. A subject having cancer, tumor, or at least one cancer or tumor cell, may be identified using methods known in the art. For example, the anatomical position, gross size, and/or cellular composition of cancer cells or a tumor may be determined using contrast-enhanced MRI or CT. Additional methods for identifying cancer cells can include, but are not limited to, ultrasound, bone scan, surgical biopsy, and biological markers (e.g., serum protein levels and gene expression profiles). An imaging solution comprising a cell-sensitizing composition of the present invention may be used in combination with MRI or CT, for example, to identify cancer cells.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

The phrase "anti-proliferative agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agents available in commercial use, in clinical evaluation and in pre-clinical development, which could be included in this application by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

In an aspect, disclosed is a method for treating cancer in a subject comprising administering to the subject an effective amount of a composition comprising a UBXN2A enhancer and a pharmaceutically acceptable carrier thereof. In an aspect, the UBXN2A enhancer is veratridine. In a further aspect, the UBXN2A enhancer is a veratridine derivative. In a yet further aspect, the UBXN2A enhancer increases expression levels of UBXN2A.

Disclosed herein is a composition for treating cancer, comprising a compound having the structure:

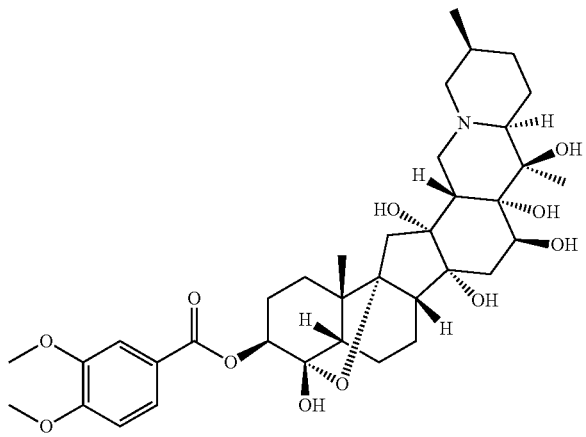

wherein polyglutamic acid (PLE) or polyethylene glycol/polyglutamic acid (PEG-PLE) is conjugated to the 4' hemiketal thereof. According to certain implementations, the modification has the structure:

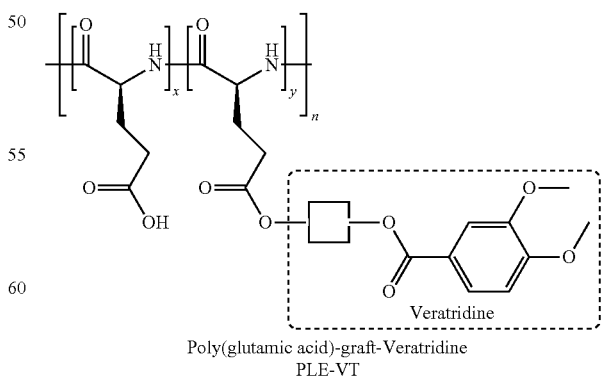

Poly(glutamic acid)-graft-Veratridine
PLE-VT

According to further implementations, the modification has the structure:

Poly(ethylene glycol)-block-Poly(glutamic acid)-graft-Veratridine
PEG-PLE-VT

In certain aspects, the PLE or PEG-PLE modification of veratridine is monomeric. According to certain alternative embodiments, PLE or PEG-PLE modification of veratridine are polymeric.

Without wishing to be bound to any particular theory, it is believed that the metabolism of VTD in the liver generates two 0-demethyl-veratridine catechol structures. These structures are likely responsible for the neurotoxicity of VTD. The inventors have found that the modifications of VTD disclosed herein interrupt formation of highly electrophilic ortho-quinones in catechol metabolites. In certain embodiments, these two modified VTD molecule carry a poly glutamic acid (PLE) or poly ethylene glycol/poly glutamic acid (PEG-PLE). These modifications provide at least the following advantages: 1) an alternative therapeutic approach in metastatic forms of CRC; 2) VTD can be a protective compound in high risk populations for CRC such as obese subjects; and 3) VTD's delivery to tumor tissue will be colon specific using nanoparticle-based delivery, disclosed herein.

According to the further embodiments, the composition further comprises a pharmaceutically acceptable carrier. In certain implementations of these embodiments, the pharmaceutically acceptable carrier is a nanoparticle, including but not limited to, a mesoporous silica nanoparticle. In certain aspect, the disclosed mesoporous silica nanoparticle prevents the disclosed composition from crossing the blood brain barrier, thus reducing likelihood of neurotoxicity. Loading of the disclosed compositions into the mesoporous silica nanoparticles may be performed according to the methods described in Coll, C., et al. Enzyme-mediated controlled release systems by anchoring peptide sequences on mesoporous silica supports. ANGEW CHEM INT ED ENGL 50, 2138-2140 (2011, which is incorporated herein by reference in its entirety.

In exemplary implementations, the nanoparticle carrier has one or more moieties attached to its surface that confer cell-type specificity to the nanoparticle, referred to herein at times as a "targeting moiety". As used herein "cell-type specificity" means the nanoparticle is more likely to bind to a specific cell type than other cell types. For example, in certain implementations, the mesoporous silica nanoparticle further comprises at least one hyaluronic acid, conjugated thereto. In exemplary implementations the hyaluronic acid moiety facilitates binding to colon cancer cells.

In certain aspects, the targeting moiety is chosen from hyaluronic acid, folate, transferrin, trastuzumab, pamidronate, iRGD circular peptides, TAT peptides, DUPA, low molecular weight heparin, and/or specific antibodies. By their chemical nature, the targeting moiety can be heterocyclic compounds, proteins, peptides, glycoproteins, carbohydrates, amino acids, carboxylic acids, or phosphonates.

According to further embodiments, the pores of the mesoporous silica nanoparticle are sealed by a metalloprotein matrix. In exemplary implementations, metalloprotein matrix is attached to the nanoparticle surface electrostatically. In further aspects, metalloprotein matrix is attached to the nanoparticle by way of a covalent bond. According to the foregoing embodiments, the disclosed composition is unable to cross the blood brain barrier upon systemic administration to a subject.

In exemplary embodiments, the pores of the mesoporous nanoparticle are sealed by a protein matrix comprised of a matrix metalloprotease substrate. In certain embodiments, the matrix metalloprotease substrate is a substrate of a matrix metalloprotease chosen from of MMP-1, -2, -7, -9 and -1. In further embodiments, the matrix metalloprotease substrate is a substrate of MMP-7 Such embodiments are particularly useful in the treatment of CRC. In exemplary implementations, the matrix metalloprotease substrate is casein. In further implementations, the matrix metalloprotease substrate is a substrate of hyaluronic acid.

In function, these embodiments provide for tumor specific payload delivery. it is The nanoparticle cargo (e.g., VTD) is sealed inside the nanoparticles by the matrix metalloprotease substrate (e.g., MMP-7 substrate or casein) which serves as a "gate keeping" element preventing immediate payload release. The MMP-7 present in the cancerous tissue, but not in the normal tissue, will digest via enzyme cleavage the "gate keeping" element and release the cargo, in a tumor specific manner.

In certain embodiments, the foregoing mesoporous nanoparticle are loaded with modified VTD (e.g., PLE or PEG-PLE modified VTD). In certain alternative embodiments, mesoporous nanoparticle are loaded with unmodified VTD. It will be understood that the loading of unmodified VTD into the disclosed mesoporous nanoparticles will overcome many of the neurotoxicity problems normally associated with administration of VTD.

According to certain aspects, the administration of the disclosed composition increases the activity of UBXN2A. In a further aspect, the administration of the disclosed composition increases the binding of UBXN2A to mot-2. In a further aspect, the administration of the disclosed composition disrupts binding between p53 and mot-2. In a still further aspect, the administration of the disclosed composition increases p53 nuclear translocation.

In certain aspects, the disclosed composition is administered in a therapeutically effective amount. In further aspect, the cancer is colorectal cancer. In a still further aspect, the cancer is characterized by elevated Mortalin-2 levels.

Further disclosed herein is as method of treating colorectal cancer in a subject, comprising administering to the subject an effective amount of a composition disclosed herein.

According to certain embodiments, the subject suffers from metastatic colorectal cancer. According to further embodiments, the composition selectively binds colorectal cancer cells. In further aspects, the disclosed composition selectively binds colorectal cancer cells via hyaluronic acid conjugated to the composition. In yet further aspects, the composition has reduced neurotoxicity relative to a comparable dose of unmodified VTD.

Depending upon the subject to be treated and the route of administration, the compounds of the invention may be administered at varying doses. Although doses will vary from subject to subject, suitable daily doses are in the range of about 1 to about 1000 mg (e.g., about 1 mg, about 5 mg, about 10 mg, about mg, about 20 mg, about 25 mg, about 30 mg, about 35 mg, about 40 mg, about 45 mg, about 50 mg, about 75 mg, 100, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg, and the like, or any range or value therein) per subject, administered in single or multiple doses. More preferred daily doses are in the range 2.5 to 250 mg (e.g., about 2.5 mg, about 3 mg, about 3.5 mg, about 4 mg, about 4.5 mg, about mg, about 5.5 mg, about 6 mg, about 6.5 mg, about 7 mg, about 7.5 mg, about 8 mg, about 8.5 mg, about 9 mg, about 9.5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, or about 250 mg and the like or any range or value therein) per subject.

Individual doses of compounds of the invention may be in the range 1 to 100 mg (e.g., about 1 mg, about 2 mg, about 3 mg, about 4 mg, about 5 mg, about 6 mg, about 7 mg, about 8 mg, about 9 mg, about mg, about 11 mg, about 12 mg, about 13 mg, about 14 mg, about 15 mg, about 16 mg, about 17 mg, about 18 mg, about 19 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about about 90 mg, about 95 mg, or about 100 mg, and the like, or any range or values therein). Advantageously, compounds of the present invention may be administered in single doses, e.g. once daily or more seldom, or in a total daily dosage administered in divided doses of two, three or four times daily.

In certain embodiments, wherein the subject has been diagnosed with colon cancer, the disclosed composition is administered locally. According to certain implementations of these embodiments, the composition can be administered by way of a colonoscopy. In these implementations, the composition may be administered at a dose of about 0.06 mg VTD (or modified VTD) per 1 cm 3 tumor mass.

In certain embodiments, wherein the subject has been diagnosed with colon cancer, the disclosed composition can be administered systemically. In exemplary implementations of these embodiments, the composition is administered by way of an IV injection. In exemplary implementation of these embodiments, the IV injection is at a dose of about 0.1 mg/kg subject body weight.

According to further embodiments, the disclosed method further comprises administering the composition in conjunction with at least one other treatment or therapy (as described further below).

According to further aspects, administering the disclosed composition increases UBXN2A protein levels in the subject.

In yet further embodiments, administration of the disclosed composition reduces the formation of electrophilic ortho-quinones in catechol metabolites in the subject relative to administration of unmodified VTD. In exemplary implementations, the composition has reduced neurotoxicity relative to comparable dose of unmodified VTD.

According to further embodiments, administration of the disclosed composition(s) suppresses the mTORC2 pathway.

According to still further embodiments, the subject has be shown to be resistant to one or more chemotherapy.

Further disclosed herein is a method of preventing cancer in a subject, comprising administering to the subject a prophylactically effective amount of a composition comprising a polypeptide veratridine PLE or PEG-PLE conjugate and a pharmaceutically acceptable carrier thereof. In certain aspects, the subject has a high risk of developing colorectal cancer. In further aspects, the subject is obese.

In an aspect, the method further comprises co-administering an anti-neoplastic agent.

In an aspect, the method further comprises administering the composition as a bolus and/or at regular intervals. In as still aspect, the method further comprises administering the composition intravenously, intraperitoneally, intramuscularly, subcutaneously, or transdermally.

In an aspect, the method comprises administering the composition in conjunction with at least one other treatment or therapy. In a further aspect, the other treatment or therapy is chemotherapy.

In an aspect, the method further comprises diagnosing the subject with cancer. In a further aspect, the subject is diagnosed with cancer prior to administration of the composition.

In a still further aspect, the method further comprises evaluating the efficacy of the composition. In a yet further aspect, evaluating the efficacy of the composition comprises measuring tumor size prior to administering the composition and measuring tumor size after administering the composition. In a yet further aspect, evaluating the efficacy of the composition occurs at regular intervals. In a further aspect, the method further comprises optionally adjusting at least one aspect of method. In a still further aspect, adjusting at least one aspect of method comprises changing the dose of the composition, the frequency of administration of the composition, or the route of administration of the composition.

In an aspect, disclosed herein is a method for identifying an anti-neoplastic agent, the method comprising: selecting a candidate compound; contacting a cell with the candidate compound; determining the expression levels of UBXN2A in the cell, wherein the candidate compound is identified as a suitable anti-neoplastic agent if UBXN2A is up regulated, compared to expression levels of UBXN2A in the same type cell in the absence of the candidate compound.

Experimental

The following examples are put forth so as to provide those of ordinary skill in the art with a complete disclosure and description of certain examples of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Disclosed herein is the finding that the UBXN2A protein is a positive regulator of p53 through its interaction with the C-terminus of mot-2 where the p53-binding site is located. UBXN2A facilitates the translocation of WT-p53 to the nucleus where p53 regulates its target genes, particularly those involved in apoptosis. These results introduce UBXN2A as an important anticancer factor that can contribute to p53 localization and activation as a host defense mechanism against cancerous growth. Because fully functional p53 can reverse tumor formation and progression as well as postpone tumor relapse,[11] characterization of mot-2's endogenous regulators may lead to a new class of therapeutic interventions in tumors with high levels of mot-2.

A number of studies have reported the contribution of the UBXD family of proteins to different cancers.[12,13] Expression of these UBX domain-containing proteins correlate positively or negatively with tumor progression in a tissue-specific manner.[14] UBXN2A, as a p97-associated protein, is involved in protein quality control.[15] A set of experiments were conducted to determine whether UBXN2A might have a role in apoptosis in cancer cells. As cell detachment, cell shrinking, and alteration of nuclear morphology are ubiquitous aspects of apoptosis, these apoptotic features were examined in the presence of UBXN2A. HCT-116 colon cancer cells transfected with GFP-empty, GFP-p53, or GFP-UBXN2A. GFP-p53 significantly increased the number of cells detaching from the plates at 48 and 72 h post-transfection as compared with the vehicle, which is indicative of typical late stage apoptosis (FIG. 1a, FIG. 9A). Similarly, UBXN2A expression induced at least 50% cell detachment as early as 48 h post-transfection (FIG. 1a, FIG. 9A). We next asked whether UBXN2A expression leads to apoptotic characteristics (condensed chromatin and apoptotic bodies), which are ubiquitous aspect of apoptosis. We examined these in the presence of UBXN2A and p53 in fixed cells stained with DAPI. Expression of GFP-UBXN2A and GFP-p53 significantly increased the number of nuclei with condensed chromatin and apoptotic bodies formed in cells transiently transfected with GFP-p53 and GFP-UBXN2A (FIGS. 1b and c). On the basis of the cell morphology and reduced cell viability, it appeared that UBXN2A leads the cells to apoptosis, which was further confirmed by the large molecular weight DNA fragments in HCT-116 and LoVo colon cancer cells transiently transfected with GFP-UBXN2A or GFP-empty vector (FIG. 9B).

UBXN2A Induces Cell Cytotoxicity in a Cell Type-Dependent Manner

In another set of experiments, we used crystal violet-based cytotoxicity assays to compare the cytotoxicity of UBXN2A in four colon cancer cell lines as well as MCF7 breast cancer cells (FIGS. 9C and 9D). Statistically significant cytotoxicity induced by UBXN2A was confirmed in HCT-116 and LoVo cell lines with WT-p53 (FIG. 1d). In addition, we chose SW480 and HT-29 colon cancer with mutant p53 for the cytotoxicity assay. We observed significant cell cytotoxicity in the presence of UBXN2A in HT-29 (~50%), while UBXN2A expression had no significant induction of cytotoxicity in SW480 colon cancer cells (FIG. 1d).

Initial experiments in MCF7 showed no cell cytotoxicity in the presence of UBXN2A overexpression (FIG. 1d). Therefore, cell cytotoxicity was examined in MCF7 cells treated with suboptimal toxic dose of 5 µM etoposide for 24 h after transfection with GFP-empty or GFP-UBXN2A. UBXN2A had no effect on cell cytotoxicity in MCF7 cells in the presence of stress (FIG. 1d).

UBXN2A Binds Mot-2 in the Cytoplasm

Members of the UBXD family associate with a variety of cargoes that enable them to be involved in many cellular processes.[12] We therefore hypothesized that UBXN2A-induced apoptosis in cancer cells is due to UBXN2A's contribution to specific cancer-related pathways. We sought to identify the binding partners of UBXN2A in the HCT-116 cancer cells in the presence or the absence of the genotoxic agent etoposide (50 µM). HCT-116 cells were collected after a 24-h treatment, followed by IP with an anti-UBXN2A antibody immobilized on protein A magnetic beads (FIG. 10A). Cytosolic proteins that co-precipitated with UBXN2A, with and without etoposide, were analyzed by mass spectrometry-based proteomic approaches (FIG. 10B).[17] Several candidate proteins were identified, including mot-2. More mot-2 was associated with cytoplasmic UBXN2A under conditions of genotoxic stress. Next, iodixanol density gradient centrifugation[15,18] of cytoplasmic extracts from HCT-116 cells treated with etoposide (50 µM) was performed. UBXN2A co-sedimented with fractions containing mot-2 (lanes 7-9, FIG. 2a). As a control, the collected fractions for another UBXD family member, UBXN2C protein (p47) was probed. UBXN2C did not show co-sedimentation with mot-2, indicating the specificity of the co-sedimentation of UBXN2A with mot-2. UBXN2A-containing fractions were additionally enriched for p97 protein, which is a partner of UBXN2A.[12,15] A set of His-tag pull-down and IP experiments was performed in HEK293T (FIG. 2b) and HCT-116 cells (FIG. 2c). Cytoplasmic fractions from HEK293T cells transiently transfected with increasing amounts of (His)6-TYG-tagged UBXN2A were incubated with magnetic His-tag beads to isolate the mot-2 protein. FIG. 2b shows that upon increased exogenous expression of (His)6-UBXN2A the pulled down mot-2 signal intensities increased proportionally, indicating that (His)6-UBXN2A binds to endogenous mot-2 in a concentration-dependent manner. To determine whether endogenous UBXN2A and mot-2 proteins associate in vivo, the steady state level of mot-2 and UBXN2A was assessed in cells as well as normal and tumor tissues (FIG. 11). Results indicated that endogenous UBXN2A binds to mot-2 in HCT-116 cells in a p53-independent manner (FIG. 2c). Finally, we confirmed UBXN2A and mot-2 interaction in colorectal tumor tissues (FIG. 2d). We further confirmed that UBXN2A binds to mot-2 in HT-29 cells carrying mutant p53 (FIG. 9E). To further verify negative results obtained from MCF7 cells, we conducted an immunoprecipitation (IP) experiment using an anti-UBXN2A antibody. We found UBXN2A does not bind to mot-2 in MCF7 cells with and without stress (FIG. 9F). The molecular characteristics of mot-2 in MCF7 breast cancer cells versus colon cancer cells and lack of caspase 3 in MCF7 cells, which has specific role in apoptosis and in activation of caspase 6 and 7 are considered as potential reasons for the absence of cell death in MCF7 upon UBXN2A overexpression. Finally, IP experiments with an anti-UBXN2A antibody using normal human umbilical vein endothelial cell (HUVEC) lysates in the absence and the presence of recombinant GST-mot-2 showed UBXN2A only pulls down recombinant mot-2 (sufficient amount of mot-2) and not the endogenous mot-2 expressed in normal HUVEC cells (FIG. 9G).

Switching the Protein-Binding Preference of Mot-2 from p53 to UBXN2A

Because mot-2 binds to the cytoplasmic domain of p53 and sequesters WT-p53 in the cytoplasm, we asked whether binding UBXN2A to mot-2 can alter mot-2's affinity for p53. To test this hypothesis, we probed the fractions collected from the iodixanol gradient (FIG. 2a) with an anti-p53 antibody. p53 showed two peaks (FIG. 2e) of which the first, at fractions 3-5, dominantly showed co-fractionation with HSP90 protein, as expected, and partially with mot-2.[19] The second peak of p53 was at fractions 12 to 15, which may represent p53 association with HSC70/HSP70 complex (FIG. 2e). Notably, p53 was not highly abundant in the fractions that contained the majority of the co-sedimented UBXN2A and mot-2 proteins (fractions 7-9 in FIG. 2a versus FIG. 2e). These results suggest the binding of mot-2 to UBXN2A might inhibit the binding of mot-2 to p53. That is, the two complexes might be mutually exclusive. To further determine whether the binding of mot-2 to UBXN2A decreases the binding of mot-2 to p53, we performed two set of immunoprecipitation experiments with recombinant UBXN2A. FIG. 3a describes an in vitro competition immunoprecipitation assay system containing mot-2, p53, and an increasing amount of recombinant UBXN2A. In a competition mechanism, the increasing amounts of recombinant human UBXN2A decreased the intensity of mot-2 bands pulled down by anti-p53 antibodies. The lowest binding between p53-mot-2 was observed when UBXN2A and mot-2 were present in approximately a 1:1 ratio by their molecular mass (lane 1 versus lane 2). In FIG. 3b, cytosolic fractions enriched with mot-2 and p53 proteins (fractions 3-5, FIG. 2e) were incubated with recombinant GST-tag human UBXN2A protein. After the initial 2 h of incubation, samples were subjected to immunoprecipitation with anti-p53 antibodies. GST-UBXN2A and endogenous mot-2 ratio was 2.5:1 in the reaction. The presence of UBXN2A decreased the amount of mot-2 protein-bound p53 (FIG. 3b). Next, we decided to verify whether endogenous UBXN2A can interfere with mot-2-p53 binding using an ex vivo model. The HCT-116 cell line was identified as one of the best candidates for in vivo experiments, as HCT-116 has minimum expression of UBXN2A (FIG. 11B) while it has an abundant amount of mot-2-p53 complexes in the absence of stress. 6 FIGS. 3c-f showed that the amounts of UBXN2A mRNA and protein increased in HCT-116 cells treated with etoposide for 24 h, indicating that etoposide can induce upregulation of UBXN2A at RNA and protein levels. Moreover, immunofluorescence staining showed that UBXN2A located at the juxtanuclear region in unstressed HCT-116 cells forms a punctate distribution scattered throughout the cytoplasm in many cells upon etoposide treatment (FIG. 3g). This distinct punctate structure of UBXN2A was consistent with punctate p53 and mot-2 formation in colon cancer cell lines.6 As a result, we decided to verify whether UBXN2A decreases p53's binding to mot-2 in the presence of etoposide (20 and 50 µM). A set of co-immunoprecipitations of mot-2 with UBXN2A as well as mot-2 with p53 showed that an increasing association of UBXN2A and mot-2 correlates with an increased dissociation of p53 and mot-2 in an etoposide dose-dependent manner (FIGS. 3h and i).

UBXN2A Induces p53 Nuclear Accumulation

Figure 4:
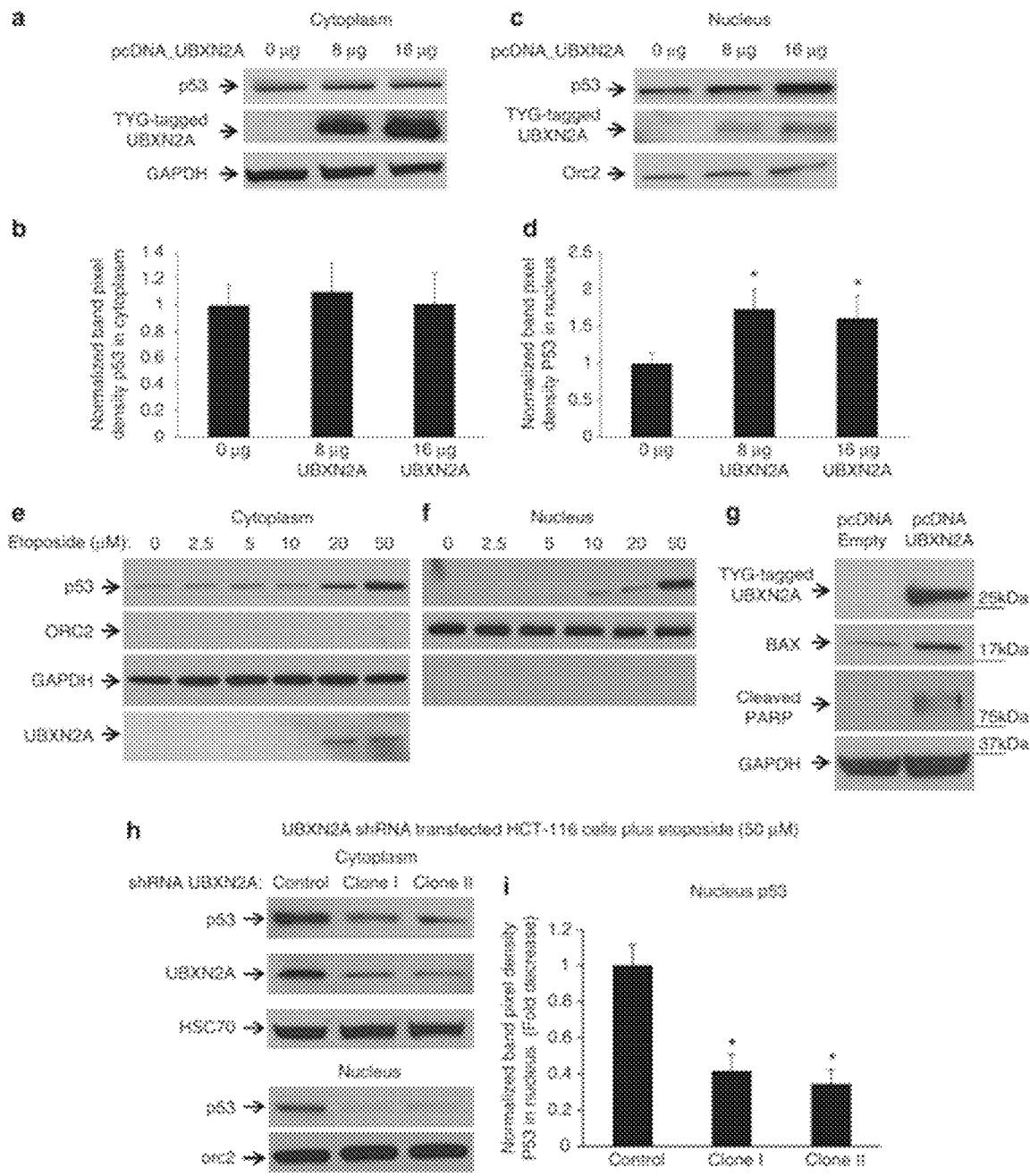
FIG. 4 shows UBXN2A induces p53 nuclear translocation in HCT-116 colon cancer cells. HCT-116 cells were transfected with the indicated amount of (His) 6-TYG-tagged UBXN2A plasmid.

Small molecules, p53 c-terminus peptides, and silenced mot-2 abrogate mot-2-p53 complexes, resulting in p53 nuclear localization. Because UBXN2A is capable of releasing p53 from mot-2, we decided to determine whether UBXN2A can lead to p53 nuclear accumulation in a similar mechanism. HCT-116 cells were transiently transfected with different amounts of UBXN2A plasmid. Exogenous UBXN2A was detected dominantly in the cytoplasm fraction (FIG. 4a), and, therefore, it is an ideal model to identify the cellular consequences of UBXN2A gain-of-function. After 48 h, nuclear and cytoplasmic fractions were collected, followed by WB analysis (FIGS. 4a-d). Panel d in FIG. 4 shows an increased level of UBXN2A leads to a significant increase in the amount of p53 in the nucleus. We did not observe any changes in p53 abundance in cytoplasmic fractions after an overexpression of UBXN2A, suggesting that nuclear accumulation of p53 is predominantly due to translocation from the cytoplasm into the nucleus (FIGS. 4a and b), as previously reported in the absence of active mot-2.[7,22] On the basis of the above data, we hypothesized that etoposide-dependent upregulation of UBXN2A should be linked with an increased level of p53 in the nucleus as well. Hence, we examined the stress-induced p53 nuclear localization in HCT-116. WB analysis of cytoplasm (FIG. 4e) and nuclear (FIG. 4f) fractions revealed that upregulation and nuclear localization of p53 becomes significant at 20 and 50 µM etoposide, which matches exactly with elevated UBXN2A at the same dosages. Similar to several previously reported scenarios,[23] co-upregulation of UBXN2A with p53 may be essential to inhibiting mot-2 and delivering maximum p53 into nuclei during the initiation of genotoxic stress. Similar results were obtained in response to single DNA-strand damage produced by UVB irradiation. In the next step, we decided to determine whether UBXN2A increases the transcriptional activities of p53. We found overexpression of UBXN2A led to upregulation of BAX protein[24] (FIG. 4g). In addition, the level of cleaved PARP increased in the presence of overexpressed UBXN2A (FIG. 4g). As expected, silencing UBXN2A (FIG. 4h) had the opposite effect, strongly reducing the p53 in the nucleus as well as decreasing the level of p53 in cytoplasm fractions (FIGS. 4h and i). Collectively, these two gain and loss functions of UBXN2A suggested that UBXN2A can increase the level of functional p53.

UBXN2A Preferentially Induces Apoptosis in Colon Cancer Cell Lines

FIGS. 5a and b show that the expression of GFP-UBXN2A significantly induces apoptosis in HCT-116 and SW48 cells as assessed by Annexin-V. Unlike HCT-116 and SW48 colon cancer cells, GFP-UBXN2A did not induce a significant level of apoptosis in normal colon fibroblast CCD-18Co cells. Staurosporine-treated uninfected cells were used as apoptosis-positive controls (FIGS. 12A and B). It has already been shown when cancer cells are cultured under high-density condition, cell death is often induced as a consequence of nutritional deficiency. With this in mind, HCT-116 cells at ~80% confluence were transfected with GFP shRNA-expressing lentiviral-based vectors (Clone I and II, FIG. 4h), followed by a 48-h incubation. As expected, cells transfected with scrambled shRNA show evidence of apoptosis, while expression of shRNAs (Clone I and II) against UBXN2A resulted in a significant reduction in apoptosis (FIG. 5C).

UBXN2A Induces Apoptosis and Suppresses Cell Growth Through a p53-Dependent Pathway To determine whether the UBXN2A-induced apoptosis observed in colon cancer cells is p53-dependent, we next compared the incidence of early apoptosis as measured by Annexin V and cell viability in HCT-116 p53+/+ and p53−/− in the presence and the absence of UBXN2A expression. HCT-116 cells (p53+/+ and p53−/−) were transfected with GFP-UBXN2A, followed by flow-cytometry analysis. The results showed that UBXN2A induces apoptosis in a p53-dependent manner (FIG. 6a), as there was not a significant change between GFP-empty and GFP-UBXN2A in p53−/− using the Annexin V apoptosis assay. The cell viability assay showed that GFP-UBXN2A is effective in HCT-116 p53+1+, indicating a need for the presence of p53 to mediate these effects (FIG. 6b).

UBXN2A Induces Caspase Pathways Through p53

Because p53-dependent apoptosis is primarily mediated through the activation of the caspase pathway, we next monitored the activity of the caspase pathway in the presence of UBXN2A. Measurement of the caspase 3/7 activity showed that overexpression of GFP-tagged UBXN2A significantly increases caspase activity in HCT-116 cells (FIG. 6c). Because cleaved caspase-3 mediates apoptosis and contributes to the chemopreventive functions of several agents in colorectal cancer, a caspase colorimetric assay was used to detect the activity of caspase-3 in noncancerous HEK-293T and HCT-116 colon cancer cells transiently transfected with (His)6-TYG-tagged UBXN2A or empty vector. HEK293T cells endogenously express mot-2. Only a significant twofold increase in caspase-3 activity was observed in HCT-116 cells expressing UBXN2A versus the empty vector (FIG. 6d).

UBXN2A Blocks Colon Cancer Migration and Invasion In Vitro

Recent evidence shows that inactivation of p53 triggers the progression of colorectal tumors from the adenoma to the carcinoma stage and enhances cancer invasiveness and lymph node metastasis.[30,31] Involvement of p53 in cell migration and cell invasion encouraged us to examine a possible role for UBXN2A in these two events. Overexpression of (His)6-UBXN2A decreased migration and invasion by nearly 50% in HCT-116 cells when the results were compared with (His)6-empty transfected cells (FIGS. 6e-h).

UBXN2A and p53 Share a Common Binding Site on the Mot-2 Protein

Figure 12:
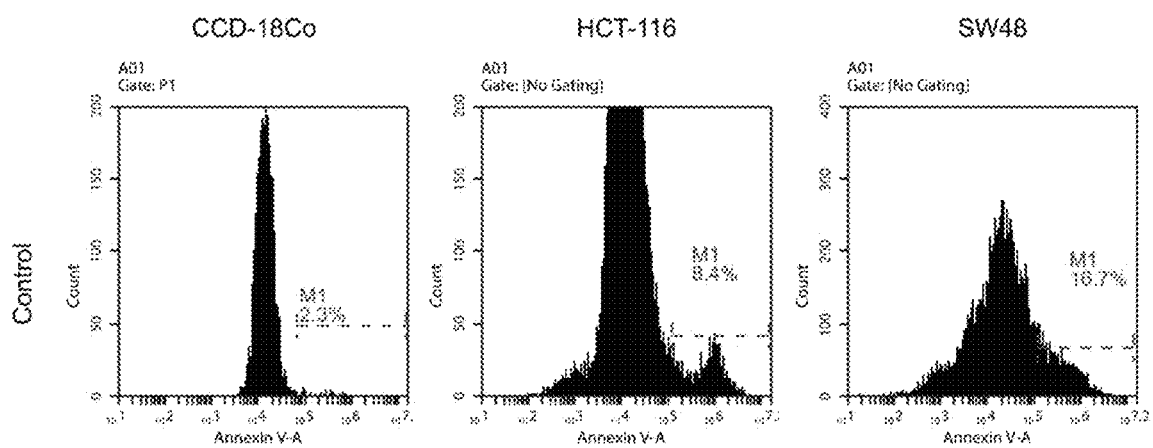
FIG. 12 shows Annexin V staining and flow cytometry as an assay for measurement of early apoptosis.
Figure 12:
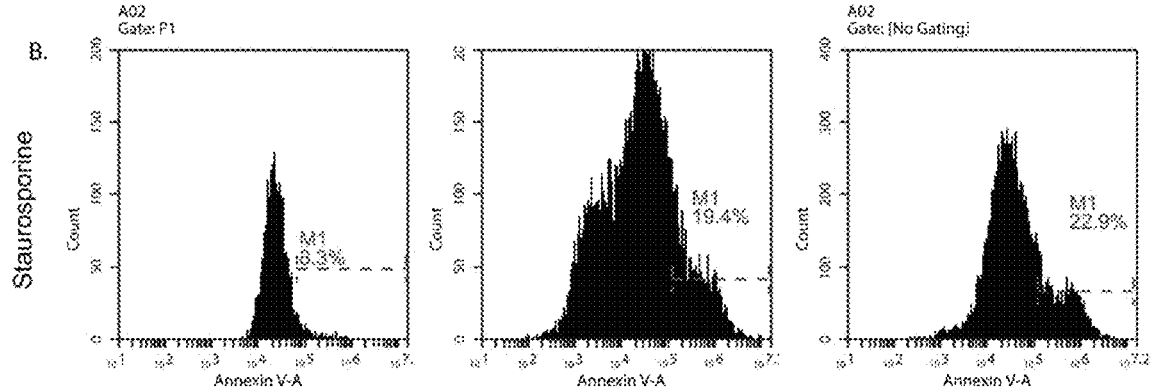
Figure 12:
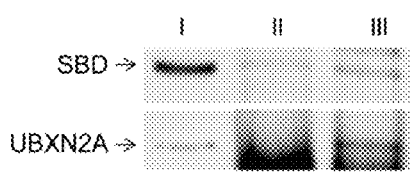
Figure 12:
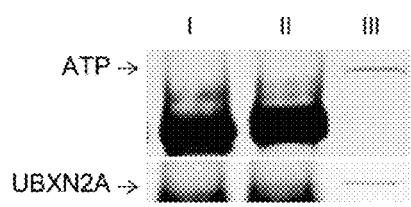

Because the p53-binding site of mot-2 located within the substrate-binding domain (SBD domain) in the range of 423 to 450 residues, we hypothesized that the p53-mot-2 interaction can be competitively disrupted by the binding of UBXN2A to the SBD domain of mot-2. A yeast two-hybrid (Y2H) strategy[15] revealed that UBXN2A uses its SEP domain to interact with mot-2, which is sufficient for this interaction (FIGS. 7a-f). The binding of UBXN2A to the truncated mot-2 (1-506 aa) and SBD (432-674 aa) and its unsuccessful binding to ATP domain (1-437aa) illustrated that the UBXN2A-binding site is located in the range of 438-506 residues where there is a part of p53's binding site, according to Utomo et al.[33] In addition, a set of IP experiments confirmed UBXN2A only binds to the SBD domain (FIG. 12C) and not the ATP domain (FIG. 12).

Kaul et al.[34] showed that the Mot-2 amino-acid residues 253-282 Mot-2 are critical for its binding to p53. However, these results are in contrast to results reported by ISosfson et al where their IP experiments showed that the association of p53 occurs via the SBD-binding domain of Mot-2 and not the ATP domain. 32 Furthermore, a molecular docking study by Utomo et al. confirmed p53 protein bind to substrate-binding domain of Mot-2 located in the C-terminus.[33] We found that some of the binding sites of mot-2 to p53, as predicted by bioinformatics[33] and in vitro assays,[32] were found to be involved in binding of mot-2 to UBXN2A, suggesting that mot-2-p53 and mot-2-UBXN2A binding may be competitive or even mutually exclusive.

Furthermore, a set of Annexin V apoptosis assays and a crystal violet cell cytotoxicity assay verified that the SEP domain of UBXN2A is sufficient to induce apoptosis in HCT-116 cells, while the UBX domain alone failed to induce apoptosis (FIGS. 7g and h).

UBXN2A Overexpression Decreases the Growth of HCT-116 Human Colon Carcinoma Cells Xenografted in Mice Untransfected HCT-116, as well as UBXN2A, or empty cell suspensions, were injected subcutaneously into the flanks of immunodeficient mice. A portion of the transfected cells was lysed and analyzed by WB to demonstrate that the injected cell lines carried the desired exogenous proteins (FIG. 8a). Tumors arose around 16 days after injection and were measured every other day. Our results demonstrate a significant reduction of tumor growth in UBXN2A xenografts compared with empty xenografts and untransfected HCT-116 (FIGS. 8b-d and FIG. 13). Immunohistochemical analysis of tumor sections showed that expression of UBXN2A markedly decrease expression of the cell proliferation marker Ki67 (FIG. 8e). In addition, a TUNEL assay showed that overexpression of UBXN2A resulted in greater induction of apoptosis compared with tumors expressing empty vector (FIG. 8f).

Veratridine is a UBXN2A Enhancer and Functions as an Anticancer Agent

A drug screen was conducted to identify compounds that enhanced UBXN2A. Through this screen, it was determined that Veratridine (VTD), a plant alkaloid, transactivates the UBXN2A promoter and increases UBXN2A protein levels. Administration of VTD resulted in the induction of anti-proliferative and pro-apoptotic effects uniquely in cancer cells in a UBXN2A- in a p53-dependent manner.

Induction of the Anti-Mot-2 Protein UBXN2A Suppresses Tumor Growth in Xenografts Several of the UBX-domain-containing proteins play positive or negative regulatory roles in diverse types of cancers [4, 14-16]. We generated two Tet-on inducible HCT-116 colon cell lines expressing GFP-empty or GFP-UBXN2A. Fluorescent microscopy and western blot (WB) analysis showed that incubation with Doxycycline (DOX) for 48 hours induces expression of GFP-empty or GFP-UBXN2A in HCT-116 cells (FIG. 15A-B). Incubation of cells with DOX for 48 and 72 hours significantly increased early apoptosis in GFP-UBXN2A-expressing cells using Annexin V marker (FIG. 15C and S2). Flowcytometry results further confirmed that expression of an apoptotic marker, caspase-3, significantly increased following DOX-induced UBXN2A expression (FIG. 15D and S3A). Because our previous data [4] and others' indicate reactivation of p53 upon mot-2 inhibition targets both cell proliferation and apoptosis, we further investigated whether DOX-induced UBXN2A expression affects cell cycle arrest in addition to the activation of the apoptosis pathway Staining of the p21 cell cycle arrest marker showed that induction of UBXN2A expression increased expression of the p21 protein, which can lead to arresting cell growth (FIG. 15E). Because the anti-cancer function of UBXN2A is mediated through mot-2-p53, we hypothesized that UBXN2A induction would potentiate the cytotoxic effects of standard chemotherapy which cause DNA damage and activate pathways that signal to p53 [2]. To answer this question, we examined apoptosis and cell death markers in UBXN2A-induced cells treated with 5-FU, a thymidylate synthase inhibitor commonly used in patients with colon cancer. Our flow cytometry data indicated that expression of caspase-3 and PARP (apoptosis markers) and Sytox red (cell death marker) were significantly higher when UBXN2A-induced cells incubated with 5-FU (FIG. 15F-H).

We next decided to examine how induction of UBXN2A contributes to tumor suppression in xenograft mouse models. After injection of inducible cells subcutaneously into the lower flanks of nude mice, mice with a palpable tumor volume (~5 mm, early-staged tumor experiments [18]) were fed either normal or DOX diets for 40 days. The data confirmed that induction of UBXN2A can slow the growth of tumors (FIG. 15I-J). WB of dissected tumors confirmed successful induction of GFP-empty and GFP-UBXN2A (FIG. 15K). Measurement of the growth rate of tumors showed that induction of UBXN2A led to a 50% reduction of tumor size and mass as well as the central necrosis in some mice 40 days after implantation (FIG. 15L). In an advanced staged tumor response approach [18], we confirmed that induction of UBXN2A can lead to more apoptotic events during the development of established tumors using PSVue 794, a distinct marker of apoptosis used in live mice (S3B-E).

Hsp70 family proteins have been suggested to serve as prognostic and therapeutic markers for cancer cells.[2,14,35,36] Mot-2 particularly becomes a tumorigenesis factor in colorectal cancers, and thus is a potential candidate target for cancer therapy.[2] We first showed that UBXN2A induces cytotoxicity in a cell type-dependent manner in the presence of wild-type or mutant p53. The level of cytotoxicity (~50%) induced by UBXN2A in HCT-116, LoVo, and HT-29 was similar to previous reports where cytoplasmic p53 peptides significantly decreased colony formation.[21] Interestingly, Gestl and Ann Bottger observed the mutant p53 binds to mot-2 in HT-29 colon cancer cell line.6 Lu et al.[7,9] reported that silencing of mot-2 in hepatocellular carcinoma (HCC) cells with mutant p53 can lead to apoptosis. Therefore, we concluded the induced apoptosis in HT-29 cells in the presence of UBXN2A is mediated through mutant p53 but independent to p53's transcriptional activation function.

Elevated Levels of Mortalin-2 (Mot-2) in Clinical Samples of Colon and Breast Cancer are Associated with Cancer Progression.

We conducted a series of protein arrays (S1A-B) to compare the level of mot-2 in tumor tissue versus adjacent normal tissues. The results indicated that 75% (36 out of 48) of colon tumors show 1.5 fold or greater overexpression of mot-2 as compared to their normal adjacent tissues, with a maximum of 7.6 fold (P<0.001, FIG. 14A). We observed similar upregulation of mot-2 protein in breast cancer patients (P<0.001, FIG. 14B). The increase in mot-2 levels was found to be higher among the tumor tissues of male patients as compared to female patients (FIG. 14C). A lower rate of upregulated mot-2 in females may explain the different rate of incidence and survival in women with colon cancer [13]. Moreover, upregulation of mot-2 only in breast cancer patients was age dependent. The level of mot-2 was found to be significantly higher in comparatively younger females with an average age of 48.71±1.54 years (FIG. 14D). The upregulation of mot-2 shows a grade- and stage-dependent manner in both colon and breast cancers (FIG. 14E-H), indicating its prognostic aspect. These in vivo results indicate mot-2 as a significant oncoprotein in colon cancer and a potential cancer therapy target.

Induction of the Anti-Mot-2 Protein UBXN2A Suppresses Tumor Growth in Xenografts Several of the UBX-domain-containing proteins play positive or negative regulatory roles in diverse types of cancers [4, 14-16]. We generated two Tet-on inducible HCT-116 colon cell lines expressing GFP-empty or GFP-UBXN2A. Fluorescent microscopy and western blot (WB) analysis showed that incubation with Doxycycline (DOX) for 48 hours induces expression of GFP-empty or GFP-UBXN2A in HCT-116 cells (FIG. 14A-B). Incubation of cells with DOX for 48 and 72 hours significantly increased early apoptosis in GFP-UBXN2A-expressing cells using Annexin V marker (FIG. 15C and S2). Flow cytometry results further confirmed that expression of an apoptotic marker, caspase-3, significantly increased following DOX-induced UBXN2A expression (FIG. 15D and S3A). Because our previous data [4] and others' indicate reactivation of p53 upon mot-2 inhibition targets both cell proliferation and apoptosis, we further investigated whether DOX-induced UBXN2A expression affects cell cycle arrest in addition to the activation of the apoptosis pathway Staining of the p21 cell cycle arrest marker showed that induction of UBXN2A expression increased expression of the p21 protein, which can lead to arresting cell growth (FIG. 15E). Because the anti-cancer function of UBXN2A is mediated through mot-2-p53, we hypothesized that UBXN2A induction would potentiate the cytotoxic effects of standard chemotherapy which cause DNA damage and activate pathways that signal to p53 [2]. To answer this question, we examined apoptosis and cell death markers in UBXN2A-induced cells treated with 5-FU, a thymidylate synthase inhibitor commonly used in patients with colon cancer. Our flow cytometry data indicated that expression of caspase-3 and PARP (apoptosis markers) and Sytox red (cell death marker) were significantly higher when UBXN2A-induced cells incubated with 5-FU (FIG. 15F-H).

We next decided to examine how induction of UBXN2A contributes to tumor suppression in xenograft mouse models. After injection of inducible cells subcutaneously into the lower flanks of nude mice, mice with a palpable tumor volume (~5 mm, early-staged tumor experiments [18]) were fed either normal or DOX diets for 40 days. The data confirmed that induction of UBXN2A can slow the growth of tumors (FIG. 15I-J). WB of dissected tumors confirmed successful induction of GFP-empty and GFP-UBXN2A (FIG. 15K). Measurement of the growth rate of tumors showed that induction of UBXN2A led to a 50% reduction of tumor size and mass as well as the central necrosis in some mice 40 days after implantation (FIG. 15L). In an advanced staged tumor response approach [18], we confirmed that induction of UBXN2A can lead to more apoptotic events during the development of stablished tumors using PSVue 794, a distinct marker of apoptosis used in live mice (S3B-E).

Discovery of UBXN2A Enhancers Using a Luciferase-Based Assay

Our in vivo results encouraged us to screen for compounds that can enhance expression of UBXN2A. Using the UBXN2A promoter upstream of a luciferase construct that was transiently transfected to HCT-116 cells, we performed a high-throughput drug screen with 1800 FDA approved drugs, synthetic compounds, and natural products. Forty-eight hours after transfection, cells were treated with compounds for 24 hours in triplicate (FIG. 16A). The results showed that a 40 μM Veratrine sulfate (VH) resulted in a ~two fold increase in luciferase activity (FIG. 3B-C). We looked at protein expression of UBXN2A as well as P47 (another member of the UBXD family) to confirm the selectivity of VH as a selective enhancer of UBXN2A protein in cells. The WB results showed that VH selectively upregulates UBXN2A (FIG. 3D). More importantly, intraperitoneal injection (IP) of 0.125 mg/kg VH every day for 28 days leads to the selective upregulation of UBXN2A in small intestine and colon tissues of mice, while, due to a high pool of UBXN2A in the liver, these was no significant changes in the liver tissue (FIG. 3E). We observed a different level of VH-dependent UBXN2A induction in different segments of the gastrointestinal system (esophagus to rectum; data not shown). These data suggest that VH can increase UBXN2A levels in vivo to a functionally meaningful degree, as we observed following UBXN2A induction in xenograft tissues (FIG. 15).

The alkaloid fraction of Veratrine is known to contain a mixture of two major alkaloid esters: Veratridine (VTD) and Cevadine [21, 22]. VTD, with a veratroyl group at the 3-OR1 position and a free hydroxyl group at the 15-O-R2 position can function as an antihypertensive plant-derived substance. The anti-proliferative and apoptotic functions of VTD are mediated by wild-type p53 [28]. Based on the above evidence, we hypothesized that the purified form of VH, VTD, is a major UBXN2A inducer. To answer this question, we treated HCT-116 cells with 20 and 40 µM of VTD for 24 hours. WB of the total cell lysate showed that VTD induces UBXN2A expression in a dose-dependent manner (FIG. 16G).

VTD Selectively Targets Cancer Cells while Non-Cancerous Cells Remain Intact

Figure 15:
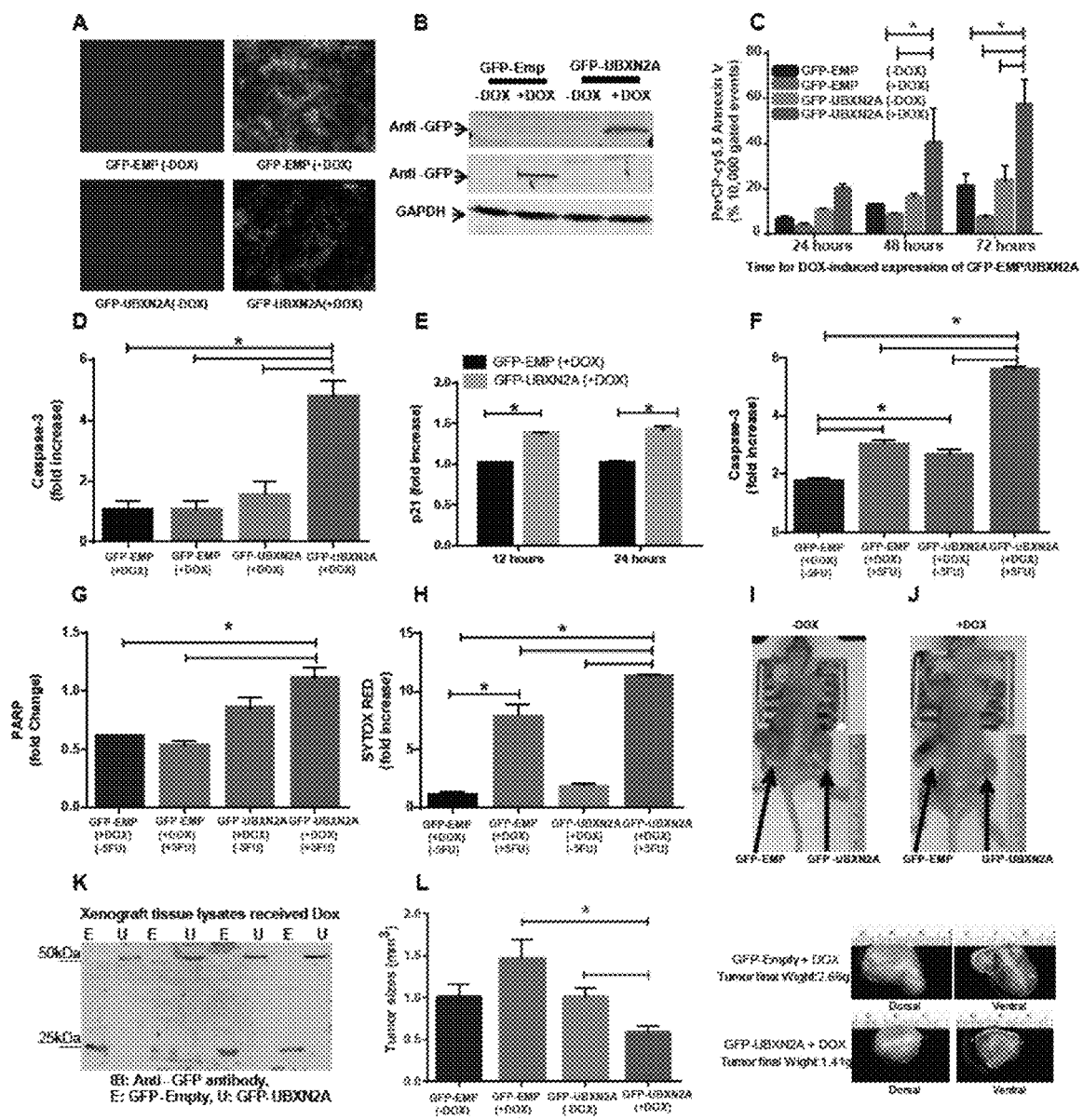
FIG. 15 shows how induction of UBXN2A slows the growth of a colon cancer tumor ex vivo and in a mouse xenograft model by 50%.
Figure 17:
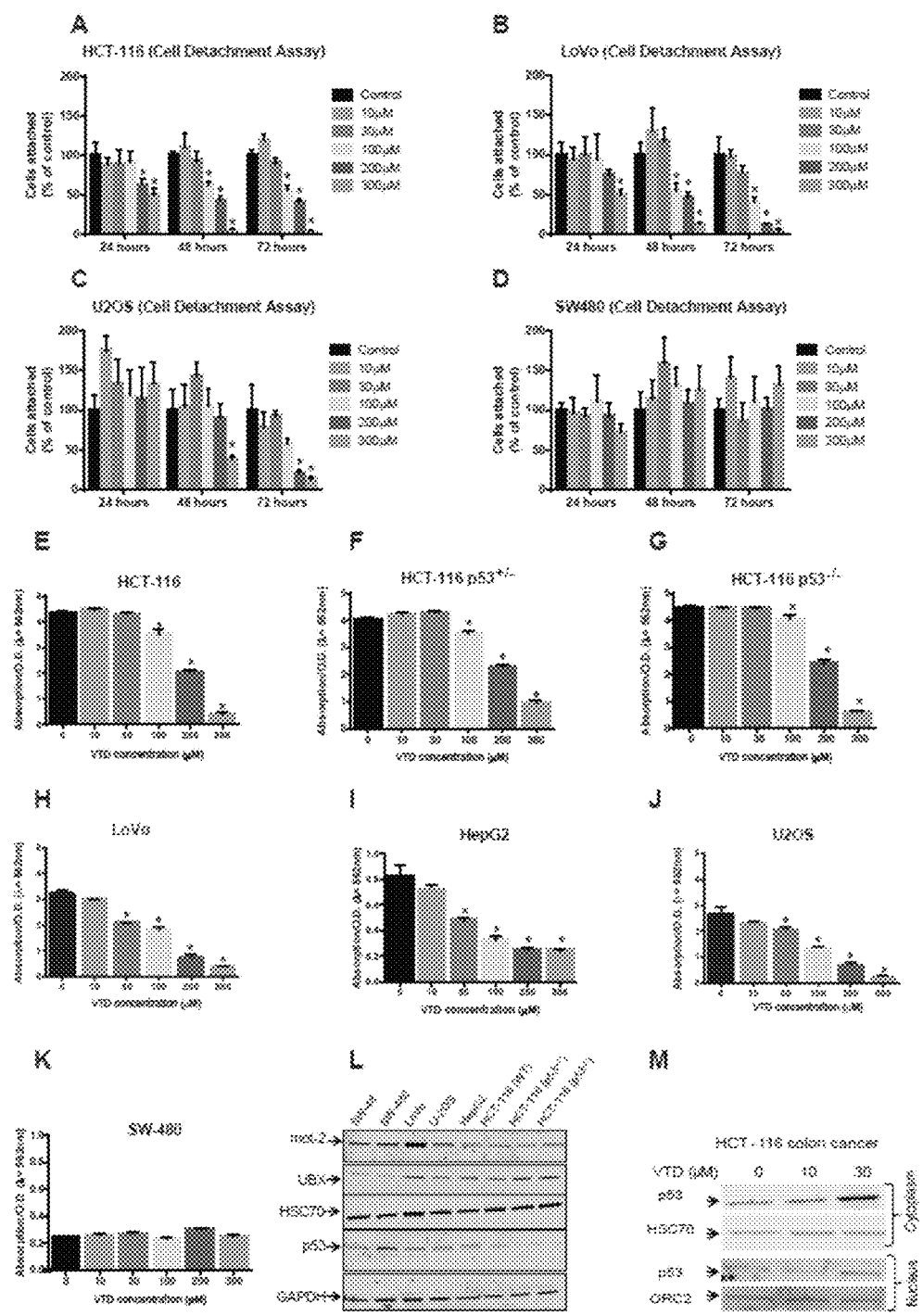
FIG. 17 shows the induction of apoptosis and in vitro cytotoxicity by VTD in human cancer cell lines with different statuses of p53 and mot-2.

Based on the above results, we then hypothesized that VTD-induced UBXN2A leads to apoptosis and cell death mimicking the Tet-on induced-UBXN2A model (FIG. 15). As cell detachment and cell shrinking are ubiquitous aspects of apoptosis [29], we examined these features in four cancer cell lines: HCT116 (WT-p53), LoVo (WT-p53), SW-480 (mutant-p53), and U2OS (WT-p53), all in the presence of VTD (FIG. 17, S4). The results showed that VTD significantly increases cell detachment of HCT-116 (poorly differentiated colon cancer cell line, FIG. 17A), LoVo (well-differentiated colon cancer cell line, FIG. 17B) and U2OS (osteosarcoma with perinuclear mot-2 expression [30, 31], FIG. 17C) in a dose-dependent and time-dependent manner. In SW480, VTD had no effect on cell detachment, indicating VTD requires WT-p53 to induce its effect (FIG. 17D). In addition, live cell imaging of cells revealed VTD induces cell shrinking and rounding resembling apoptosis changes in HCT-116 (S4A), LoVo (S4B), and U2OS (S4C) in a dose- and time-dependent manner, while SW480 cells remain unchanged (S4D).

We next performed a clonogenic survival assay (S4E) to determine colony formation in cancer cells in the presence and absence of VTD. The results showed that VTD reduces colony formation in HCT-116 in higher doses. Using HCT-116 p53+/- or p53 -/-, we showed that the anti-colony formation role of VTD is still partially p53 dependent in effective doses (FIG. 17E-G). Expectedly, VTD significantly decreases the number of colonies of LoVo (FIG. 17H), HepG2 (liver cancer cell line, FIGS. 17I), and U2OS (FIG. 17J) with as low as 30 µM VTD concentration, while SW480 cells with mutant p53 had no response to VTD, even at higher doses (FIG. 17K). At the same time, we measured the mot-2, p53, and UBXN2A protein levels in all these cell lines. The WB analysis showed mot-2 levels vary based on the cancer cell type, while HSC70 is fairly equal in all examined cell lines (FIG. 17L). To verify whether VTD-induced cell death is mediated through the UBXN2A-mot-2-p53 axis [4], we looked at the expression of p53 in the cytoplasm and nucleus of HCT-116 cells following VTD treatment. WB showed that VTD increases WT-p53 levels both in the cytoplasm and nucleus where p53 can activate its downstream cascades in dependent- or independent-transcriptional manners [32]. Due to a high cell death in higher doses of VTD, we could not use WB analysis for reliable p53 and UBXN2A detection and quantification. Finally, we checked the effect of VTD on non-cancerous cell lines. We incubated human umbilical vein endothelial cells (HUVECs), which mimic non-cancerous endothelial cells next to tumor cells, with VTD (S4G). The HUVEC cells did not respond to VTD in the first 24 hours, followed by a moderate response at the highest dose of VTD (30004) in 48 hours. Together, these results suggest while VTD can inhibit p53 sequestration by mot-2 via UBXN2A expression at low doses and initiates early apoptosis, VTD needs higher doses to trigger cell death under low stress as previously described [2]. Due to the different levels of the stress condition[33], we observed more sensitivity to VTD in LoVo and U2OS cells versus HCT-116 cells. In addition, lack of similar response in normal cells due to the absence of stresses and cytoplasmic mot-2 further explains VTD is therefore a drug that selectively targets cancer cell.

VTD Induces Apoptosis and Cell Death Via the UBXN2A-Mot-2-p53 Axis

We decided to confirm whether VTD-induced tumor suppression is indeed mediated via the UBXN2A-mot-2-p53 axis (FIG. 18H). After initial verification with WB (FIG. 18A), HCT-116 (p53+/+ and p53 -/-) and LoVo were treated with VTD for 24, 48, and 72 hours (FIG. 18B-D). The MTT cell proliferation assay showed a 24 hour treatment with VTD was not sufficient to produce any cytotoxic or anti-proliferative effect on HCT-116 cell lines; however, VTD at higher doses significantly decreases the viability of well-differentiated LoVo cells (FIG. 18C-D). All three cell lines started to respond to VTD at 48 hours, and reduction of cell viability reached a maximum at 72 hours, particularly in LoVo cells. We defined this phenomenon as a delayed cytotoxic response, since it occurs through UBXN2A transcription, as previously described for other anti-cancer agents [34]. The viability of HCT-116 p53+1+ was found to be significantly lower than HCT-116 p53-/- in the presence of VTD, indicating that VTD pointedly acts via p53 in the cells. However, HCT-116 p53-/- cells started to respond to VTD at higher doses after 48 hours, which indicates VTD can partly trigger cell cytotoxicity independent of the p53 mechanism (FIG. 18D) probably due to mot-2 inhibition unrelated to p53 sequestration (FIG. 18H). In addition, these results indicate that the conditions of the well-differentiated colon cancer cells (LoVo) increases the effectiveness of VTD as described for other anti-cancer compounds [35]. In the second set of experiments, we treated two stable UBXN2A silenced clones of HCT-116 along with controls with VTD. We observed that UBXN2A silenced cells showed greater cell viability than control cells, confirming that VTD requires UBXN2A to decrease the cell viability (FIG. 18E). Staurosporine-treated cells were used as a positive control (S4F). Besides the MTT assay, a set of Sytox red flow cytometry experiments further confirmed that in the absence of the UBXN2A gene there is a significant decrease in the cell death (FIG. 5F; S5A-C). Finally, to understand the contribution of mot-2 to the anti-cancer mechanism of VTD, we used a mot-2 inhibitor known as MKT-077 [7] along with VTD in well-differentiated SW-48 (WT-p53) colon cancer cells for 72 hours. Due to the critical role of mot-2 in the mitochondria, we could not use a silencing strategy for mot-2 in this set of experiments. VTD alone significantly decreased cell viability in a dose-dependent manner; however, upon mot-2 inhibition in the cytoplasm by MKT-077, VTD had no significant effect on cell viability (FIG. 18G). Together, these data show that VTD requires UBXN2A, mot-2 and p53 for its action (FIG. 18H). Combination Treatment with VTD and Chemotherapeutic Agents Results in Synergistic Cytotoxicity in Colon Cancer Cells Targeting carcinogenic-specific mechanisms by novel natural products, alone or in combination with standard chemotherapies, may provide synergy with existing treatments, lessen side effects, and ultimately improve both life expectancy and quality of life for cancer patients [36]. To examine whether VTD has synergism or additive effects with standard chemotherapeutic drugs commonly used in colon cancer patients, we first combined different doses of VTD with suboptimal doses of etoposide as determined by an MTT assay in HCT-116 versus LoVo cells in a time-dependent manner (S6A-C). It is noteworthy that etoposide showed more effectiveness in well differentiated cells (LoVo) than HCT-116 cells, similar to effects observed with VTD alone. Combination of VTD with a suboptimal dose of etoposide significantly potentiates the cytotoxic effect of VTD in HCT-116 (FIG. 19A-C) and LoVo (FIG. 19D-F). We analyzed our results with CalcuSyn software in order to understand the mode of interaction of the tested drugs (S6D-F). The median-effect plots for HCT-116 and LoVo revealed that it was only when we mixed higher concentrations of VTD with sub-optimal concentrations of etoposide (5 μM) that the combination indexes (CI) were found to be ≤0.4. Expectedly, VTD and etoposide started to act synergistically at 100 μM in LoVo cells. The low doses of VTD produce an antagonistic effect (CI>1) with etoposide, as previously described for other combination therapies [37]. Besides the cell viability assay, we decided to measure the apoptotic activity in the above combination therapy. The flow cytometry data revealed that combined treatment with VTD and a suboptimal dose of Etoposide (5 μM) for 24 hours significantly increased the early apoptosis in HCT-116 (FIG. 19G) cells as well as LoVo (FIG. 19H).

While we observed a promising synergism effect with a combination of VTD and a suboptimal dose of etoposide, we decided to repeat the combination therapy in the presence of a low dose of VTD and clinical doses of 5-FU and etoposide. We hypothesized that the suboptimal dose of VTD, capable of increasing UBXN2A and p53 (FIGS. 16 and 17), would potentiate the cytotoxic effect of the chemotherapeutic drugs. Cells were treated with 5-FU (5-100 μM) and etoposide (1-50 μM) along with VTD (30 and 100 μM respectively) in two different set of experiments for 24 hours. We found both the intermediate-dose of VTD (100 μM) and low dose (30 μM) of VTD significantly enhanced the 5-FU and etoposide effects on cell viability in both HCT-116 and LoVo cells (FIG. 19IL).

The analysis of our results with CalcuSyn software revealed that most of the combinations of 5-FU or etoposide with VTD have a synergistic effect on colon cancer cell viability (S7). In the case of HCT-116 cells, the strongest synergistic effect (CI=0.165 and 0.109) was found when the highest concentrations of 5-FU (75 and 100 μM) were combined with 100 μM of VTD, while the synergistic effect started at lower combinations. When VTD (30 μM) was used along with etoposide, the combined effect was synergistic (CI=0.516) at as low as 5 μM of etoposide (S7A, S7C and supplementary table 4). The same analysis for LoVo cells demonstrated that the combinations of even the smallest concentrations of 5-FU (5 μM) with 100 μM VTD (CI=0.32) and etoposide (1 μM) with 30 μM VTD (CI=0.275) had a synergistic effect on the viability of well-differentiated colon cancer cells (S7B, S7D and supplementary table 4).

VTD Potentiates the Cytotoxic Effect of Sub-Optimal Chemotherapy Against Cancer Cells Receiving Long-Term Therapy Because colon cancer cells develop resistance to chemotherapy after an initial response [38, 39], we decided to investigate whether VTD can potentiate the cytotoxic effect of 5-FU when cells receiving long-term therapy mimicking the in vivo therapy. Cells were treated with VTD for 10 days. The cell viability assay showed that HCT-116 cells only responded to a high concentration of VTD, and they were able to recover at lower doses of VTD (FIG. 20A). On the other hand, well-differentiated LoVo cells (FIG. 11 and an osteosarcoma U2OS cell line (with high perinuclear mot-2, FIG. 20D) showed a significant decrease in cell viability in a dose-dependent manner with long-term exposure to VTD. Expectedly, the SW480 (mutant p53) showed no response to longterm exposure of VTD (FIG. 20C).

Based on the significant effect of long-term exposure in LoVo and U2OS, we hypothesized that VTD could be a potential complementary strategy alongside 5-FU, an effective drug with a high rate of resistant events in colon tumors. To answer this question, we first determined the minimum concentration of 5-FU that has no effect or a very mild effect on cell viability after 10 days' exposure in three cell lines HCT-116, LoVo, and U2OS (data not shown). We performed the 10 days' treatment using a combination of a low dose of VTD (50 μM or 100 μM) plus a suboptimal dose of 5-FU (1 μM or 5 μM). The presence of VTD significantly potentiated the cytotoxic effect of the suboptimal dose of 5-FU (FIG. These results indicate that the novel anti-cancer mechanism of VTD can lower the dose of 5-FU in patients and thereby decrease side effects while postponing drug resistance. Because CD44+ stem cells are one of the major stem cancer cells in colon cancer involved in self-renewal capacity, enhanced tumor initiation, and drug resistance[41], we decided to examine whether VTD can target these specific populations. FIG. 20H-I demonstrates that intermediate-dose of VTD indeed reduces the abundance of the CD44+ cancer stem cells in U2OS and LoVo cancer cell lines.

Analysis of the Oncomine database revealed that UBXN2A expression is downregulated in some human cancers, including in patients with colon adenocarcinoma [42]. Furthermore, WB of 48 human tumor and adjacent normal tissue lysates verified a marked downregulation of UBXN2A in ~50% of patients with colon cancer (FIG. 20J). This clinical data highlights the beneficiary effect of VTD as a UBXN2A enhancer in patients with low levels of UBXN2A, and it could be used to overcome resistance to chemotherapies in patients, particularly those with over-expressed mot-2 (FIG. 20K).

Kaul et al[21] reported that overexpressed YFP-tagged p53 carboxyl-terminal peptides bind to mot-2 and lead to translocation of the endogenous p53 to the nucleus in Human osteosarcoma (U2OS) and breast carcinoma (MCF7) cells. However, we obtained no significant cell cytotoxicity in MCF7 cells in the presence of overexpressed UBXN2A. We hypothesized that, like HepG[2,7] MCF7 may partially lacked mot-2-p53 interaction in the absence of stress. The cytotoxicity assay in stressed MCF7 cells expressing UBXN2A showed no difference from results obtained without stress in MCF7-expressing UBXN2A. Unsuccessful induction of cell cytotoxicity in certain cell lines (SW480 and MCF7) by UBXN2A suggests that other factors are necessary for the execution of apoptosis induced by UBXN2A.[37] To explain the cytotoxic mechanism of UBXN2A, we first investigated UBXN2A partners in HCT-116 colon cancer cells in the presence and the absence of etoposide. This strategy allowed us to find UBXN2A partners within two different protein—protein interaction networks established in cells with and without genotoxic stress.[38] We found increased amounts of UBXN2A can bind to mot-2 and subsequently decrease the binding affinity between mot-2 and p53. A similar mechanism has been shown for the ribosomal protein S14 (RPS14) in which RPS14 unties the MDM2-p53 binding, resulting in elevated p53 level and activity.[39] These results suggest proteins such as RPS14 and UBXN2A have a protective role for p53 during cancer progression.

Small molecules can bind to the p53-binding site on the substrate binding site of mot-2 and release cytoplasmic p53 for nuclear localization, resulting in a p53-dependent apoptosis.[20,22,33] The gain and loss of functions indicated that the UBXN2A level in the cytoplasm determines nuclear translocation of p53 in colon cancer cells.

These data indicate that, in colon cancer cells, UBXN2A induces the activation of executioner caspases 3/7. Indeed, overexpression of UBXN2A in cells with dysfunctional p53 (HEK293T) and KO p53 (HCT-116 p53−/−) cells had no effect on caspase-3 activity and apoptosis, confirming that UBXN2A induces apoptosis in a p53- and caspase-3 dependent manner. In addition, there was no significant UBXN2A-dependent apoptosis in normal human colon CCD-18Co fibroblasts. Normal levels of mot-2 in noncancerous cells[42,43] and its dominant mitochondrial localization in normal cells,[44,45] as well as the lack of mot-2-p53 interaction in normal cells,[7] are likely reasons for ineffective apoptotic function of UBXN2A in normal colon and HEK293T cells. Finally, as previously discussed,[46,47] it is possible that WT-p53 proteins in colon cancer cells are more sensitive to UBXN2A upregulation than normal cells.

Protein—protein interaction experiments disclosed herein show that the SEP domain of UBXN2A binds to a section of p53's binding site on mot-2, which contains three binding amino acids used by p53: PRO442, LYS555, and ILE558.[32,33] This finding explains the possible competitive binding mechanism of UBXN2A over p53 when UBXN2A binds to mot-2. A similar competitive binding mechanism has been described for Nutlin-2 where it mimics the three key hydrophobic residues in p53 and releases p53 protein from the MDM2 E3 ubiquitin ligase.[48]

Besides induction of apoptosis, the UBXN2A-dependent p53 activation led to a significant reduction in cell migration and cell invasion in colon cancer cells. These results suggest that UBXN2A upregulation triggers a complex process involving multiple p53-dependent (both transcriptional and non-transcriptional p53 activities) and possibly p53-independent pathways acting in sequence. UBXN2A binding to p97 complex[12,15] and other UBXN2A partners found in our proteomic work strongly suggests that UBXN2A can initiate multiple biological functions in response to stress.

There is strong evidence that p53 protein levels are regulated by p53-positive regulators that inhibit p53's negative regulators during the tumor progression.[39,49, 50, 51, 52, 53, 54, 55, 56, 57, 58] While upregulation of p53's negative regulators, such as mot-2, results in poor prognosis, inhibition of these negative regulators can be a potential home defense mechanism during the initiation and progression of cancer. Collectively, these data suggest that the interaction of UBXN2A with mot-2 enables UBXN2A to enhance p53 activities and suppress tumorigenesis. Because a very high percentage of colorectal cancer expresses high levels of mot-2,[2] increased levels of UBXN2A in the cytoplasm could be a unique positive compensatory and/or adaptive mechanism to restore the function of p53 in this cancer. Our results suggest that, by following cell stress, such as that caused by genetic instability in cancer, UBXN2A can further boost p53 nuclear translocation as a home defense mechanism, resulting in an inhibition or slowing down of cancer cell proliferation (FIGS. 8g and h).

In summary, UBXN2A binds to mot-2 and releases sequestrated p53, which leads to p53-dependent apoptosis in cancer cells with high mot-2.

Here, we identify and establish UBXN2A as a colon tumor suppressor in both in vitro and in vivo models. We showed that UBXN2A enhancement leads to apoptosis at the cellular level and in live animals, resulting in tumor growth suppression. More importantly, we found induction of UBXN2A enhances the cytotoxic effects of 5-FU. Despite its anti-cancer role, we observed that 50% of patients with colon cancer have underexpressed UBXN2A in their tumors, while at the same time 75% of these patients have an overexpression of mot-2. This clinical evidence plus the anti-growth function of UBXN2A in xenograft tumors encouraged us to look for UBXN2A enhancers. Using a high-throughput drug screen, we found VTD as a potential UBXN2A enhancer. VTD is a natural plant alkaloid found in Liliaceae plants, and it has prospective anticancer properties [24-27]. Natural alkaloids, as anticancer agents, have already served as a rich reservoir for drug discovery [43, 44]. As described for other anti-cancer alkaloids [36, 45], our results indicate that VTD can mediate transcriptional activity of the UBXN2A promoter, increasing the UBXN2A protein level in vitro and in vivo and resulting in upregulation of p53 protein in both the cytoplasm and the nucleus compartment, where p53 induces apoptosis and cell death [4]. The anti-cancer function of VTD is mediated through the UBXNA-mot-2 axis. In addition, the heterozygous p53+/− and homozygous p53−/− HCT-116 cell lines show an intermediate cytotoxic effect in the presence of VTD. These latter results indicate: 1) VTD function is partially dependent on p53, and 2) VTD-dependent expression of UBXN2A and consequent binding of UBXN2A to mot-2 interferes with the other tumorigenic functions of mot-2 [2, 17, 46-50].

It has been widely accepted that activation of p53 through its tissue-specific modulators can revolutionize current anti-cancer therapies and benefit cancer patients [51]. We hypothesized that UBXN2A-dependent activation of p53 upon VTD treatment can neutralize the defense mechanisms of cancer cells against chemotherapeutic drugs, resulting in better outputs. In this study, we found that VTD-dependent activation of mot-2 has a synergetic effect with etoposide and 5-FU, two chemotherapeutic drugs with different anticancer mechanisms. Combination therapy of VTD and 5-FU or etoposide at clinical dosages as well as suboptimal doses confirmed VTD enhances the cytotoxicity of these two genotoxic agents. Significant reduction of cell viability with longterm exposure of suboptimal doses of 5-FU in the presence of low doses of VTD verified the clear synergistic effects of the two treatments combined. As previously rationalized [2], the UBXN2A-mot-2 dependent anti-cancer mechanism of VTD combined with DNA damage mechanisms triggered by conventional chemotherapy can be considered a novel treatment strategy wherein two different but interconnected pathways can selectively choose cancer cells with high levels of mot-2 and high pools of inactivated p53 versus normal cells with low mot-2 in the cytoplasm.

Recent chemotherapeutic studies confirmed traditional chemotherapies are not capable of eradicating cancer stem cells (CSCs) and fail to prevent disease relapse and metastatic dissemination, indicating that new therapies need to focus on the ability to target CSCs [52]. Our findings demonstrate that VTD targets CD-44+ CSCs. Reduction of CD-44+ cells with VTD could further explain the significant cytotoxic effect that we obtained in the long-term exposure of combined therapy with VTD and 5-FU. Our findings demonstrate that while VTD enhances the effectiveness of 5-FU-dependent DNA damage stress toward cancer cells, simultaneously VTD can target CSCs, which have tumor-initiating capacity and self-renewal features [53]. In summary, successful tumor growth suppression of xenografts in the presence of induced UBXN2A led to a drug screen to identify a natural compound capable of upregulating UBXN2A protein in both in vitro and in vivo model. We found that VTD induces apoptosis and reduces cell viability in cancer cells and CSCs in a UBXN2A-, mot-2, and partially p53-dependent manner, while normal cells dominantly remain intact. Combination therapy of VTD and standard chemotherapy showed VTD or its modified analogs can be a complementary strategy alongside suboptimal dose of chemotherapy, particularly in well-differentiated colon tumors. This study establishes the concept that the anti-cancer protein UBXN2A plays a crucial role in colon tumorigenesis, and it justifies the transition of a novel plant alkaloid compound to clinical development.

Materials and Methods

Cell Culture, Generation of Cell Lines, Chemicals, and Drug Treatments

The cell lines HEK293, HeLa, HCT-116, MCF7, and SW48, HT-29, SW620, T84, and HUVEC cells were Cell Viability, Caspase Assays, and Crystal Violet Cell Cytotoxicity Assay Cell viability in cells was measured in cells cultured in 96-well plates using Prestoblue Cell Viability reagent (Life technologies, Grand Island, NY, USA) according to the manufacturer's protocol. Caspase activity was measured at 24 h using the Apo-ONE Homogeneous Caspase-3/7 Assay (Promega, Madison, WI, USA) following the manufacturer's instructions. Caspase-3 activity was assessed using the caspase-3 colorimetric assay (BioVision, Milpitas, CA, USA) following the manufacturer's instructions. For the cytotoxicity assay, we used a technique previously described by Gillies et al and Castro-Garza et al.

Antibodies, pull down and immunoprecipitation. Table 1 lists the primary antibodies and the titers used for western blotting. Magnetic beads (Dynabeads, Invitrogen, Grand Island, NY) coupled with protein A and protein G or Dynabeads that bind histidine-tagged proteins were used for immunoprecipitation and isolation of histidine-tagged UBXN2A, respectively. Immunoprecipitation experiments were conducted as previously described.[1] Human colon tissue lysates and normal colon tissues used for immunoprecipitation were purchased from Protein Biotechnology (Ramona, CA). Human GST-tagged p53, GST-mot-2 and GST-UBXN2A recombinant proteins were provided by SignalChem (Richmond, CANADA)

TABLE 1

This table lists antibodies and their dilutions used in this study.

| Name | Manufacturer | Dilution |
| --- | --- | --- |
| Rabbit polyclonal anti-UBXN2A against #C-IQRLQKTASFRELS peptide located in the c-terminus of human UBXN2A (#NM_181713) | Pacific Immunology Corp | 1:1000 (WB) 1:500 (IHC) |
| Mouse monoclonal anti-TYG antibody [2] | Enzo life science | 1:1000 |
| Anti-p53 antibody (DO-1) | Santa Cruz biotechnology | 1:1000 |
| Anti-GRP75 (mot-2) antibody (D-9) | Santa Cruz biotechnology | 1:2000 |
| Anti-NSFLIC antibody (p47) | ABCAM | 1:1000 |
| Anti-HSC70 | Santa Cruz biotechnology | 1:5000 |
| Anti-Bax | Cell signaling | 1:200 |
| Anti-cleaved PARP (Asp214) | Cell signaling | 1:500 |
| Anti-Grp75 (mot-2) (aa 100-200 of Human Grp75) | abcam | 1:200 |
| Anti-VCP [5] antibody (p97) | ABCAM | 1:1000 |
| Mouse Anti-Human ORC-2 antibody | BD Biosciences | 1:1000 |
| Mouse anti-Glyceraldehyde-3-Phosphate Dehydrogenase antibodies (anti-GAPDH, loading controls and cytoplasmic marker). | Millipore | 1:20000 |
| IRDye 800CW Goat anti-Rabbit IgG (H + L), | LI-COR Corporate | 1:3000 | obtained from the ATCC (American Type Culture Collection). Normal colon fibroblasts (CCD-18Co) and SW480 cancer cells were a generous gift of Dr Susanne Talcott (Texas A&M University). The HCT-116 p53+/+ and HCT-116 p53−/− were purchased from GRCF Cell Center, Johns Hopkins University. All cells were grown in the recommended media, supplemented with 10% fetal bovine serum and penicillin/streptomycin.

Assessment of Apoptosis

Apoptosis in cells was assessed using an Annexin V Apoptosis Detection Kit (BD Pharmingen, San Jose, CA, USA) analyzed by using a BD Accuri C6 flow cytometer according to the manufacturer's instructions.

Cell Culture, Generation of Cell Lines, Chemicals, and Drug Treatments.

The cell line HEK293, HeLa, HCT-116, MCF7, and SW48, SW620, T84 and HUVEC cells were obtained from the ATCC (American Type Culture Collection). Normal colon fibroblasts (CCD-18Co) and SW480 cells were a generous gift of Dr. Susanne Talcott (Texas A&M University). The HCT116 p53+/+ and HCT116 p53−/− were purchased from GRCF Cell Center, Johns Hopkins University. All cells were grown in the recommended media, supplemented with 10% fetal bovine serum and penicillin/streptomycin. The $(His)_6$-TYG-tagged or GFP-tagged human UBXN2A in pcDNA3.1Z+ (Invitrogen) and pAcGFP1-C1 (Clontech, Mountain View, CA) expression vector and a negative expression control vector were used for both transient and stable transfection using the Neon electrotransfection system (Life technologies, Grand Island, NY). Optimized amounts of plasmid DNA and cells and recommended protocols that varied pulse voltage, pulse width and pulse number allowed us to have minimum 80% transfection efficiency in examined cells using the Neon system. We found that the electroporation method was not the ideal method to transfect CCD-118Co fibroblast cells with GFP-empty or GFP-UBXN2A plasmids. We conducted the transfection in FIG. 5 for CCD-118Co using Lipofectamine™ 2000 (Invitrogen). To enhance the transfection efficiency in CCD-118Co, we used a method described by Zhang et al. 3 Additionally, the transfection mixture was serum-free, since fibroblasts cells give better transfection efficiency in the absence of serum. This transfection strategy significantly decreases apoptotic cells generated by the transfection procedure.

Human GIPZ UBXN2A-based lentivirus, purchased from Open Biosystems (part of Thermo Scientific), was used to deliver and express shRNA against UBXN2A in HCT-116 cells. Experiments showed that clones I (#V2LHS_210742) and II (#V2LHS_212292) of the lentiviral-based shRNAs can efficiently silence endogenous UBXN2A. A scrambled shRNA construct was used as the control. The GFP-p53 plasmid was a generous gift of Dr. Zhenkun Lou (Mayo Medical School, Mayo Clinic, Rochester, MN). Etoposide and Staurosporine were purchased from Sigma (St. Louis, MO).

Iodixanol Gradient Analysis, Yeast-Two Hybrid and Immunoblot Analysis.

Ultracentrifuge gradient fractionation was performed as previously described.[1] To determine the binding sites used by UBXN2A for binding to mot-2, one-on-one two-hybrid analyses were conducted. The vectors containing the yeast GAL4 binding domain (pGBKT7, Clontech), with UBX2A or its truncated forms were individually cotransformed into yeast AH109 with a vector containing the GAL4 activation domain (pGAD10) fused with mot-2 or its truncated forms. Positive interactions were detected and analyzed as described previously.[1] Nuclear and cytoplasmic fractions were prepared from the cells using the NE-PER Nuclear and Cytoplasmic Extraction Reagents (Thermo Fisher Scientific, Rockford, IL) according to the manufacturer's instructions. Protein concentrations were determined by BCA assay (Thermo Fisher Scientific). Proteins were then separated on 4-20% SDS-PAGE for subsequent Western blot (Life Technologies) analysis with the appropriate antibodies.

RNA Isolation, Cloning and qRT-PCR.

Total RNA was extracted by using RNeasy (QIAGEN, Valencia, CA) according to the manufacturer's instructions. Human UBXN2A and mot-2 cDNAs were generated from total RNA using Super-script III (Life Technologies) according to the manufacturer's instructions. Wild-types and truncated forms of human UBXN2A and mot-2 were generated by PCR (primer sequences and PCR conditions are available upon request) with required restriction sites for cloning into the destination vectors. The qRT-PCR experiments were conducted the Genomics Core of the Division of Biomedical Sciences in the University of South Dakota using an Agilent Bioanalyzer (Agilent Technologies, Inc. Santa Clara, CA).

Assessment of Apoptosis.

HCT-116 or SW48 were transfected with GFP empty vector or GFP-UBXN2A using the Neon electrotransfection system (HCT-116 and SW48) or lipofectamin 2000 (CCD-118-Co), achieving around 80% transfection efficiency. Apoptosis in cells was assessed using an Annexin V Apoptosis Detection Kit (BD Pharmingen, San Jose, CA) analyzed by a BD Accuri C6 flow cytometer according to the manufacturer's instructions. In each individual experiment, GFP expressing cells were first gated and then plotted versus Annexin V positive cells. 10,000 gated events were collected per sample. An apoptotic inducer, staurosporine (Sigma), was used as a positive control in all experiments.

Cell Viability and Caspase Assays.

Cell viability in cells was measured in cells cultured in 96-well plates using Prestoblue™ Cell Viability reagent (Life Technologies) according to the manufacturer's protocol. Caspase activity was measured at 24 hours using the Apo-ONE Homogeneous Caspase-3/7 Assay (Promega, Madison, WI) following the manufacturer's instructions. Briefly, 48 hours after transfection, Caspase-3/7 activity was measured in a microplate reader (Perkin Elmer Victor X2, Waltham, MA) at excitation wavelength 488 nm and emission wavelength 520 nm. Caspase-3 activity was assessed using the caspase-3 colorimetric assay (Milpitas, CA), following the manufacturer's instructions. In brief, $2 \times 10^6$ cells were collected (HEK293T or HCT-116), and the cellular pellet was lysed in cell lysis buffer 24 hours after transfection with empty vector or UBXN2A. Caspase-3 activity was measured by using a spectrophotometer at 405 nm.

Crystal Violate Cell Cytotoxicity Assay.

We used a technique previously described by Gillies et al and Castro-Garza et al.[4,5] Briefly, $1 \times 10^4$ cells were transfected with GFP-empty or GFP-UBXN2A using electroporation and then they were seeded onto 6 well plates. After 48 hours, cells were washed with PBS, fixed and stained with crystal violate (sigma) and the absorbed dye was resolubilized with methanol containing 0.1% SDS (0.3 ml per well). Dye solution was transferred to 96-well plates and read absorbance at 595 nm using a microplate reader. In one set of experiments, MCF7 cells were first transfected and we added 5 □M etoposide after 24 hours. Stressed cells were fixe 24 hours after etoposide. The average number of absorbance was plotted for empty vector versus UBXN2A in examined cells.

Cell Migration and Invasion Assays.

HCT-116 empty vector and HCT-116 UBXN2A-expressing cells (300,000 cells/well) were suspended in 0.5 ml serum-free medium and seeded in the inner well (insert) of a cell culture insert (BD Falcon™ cell culture insert, 12 well, 8.0 micron pore size, San Jose, CA) for the migration assay and a Matrigel coated cell culture insert (BD BioCoat BD Matrigel™ invasion chamber, 24 well plate, 8.0 micron pore size) for the invasion assay. In the outer well, 1.5 ml 10% serum-containing medium was added. The cells were incubated at 37° C. After 24 hours, the serum-free medium was removed and the inner side of the insert membrane was wiped off using cotton swabs. The insert was then fixed with 70% methanol for 5 minutes and stained with 0.005% crystal violet solution for 10 minutes at room temperature. The insert was further washed with distilled water until all color was removed and, finally, air dried. The membrane of the insert was removed and mounted on a glass slide. Cells that migrated/invaded through the membrane were calculated by counting five random fields at 20× magnification using an inverted microscope (Olympus, Center Valley, PA). More details can be found in the following references:[6,7.]

Microscopic Study.

HCT-116 cells were transiently transfected with GFP-tagged UBXN2A, GFP-p53, or GFP-empty. Expression of GFP was heterogeneous among individual cells, as evidenced by foci of cells with relatively greater fluorescence. These live HCT-116 cells were imaged for the characteristics of apoptosis using a Zeiss Axiovert 200 inverted microscope. Microscopic analysis was done on the same cultures at 24, 48, and 72 hours. The percentage of detachment of transfected cells induced by GFP-fusion proteins was analyzed at the indicated times using AxioVision Software. Cell detachment from the plate induced by GFP-p53 was used as a positive control. GFP-empty transfected cells, which retained a morphology similar to uninfected cells, were used as a negative control. Using an Olympus FluoView 1000 laser scanning confocal microscope, characteristic morphology of apoptosis induced in the presence of GFP-UBXN2A, GFP-p53, and GFP-empty was also examined in paraformaldehyde fixed cells stained by DAPI. The predominant signature of apoptosis (chromatin condensation and formation of apoptotic bodies) was analyzed in GFP-expressing cells 24 hours after transfection.

DNA Fragmentation Assay.

As previously described by Nassar et al.8, HCT-116 and LoVo cells (1×105) were transiently transfected with GFP-empty or GFP-UBXN2A for 48 h. DNA was extracted with Wizard® SV Genomic DNA Purification kit (Promega). Extracted DNA was analyzed by electrophoresis using 1.0% agarose gel. DNA fragments were visualized under ultraviolet light. As it has been previously described9, 10, both HCT-116 and LoVo expressing UBXN2A showed a large molecular weight DNA fragments, although the responsible nuclease(s) has not been recognized indicating the early stage of DNA fragmentation initiated with apoptosis. This experiment was repeated twice.

Xenograft Models in Nude Mice.

Immunodeficient (athymic nude-Foxn1nu) female mice at 6 to 8 weeks of age (~23 g in weight) were purchased from Harlan (Indianapolis, IN). Transfected HCT-116 cells expressing $(His)_6$-TYG-tagged UBXN2A or $(His)_6$-TYG-tagged empty vector were selected with Zeocin (100 Kg/ml) for 2 days and expression of $(His)_6$-TYG-tagged UBXN2A proteins were confirmed using Anti-TYG antibodies. HCT-116 cells suspensions of $7 \times 10^6$ in 200 μl of free-FBS media were injected subcutaneously into one side of the lower flanks nude mice, and the same amount of un-transfected cells were injected into the opposite side. 12 mice with the right injections were divided into three groups, including a blank control group, an empty vector group, and a UBXN2A group (N=4 for empty and UBXN2A expressing cells). The tumor diameters (in $mm^3$) were measured with a digital caliper every other day and tumor volumes were calculated using the following formula: $[(W)2 \times L]/2$.[11] Thirty days after injection, all mice were sacrificed and tumors xenografts were quickly removed and snap-frozen in liquid nitrogen or fixed in 10% formalin and sectioned for immunohistochemistry. Western blot was used to detect the protein expressions of $(His)_6$-tagged UBXN2A in xenograft tumors after tumor dissection. We observed a variability of $(His)_6$-tagged UBXN2A expression in dissected tumors. To have an accurate correlation between the rate of tumor growth and the level of UBXN2A expression, we chose 3 positive mice expressing the highest level of $(His)_6$-tagged UBXN2A (data not shown). The tumor growth of these three UBXN2A tumors with their control group counterparts (empty and HCT-116) were subjected for statistical analyzes. Statistical significance was determined with the two-way ANOVA with the Bonferroni post hoc test using Prism 6 Software. Each data point is the mean tumor growth on the indicated day and error bars show the standard error.

Terminal deoxynucleotidyl transferase dUTP nick end labeling and ki67 (1:200, Vector Laboratories, Burlingame, CA) immunostaining were performed on 10 □M paraffin embedded tumor sections as previously described[12] using an in situ cell death detection kit, TMR red (Roche Applied Science, Pleasanton, CA) and Alexa Fluor 488-conjugated secondary antibody (Life Technologies) for signal detection. For negative controls, sections were only incubated with secondary antibodies (ki67 sections) or before proceeding to the TUNEL staining. In addition we used a section of a mouse lymph node as a positive control for our ki67 staining (data not shown). Proliferation was exclusively evaluated in sections with dense tumor cell mass, displaying similar cell density between empty and UBXN2A tumor xenografts.

Densitometric Quantification of Western Blot Bands.

Digitalized western blot bands were quantified by measuring pixel numbers with an automated digitizing system (UN-Scan-it gel, version 6.1). The total measured pixels of each band were normalized to the corresponding loading control.

Mot-2 and UBXN2A Detection by Protein Microarray:

The expression of mot-2, UBXN2A, and actin (for normalization) in normal and tumor tissues were determined according to the manufacturer's instructions (Protein Biotechnologies, CA, USA). The complete list of patients and their tumors are provided in supplementary table 1 and 2. Cell culture, chemicals, and drug treatments: Cells were purchased from American Type Culture Collection (VA, USA) and they were grown in the recommended medium. Veratridine, Veratrine, etoposide, 5-Fluorouracil and staurosporine were purchased from Sigma (MO, USA).

Antibodies and Immunoblotting Analysis

Nuclear and cytoplasmic fractions were prepared from the cells using NE-PER Nuclear and Cytoplasmic Extraction Reagents (Pierce, IL, USA) according to the manufacturer's instructions. Protein concentrations were determined by BCA assay followed by SDSPAGE and WB analysis with the appropriate antibodies (Supplementary Table S3).

High-Throughput Drug Screening

A cell-based screen was conducted in search of compounds that induce the expression of the UBXN2A gene. The 3.9K base of DNA upstream from the UBXN2A gene on human chromosome 2, including endogenous promoters and necessary enhancers as well as untranslated exon 1, was cloned into MCS-mGL.1, a Gaussia luciferase vector, and transiently transfected into HCT-116 colon cancer cells, with empty MCS-mGL.1 for background expression. This cell line was used to screen over 1800 FDA (Food and Drug Administration) approved drugs, synthetic compounds, and natural products (Xactagen). A glow luciferase activity assay was conducted in triplicate followed by semi-quantitative RT-PCR and WB analysis for UBXN2A, p47 (negative control), or GAPDH± Veratrine or its purified form VTD.

MTT Cell Viability Assay

An MTT (3[4, 5-dimethylthiazol-2-yl]-2, 5-diphenyltetrazolium bromide) assay was performed to measure the viability of cells. Briefly, cells were seeded at a density of 10×103 cells per well in phenol-red free growth media. After 24 hours, cells were treated with various concentrations of VTD±5-FU or etoposide. After incubation, an MTT dye was added to the cells for 2-4 hours. The absorbance of samples was measured at 630 nm using an EXL808 absorption spectrophotometer (Biotek, Winooski). The viability of cells was calculated as % of control. Cell detachment and clonogenic survival assays were conducted as previously described [4]. Early apoptosis, caspase-3, cleaved PARP and Sytox Red (Life Technology, NY, USA) were measured by the Accuri C6 flow cytometer system (BD Pharmingen, MD, USA).[54]

Xenograft Models in Nude Mice

1×107 Tet-on HCT-116 cells expressing GFP-empty or GFP-UBXN2A were injected into 6 to 8 weeks of age nude female mice [athymic nude-Foxn1nu, Harlan (IN, USA)] by subcutaneous injection. The animals with palpable tumors (~5 mm3) were then divided into two groups and fed with a standard diet (controls, n=5) or a Dox-containing diet (625 mg/kg, n=5). Of the control, one mouse was removed from the experiment due to a tumor size of >20 mm at 25 days, and we had a total of 9 mice at day 40 with 18 tumors (one GFP-empty and one GFP UBXN2A per mouse). Tumor volumes were determined as previously described [4].

Statistical Analysis of Data

Unless indicated otherwise, at least three biological repeats were performed for all the cell culture experiments. Statistical values were analyzed with either the Student's t test or by one-way ANOVA and Tukey multiple comparison post hoc tests, when appropriate. The means were compared considering a P-value of ≤0.05 as a significant difference (mean±S.E.). Data presented in FIGS. 1d and and8d8d were analyzed by GraphPad Prism VI software (GraphPad Software, La Jolla, CA, USA), and statistical significance was determined with the two-way ANOVA with the Bonferroni post hoc test. Error bars in FIGS. 1d and and8d8d represent S.E.M.

Figure Legends

FIG. 1 Cytotoxicity of UBXN2A in colon cancer cells with WT-p53. (a) HCT-116 cells were seeded at 30 000 cells per plate. Cells were transfected with GFP-empty vector, GFP-p53, and GFP-UBXN2A using the Neon transfection system (see Materials and Methods). Many GFP-UBXN2A cells were detached after the first 24 h. As GFP expression reached a maximum level after 24 h, cell detachment was studied after 24. 24, 48, and 72 h after transient transfection, detached cells were removed. Cell detachment was monitored using a Zeiss motorized inverted microscope and measuring the number of adherent live cells (green) using AxioVision software. The numbers of remaining cells were calculated in same five fields under the microscope for each experiment at 24, 48, and 72 h. The data from cell counting show a significant reduction of adherent cells in the presence of p53 or UBX2A in comparison with the empty vector after 72 h. These results suggest the UBXN2A-induced cell detachment due to apoptosis is comparable to that of p53. (b, c) In another set of experiments, HCT-116 cells transiently transfected with GFP-empty, GFP-p53, and GFP-UBXN2A were fixed and stained with DAPI. After 24 h, fluorescent microscopy observation demonstrates typical apoptotic morphology including condensation of the nuclear material (arrowheads) and formation of apoptotic bodies (arrows) when cells express p53 or UBXN2A (b). The bar chart represents the total number of the apoptotic cells counted in five fields for each groups after 24 h. Significant differences between different groups means and control value are indicated by ***P<0.001 (c). Scale bar=50 μm. (d) A cytotoxicity test with the crystal violet staining method was developed to determine cell viability in cancer cell lines transfected with GFP-UBXN2A. The Neon transfection system provides high efficiency of transfection (80-90%) and viability (90%) when electroporation parameters (voltage, pulse width, and number of pulses) are optimized for each individual cell line. Statistically significant cytotoxicity induced by UBXN2A was confirmed in HCT-116, LoVo, and HT-29 cell lines, while UBXN2A overexpression had no induction of cytotoxicity in SW480 cells (mutant p53) and MCF7 (caspase 3 deficient) breast cancer cells with and without suboptimal stress (Eto: etoposide 5 μM). Each value represents mean±S.E. of at least three independent experiments, and each experiment was performed in triplicate (*P<0.05).

Figure 2:
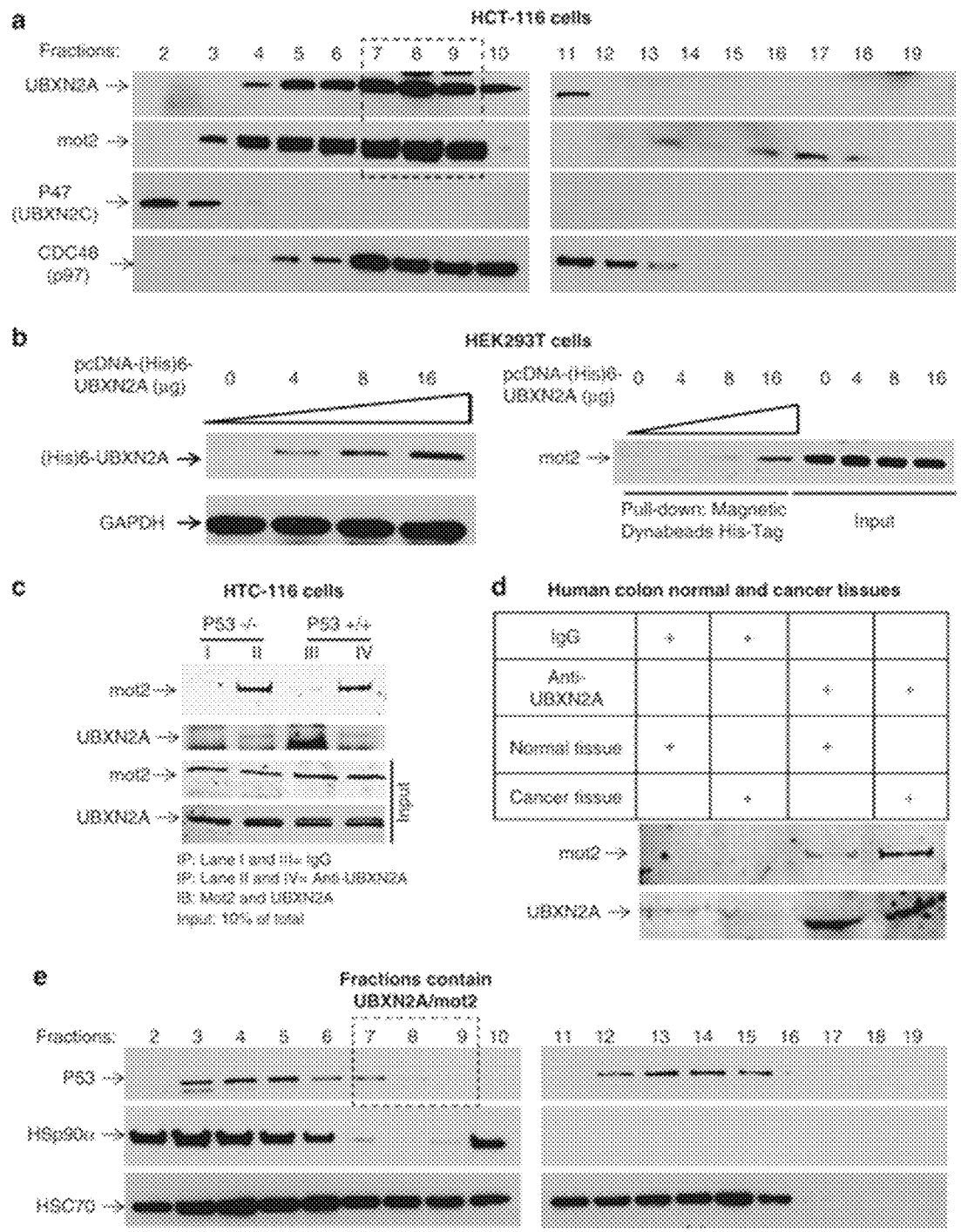
FIG. 2 shows UBXN2A interacts with mot-2.

FIG. 2 UBXN2A interacts with mot-2. (a) HCT-116 cells were treated with etoposide (50 μM) for 24 h and cytoplasmic fractions were prepared. Samples were subjected to the iodixanol gradient centrifugation. The collected fractions (20 total) were analyzed by WB using the indicated antibodies. In HCT-116 cells, co-sedimentation of endogenous UBXN2A and mot-2 was predominantly observed in fractions 7-9 (black box). In contrast, P47 (UBXN2C) did not show co-sedimentation with mot-2, supporting a selective interaction between mot-2 and UBXN2A. In addition, UBXN2A showed co-sedimentation with its known partner, the protein p97 (CDC48). (b) HEK293T cells were transfected with increased amounts of pcDNA-(His)$_6$-TYG-tagged UBXN2A. After 24 h, cell lysates were incubated with 50 μl magnetic Dynabeads (His)$_6$-Tag. UBXN2A pulls down endogenous mot-2 in a dose-dependent manner in HEK293T cells. (c, d) Using magnetic Dynabeads protein A, endogenous UBXN2A bound to immobilized anti-UBXN2A antibodies pulls down endogenous mot-2 in HCT-116 (knockout derivative (p53−/−) and wild-type (p53+/+)) colon cancer cells as well as mot-2 in human colon cancer tissues. We particularly observed pulled down mot-2 with tumors in d (Lane 4 versus 3). (e) Fractions shown in a were probed with anti-p53, HSP90a, and HSC70 antibodies. As expected, only some p53 proteins co-sediment with mot-2 (fractions 3-5). Instead, p53 showed strong co-sedimentation with fractions enriched in HSP90a, a known stabilizer of p53, in fractions 3-7. Fractions containing UBXN2A and mot-2 (a, fractions 7-9) have a low level of p53 (black box). As expected, another population of p53 proteins co-sedimented with HSC70, a known p53 regulator, in fractions 12-15. These results suggest that two distinct mot-2-containing complexes exist, one that sediments with p53 (fractions 3-5) and one that sediments with UBXN2A (fractions 7-9).

Figure 3:
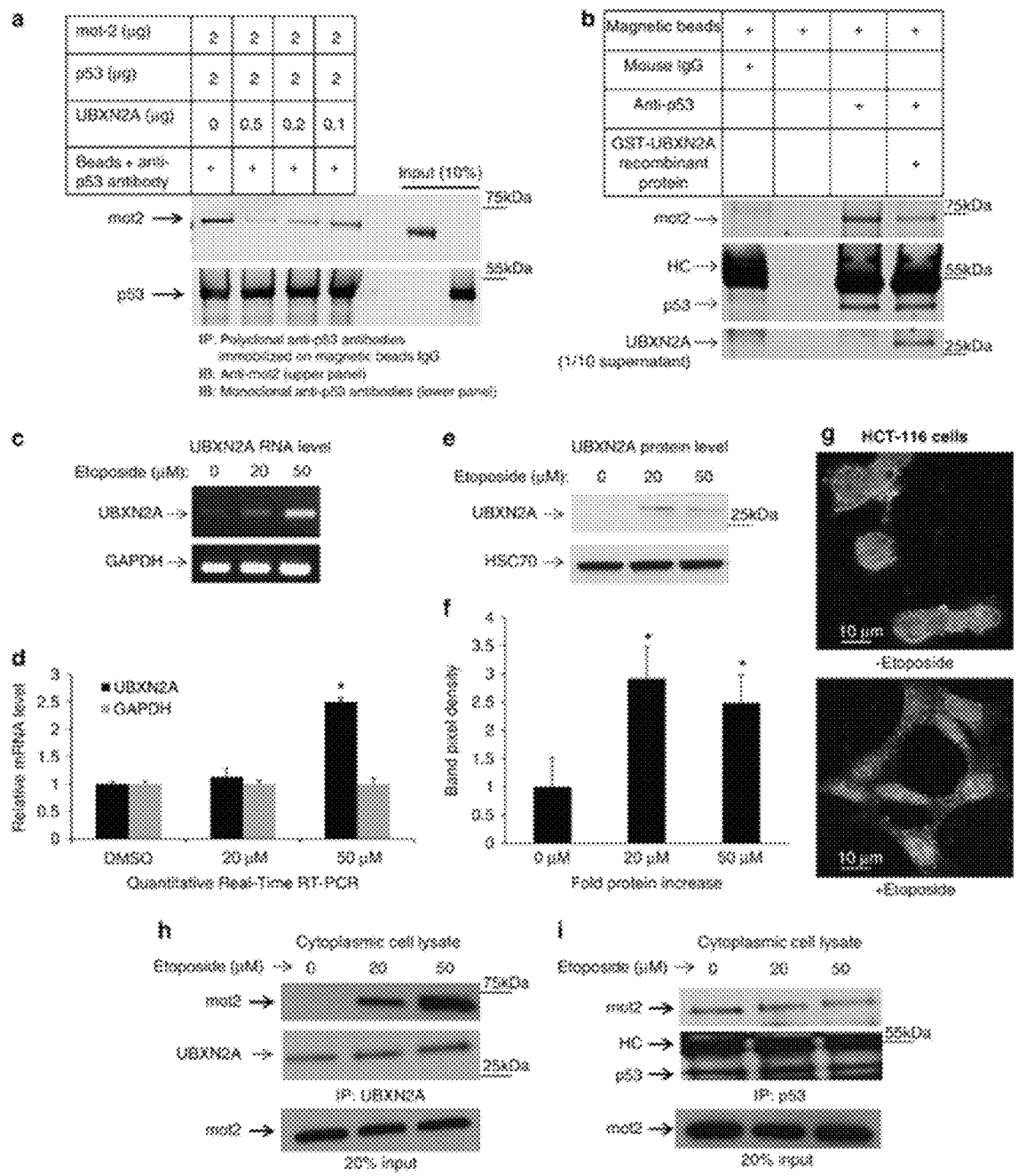
FIG. 3 shows UBXN2A and p53 compete for binding to mot-2.

FIG. 3 UBXN2A and p53 compete for binding to mot-2. (a) We investigated whether UBXN2A can decrease the association of p53 with mot-2 using an in vitro binding competition assay. First, recombinant human GST-p53 proteins bound to anti-p53 antibodies-IgG magnetic beads were incubated with human GST-mot-2 protein and increasing concentrations of human GST-UBXN2A recombinant proteins. Mot-2 proteins were eluted from the beads and analyzed by western blotting using an anti-mot-2 antibody. The same membrane was re-probed for p53 (lower panel) to show equivalent p53 in each IP. (b) The in vitro competition assay was further confirmed when the human GST-UBXN2A fusion proteins were incubated with cytosolic fractions enriched with mot-2 and p53 proteins (fractions 3-5, FIG. 2e) of HCT-116 cells. The level of recombinant protein provided an ~2.5:1 ratio of UBXN2A to endogenous mot-2. Cell lysates with and without UBXN2A were incubated with anti-p53 antibodies immobilized on magnetic Dynabeads protein G (Lanes 3 and 4). Beads with mouse IgG or beads alone were control groups in this experiment (lane 1 and 2). Western blotting showed that UBXN2A caused displacement of p53 binding from mot-2. These data support that UBXN2A and p53 compete for the mot-2. (c, d) A semiquantitative RT-PCR protocol (SuperScript III One-Step RT-PCR system) and quantitative real-time RT-PCR (d) showed etoposide enhances transcription of UBXN2A in HCT-116 cells. (e, f) At 24 h post-etoposide treatment (20 and 50 μM), total cell lysates were obtained, 50 μg of protein was loaded in each lane, and the resulting blots were probed with an anti-UBXN2A antibody. UBXN2A's signal was normalized with the HSC70 signal (loading control). Together, these data confirmed UBXN2A expression is upregulated at the mRNA and protein levels upon genotoxic stress (P<0.05, n=3). DMSO was used as vehicle control. (g) Immunofluorescent staining reveals that UBXN2A shows a juxtanuclear staining characteristic of the ER/Golgi apparatus in the absence of etoposide. However, UBXN2A showed striking punctate cytoplasmic staining when HCT-116 cells incubated with etoposide (50 µM) for 24 h, suggesting a dynamic change in UBXN2A functional linkage networks in response to genotoxic stress. (h, i) The results presented in (f) indicate significant upregulation of UBXN2A in the cytoplasm with 20 and 50 µM etoposide after 24 h incubation. To verify whether this upregulated endogenous UBXN2A causes displacement of p53, we conducted a series of IP experiments. (h) Cytoplasmic lysates from e treated with no etoposide or 20 and 50 µM were subjected to IP using anti-UBXN2A (h) or anti-p53 (i) antibodies immobilized on magnetic IgG beads. Samples were resolved by 4-20% gradient SDS-PAGE and detected by WB using the indicated antibodies. The HC indicate the heavy immunoglobulin band. WB results indicate that UBXN2A binds to mot-2 in a etoposide dose-dependent manner, while the amount of mot-2 associated with p53 decreases simultaneously.

FIG. 4 shows UBXN2A induces p53 nuclear translocation in HCT-116 colon cancer cells. HCT-116 cells were transfected with the indicated amount of $(His)_6$-TYG-tagged UBXN2A plasmid. Cytoplasmic (a) and nuclear (c) fractions were subjected to WB. The cell expression pattern of tagged UBXN2A proteins mimics the function of endogenous UBXN2A in the cytoplasm upon etoposide exposure illustrated in FIG. 3. (b, d) UBXN2A is capable of significantly increasing the nuclear level of p53 in a dose-dependent manner (fold increase, n=11, *P<0.05). (e, f) HCT-116 cells were incubated with different concentrations of etoposide for 24 h. Cytoplasmic and nuclear protein lysates were prepared and subjected to western blot analysis to monitor p53 and UBXN2A protein levels. GAPDH and Orc-2 antibodies were used as cytoplasmic and nuclear markers, respectively. (g) HCT-116 cells were transfected with empty vector or $(His)_6$-TYG-tagged UBXN2A plasmid. After 48 h, total cell lysates were prepared followed by WB using indicated antibodies. GAPDH was used as loading control. (h, i) Two lentiviral-based shRNAs were able to efficiently decrease the level of endogenous UBXN2A in HCT-116 cells treated for 24 h with 50 µM etoposide. WB of the nuclear cell lysates showed a significant decrease in nuclear p53 (i, n=8, *P<0.05). Taken together, these gain- and loss-of-function approaches in HCT-116 cells indicate that UBXN2A facilitates nuclear localization of transcriptionally active p53.

Figure 5:
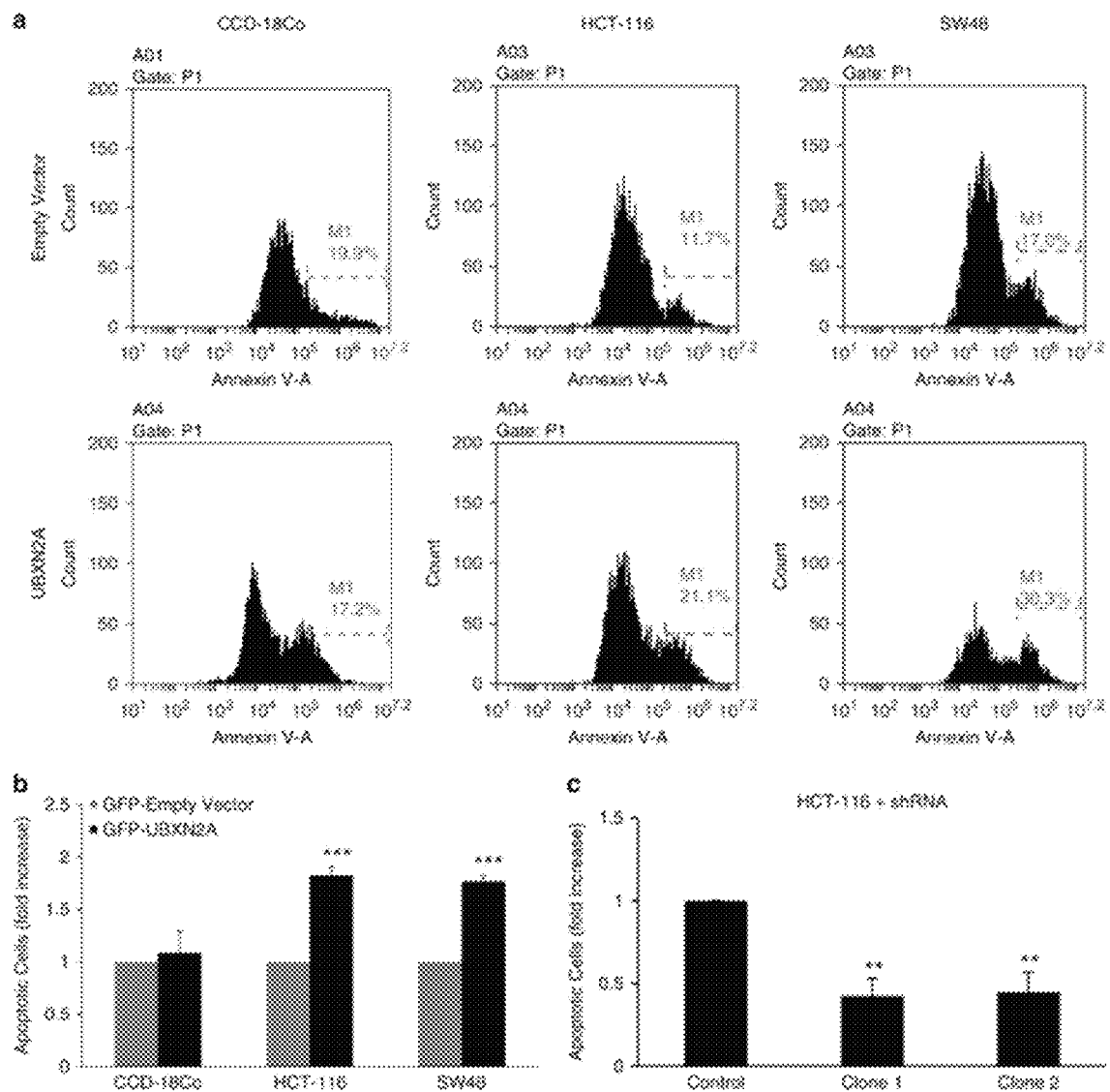
FIG. 5 shows UBXN2A overexpression induces apoptosis in colon cancer cell lines but not in normal, non-transformed cells.

FIG. 5 shows UBXN2A overexpression induces apoptosis in colon cancer cell lines but not in normal, non-transformed cells. CCD-18Co, HCT-116, and SW48 were transfected with GFP-empty or GFP-UBXN2A. 48 h after transfection, cells were stained with Annexin V and early apoptosis was determined using flow cytometry as described in Materials and Methods. (a) Representative flow-cytometry analysis data from an Annexin V assay. The histograms show a comparison of the distribution of Annexin V positive cells (M1) after transient transfection of cells with GFP-empty vector or GFP-UBXN2A. The data were gated on GFP-UBXN2A positive cells prior to Annexin V analysis. (b) UBXN2A expression for 48 h significantly increased the number of apoptotic cells in HCT-116 and SW48 cell lines, while CCD-18Co normal colon cells were unaffected. (c) HCT-116 were transfected with scrambled shRNA or shRNA against UBXN2A (clone I and II). 48 h after silencing, superconfluent cultures of HCT-116 were analyzed by Annexin V assay using flow cytometry. Expression of GFP containing shRNA against UBXN2A resulted in 50% less apoptosis in comparison with cells transfected with scrambled shRNA. Values are expressed as mean (±S.E.M.) from three independent experiments (P<0.01, *P<0.001).

Figure 6:
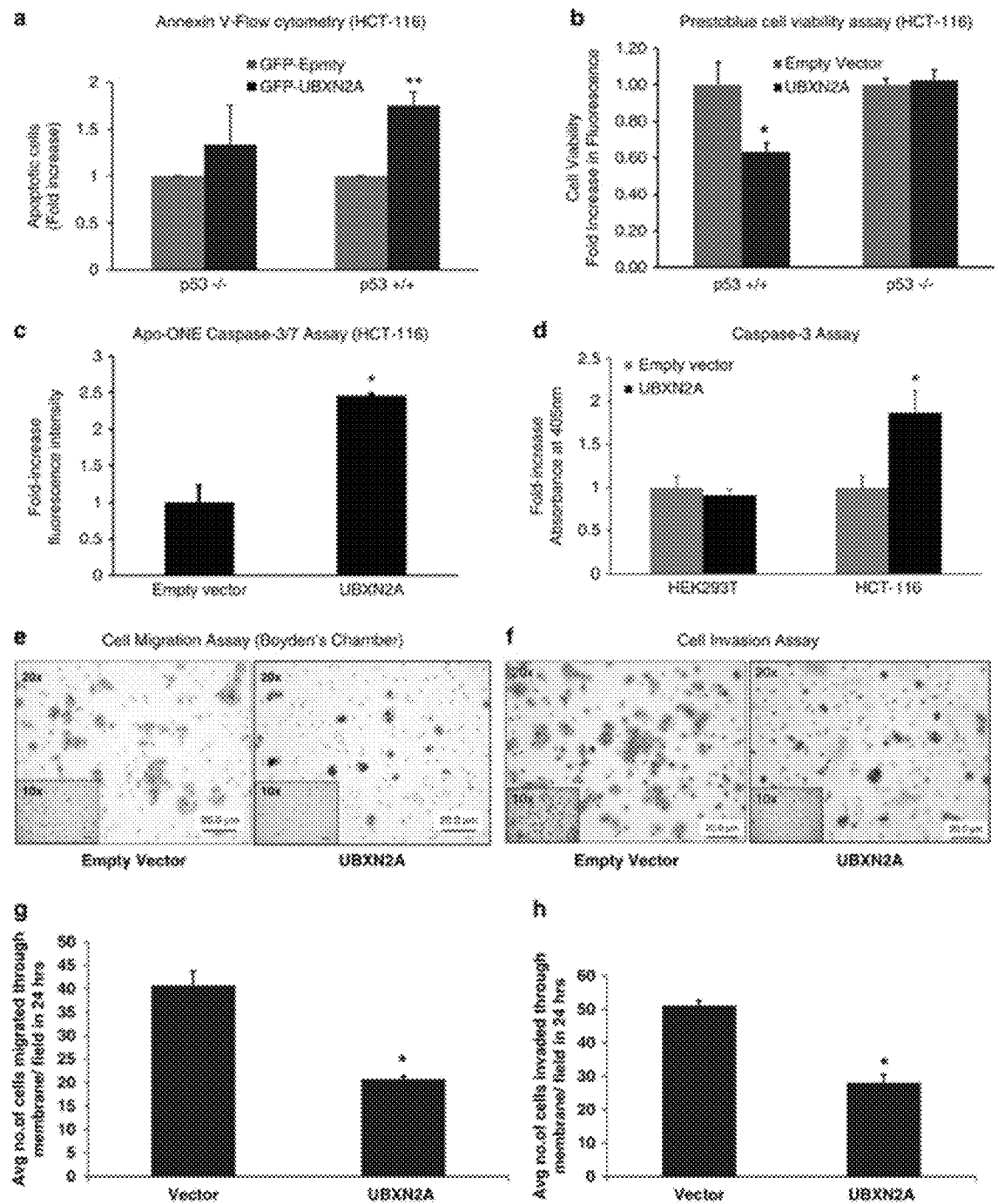
FIG. 6 shows induction of apoptosis by UBXN2A is p53 dependent and caspase-mediated in colon cancer cell lines.

FIG. 6 shows induction of apoptosis by UBXN2A is p53 dependent and caspase-mediated in colon cancer cell lines. (a, b) HCT-116 (p53+1+) or HCT-116 (p53−/−) cells were transiently transfected with GFP-empty or GFP-UBXN2A for 48 h. An Annexin V apoptosis assay (a) and Prestoblue cell viability (b) assay show that overexpression of UBXN2A leads to a significant increase in cell apoptosis (c) and reduction of cell viability (d) in HCT-116 with WT-p53 (p53+/+). There was not a significant change between GFP-empty and GFP-UBXN2A in p53-KO cells (*P<0.05, **P<0.01). (c) HCT-116 cells were transfected with GFP-empty or GFP-UBXN2A. After 48 h, levels of caspase-3/7 activity (an indicator of apoptosis) in cells expressing GFP-empty or GFP-UBXN2A were measured using the Apo-ONE homogeneous caspase-3/7 assay kit. Results show 2.5-fold increase in caspase-3/7 activity in cells expressing GFP-UBXN2A relative to GFP-empty cells (*P<0.05). (d) Noncancerous HEK293T cells and HCT-116 colon cancer cell lines were transiently transfected with $(His)_6$-TYG-empty or $(His)_6$-TYG-UBXN2A vectors. A caspase-3 colorimetric assay revealed that UBXN2A exclusively activates caspase-3 only in cancer cells (*P<0.05). (e) Cell migration assay. HCT-116 empty-vector and HCT-116 UBXN2A-expressing cells (300 000 cells/well) were suspended in serum-free medium and seeded on cell culture inserts. After 24 h, cells that migrated through the membrane were stained and photographed at ×20 magnification. Cells were counted in five different fields and the average was plotted. (f) Invasion assay. HCT-116 empty vector and HCT-116 UBXN2A-expressing cells (300 000 cells/well) were suspended in serum-free medium and seeded on Matrigel coated inserts. After 24 h, cells that invaded through the Matrigel insert were stained and photographed at ×20 magnification. Cells were counted in five different fields, and the average was plotted. A representative micrograph (e, f) and quantification (g, h) of invaded cells are shown. The data show a significant decrease in migration/invasion of UBXN2A-expressing cells. For all the assays, data represent the mean of three experiments (Mean±S.E.M.) *P<0.05.

Figure 7:
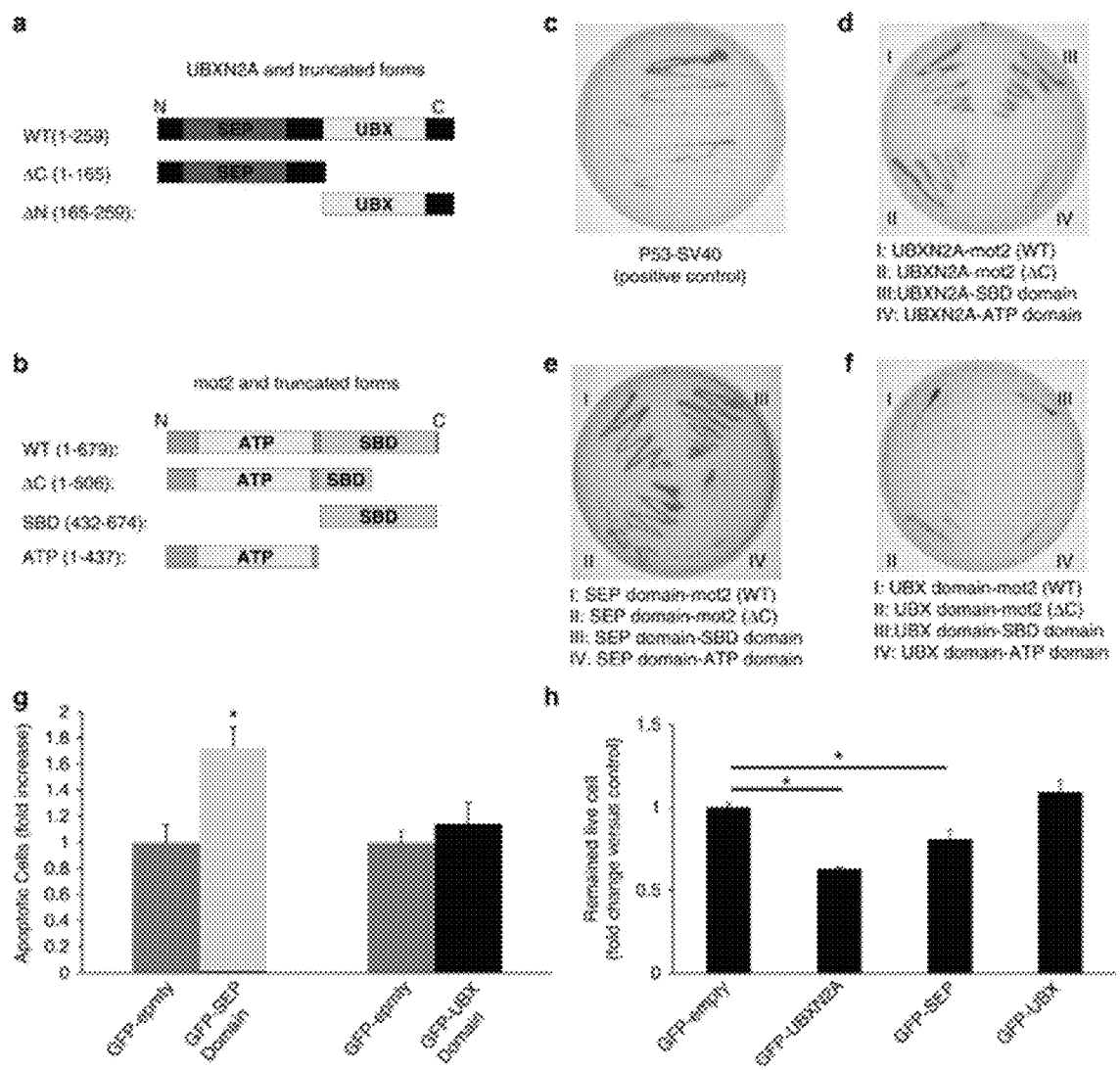
FIG. 7 shows interaction of the SEP domain of UBXN2A with the p53-binding site (SBD domain) of mot-2 is sufficient to induce apoptosis.

FIG. 7 shows the interaction of the SEP domain of UBXN2A with the p53-binding site (SBD domain) of mot-2 is sufficient to induce apoptosis. (a, b) Schematic diagram of UBXN2A and mot-2 protein domain structures. (c-f) Comprehensive mapping of protein—protein interaction sites by Y2H method using α-galactosidase activity and nutritional selection verified that (i) WT-UBXN2A interacts with WT-mot-2, (ii) the SEP domain of UBXN2A is sufficient to interact with WT-mot-2, and (iii) a partial section of p53 binding site on the SBD domain of mot-2 (aa:438-506) is sufficient for binding to WT-UBXN2A. (g) An apoptosis assay using Annexin V staining followed by flow cytometry analysis confirmed that only the SEP domain of UBXN2A is required to induce apoptosis in HCT-116 cells, similar to full WT-UBXN2A. No increase in apoptosis was seen with the GFP-UBX domain. (h) HCT-116 cells were transfected with GFP-UBXN2A (WT) or its truncated forms (GFP-SEP or GFP-UBX domains). After 48 h, cells were subjected to a crystal violet cell cytotoxicity assay. Counting the remaining colonies showed both WT-UBXN2A and GFP-SEP domains significantly induce cell cytotoxicity (*P<0.05, n=3)

Figure 8:
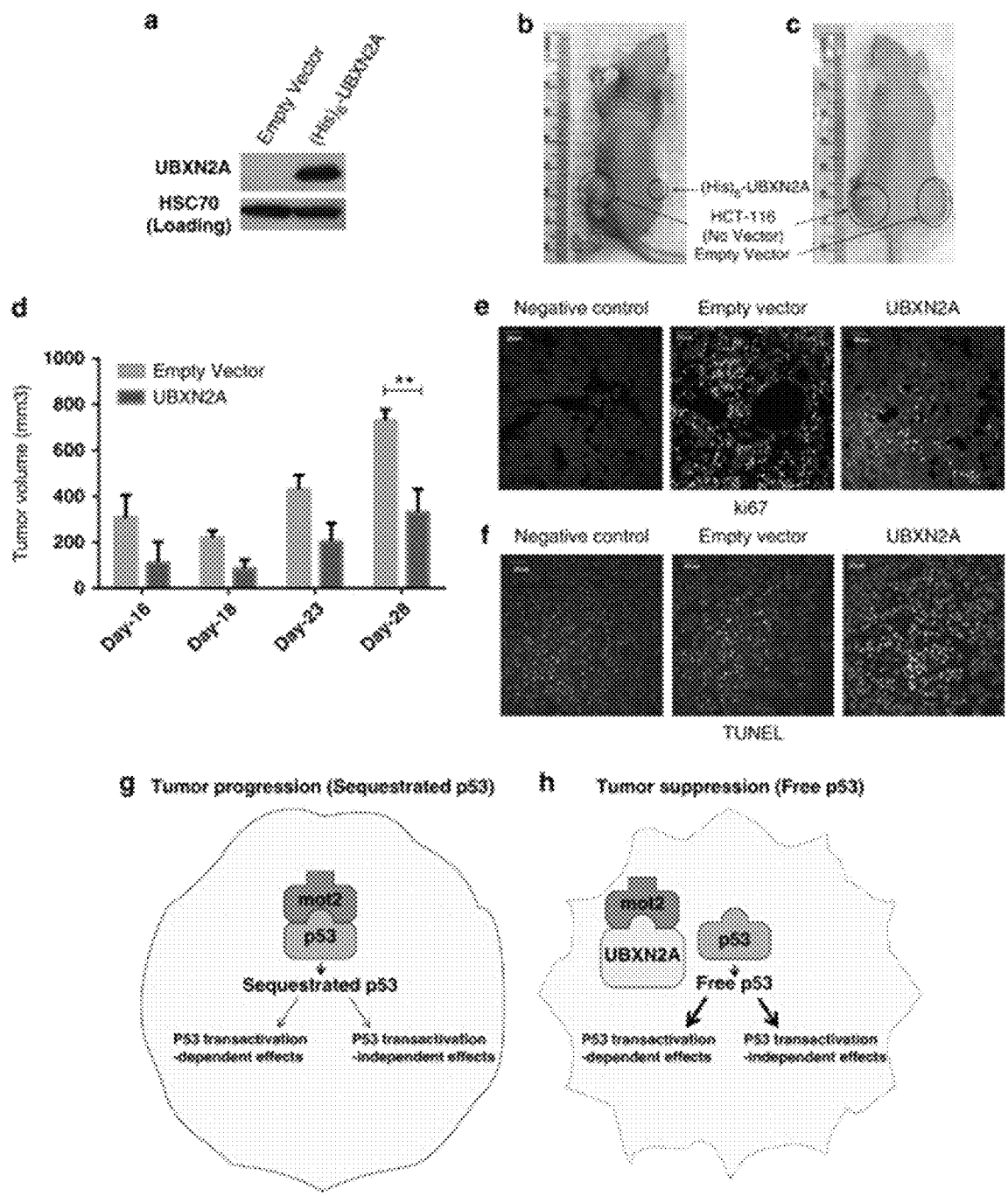
FIG. 8 shows overexpression of UBXN2A markedly reduces tumor growth in xenograft model.

FIG. 8 shows overexpression of UBXN2A markedly reduces tumor growth in xenograft model. $7 \times 10^6$ HCT-116 cells (p53+/+) expressing (His) 6-TYG-UBXN2A or an empty vector were subcutaneously injected into nude mice in the lower flank (see Materials and Methods). (a) shows a portion of the transfected HCT-116 cells that was lysed and analyzed by western blotting for expression verification. (b, c) are representative of xenografts experiments with detectable expression of $(His)_6$-tagged UBXN2A proteins. (d) Tumor growth was monitored on the indicated days. Results represent growth rate of tumor volume on the indicated days. Statistical comparisons were done by ANOVA followed by the Bonferroni post hoc test using the GraphPad Prism 6 (**P<0.01, n=3). Each data point is the mean tumor growth on the indicated day, and error bars show the standard error of mean. (e, f) Tumor tissue sections were subjected to immunohistochemical assay for Ki67 expression and TUNEL staining Alexa-488 labeling of ki67 and 570 red fluorescent labeling for TUNEL assay were captured with the Olympus scanning confocal microscope using the Fluoview 1000 software. Negative controls were processed sections in the absence of primary antibody (e) or before proceeding to the TUNEL staining (f). Scale bar=20 (g, h) The working model of p53 regulation by UBXN2A. Mot-2 protein has been shown to interact with p53 and inhibit its activation in cancerous cells. Upregulation of UBXN2A impedes mot-2-mediated inactivation of p53, which leads to the activation of p53.

Figure 9:
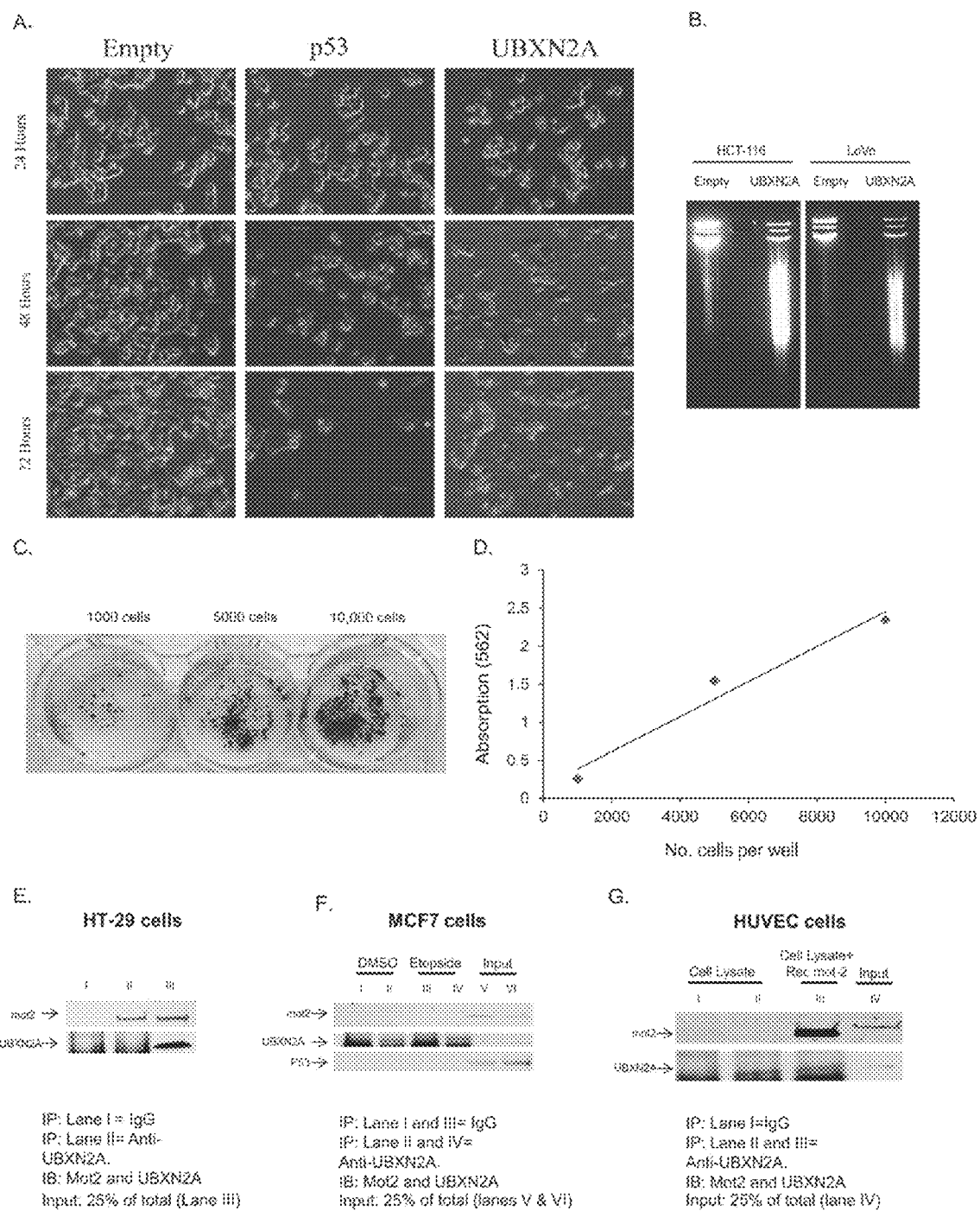
FIG. 9: shows UBXN2A expression induces cell cytotoxicity and DNA fragmentation in colon cancer cells

FIG. 9 shows UBXN2A expression induces cell cytotoxicity and DNA fragmentation in colon cancer cells. Panel A. Representative phase contrast images of HCT-116 cells expressing GFP-empty, GFP-p53, and GFP-UBXN2A. After 24, 48, and 72 hours, the detached cells were removed and the remained cells were calculated by counting in five random fields using the Axiovert 200 M inverted microscope and AxioVision software. Scale bar for all the images, 100 μm. Panel B. HCT-116 and LoVo colon cancer cells were transiently transfected with GFP-empty or GFP-UBXN2A. After 48 hours, internucleosomal DNA degradation was determined by agarose gel electrophoresis. Panel C-D. Cell viability by staining with crystal violet and reading absorbance at 562 nm (A562 nm) using different number of HCT-116 WT cells plated for 7 days. Results on the HCT-116 cells follow a linear function. Panel E-G: Cell lysates of HT-29, MCF7 (with and without suboptimal stress) and HUVEC (normal endothelial cells) were subjected to immunoprecipitation. Using magnetic Dynabeads protein G, endogenous UBXN2A bound to immobilized anti-UBXN2A antibodies pulls down endogenous mot-2 in HT-29 cells. In contrast, endogenous UBXN2A did not pull down endogenous mot-2 in MCF7 (with and without suboptimal stress). The immunoprecipitation experiments with anti-UBXN2A antibody using HUVEC lysates were conducted in the absence and the presence of recombinant human GST-tagged mot-2 (Rec-mot-2). Immunoblotting of pulled-down proteins showed UBXN2A only pulls down recombinant mot-2 (sufficient amount of mot-2) and not the endogenous mot-2 expresses in normal HUVEC cells.

Figure 10:
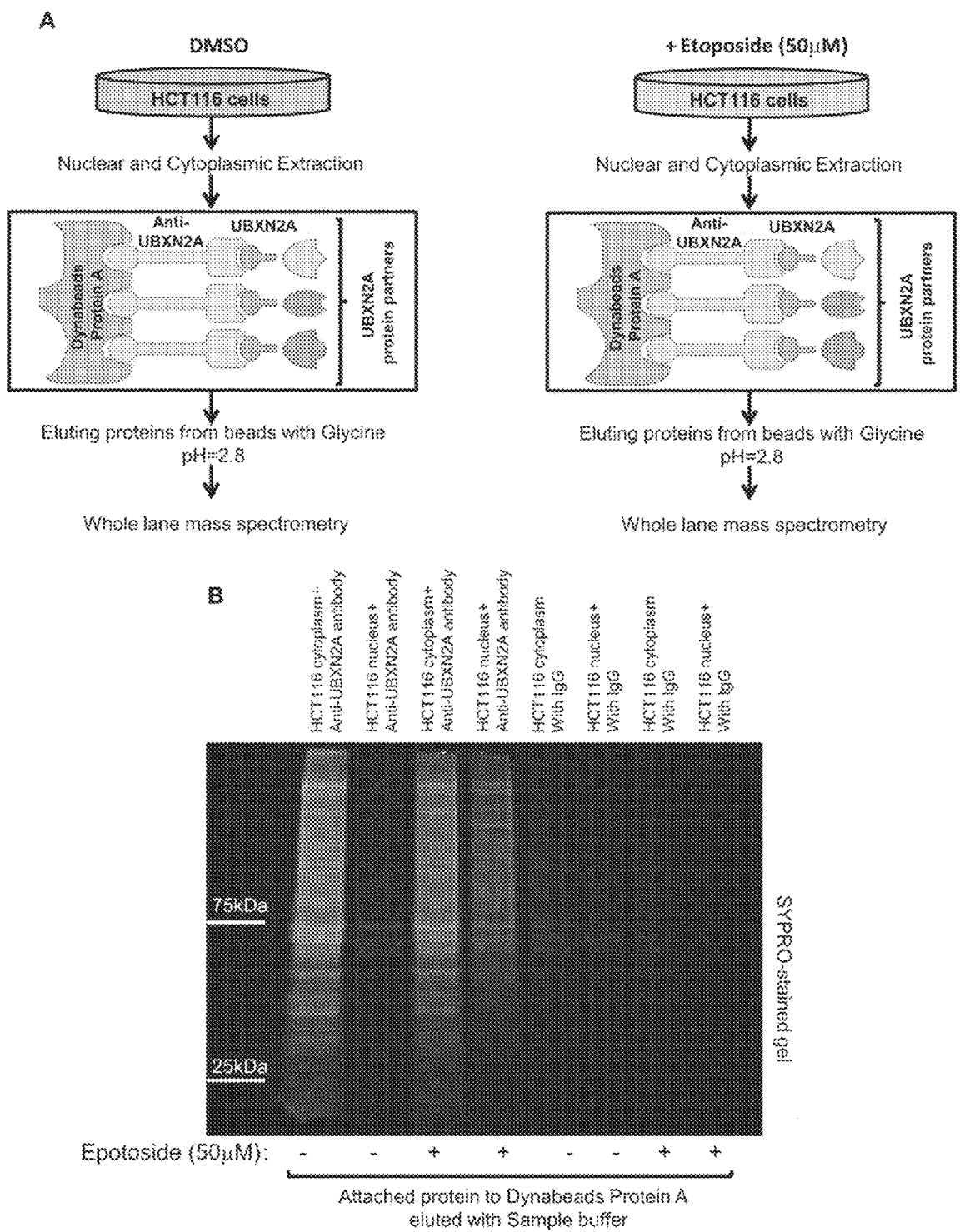
FIG. 10 shows the proteomics approach utilized to identify UBXN2A interacting proteins.
Figure 11:
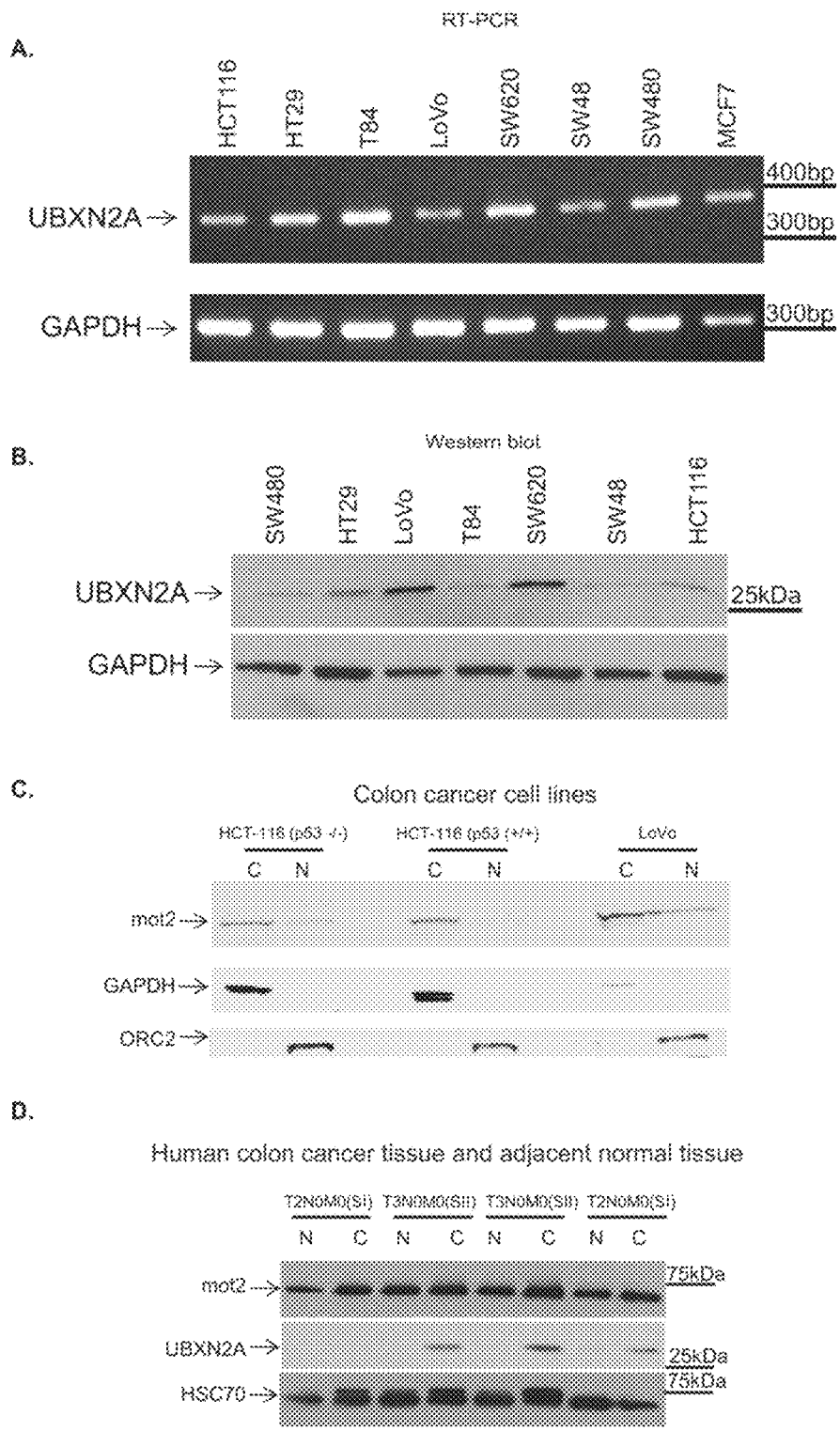
FIG. 11 shows transcript and protein expression of UBXN2A and mot-2 in colon cancer cell lines and human colon tumors.

FIG. 10: A proteomics approach to identify UBXN2A interacting proteins. Panel A. A schematic diagram showing a proteomic approach for finding UBXN2A's partners in the presence or absence of etoposide. 24 hours after incubation with DMSO or etoposide (50 μM), cytoplasmic and nuclear fractions were incubated with 10 μg anti-UBXN2A immobilized on magnetic beads. After extensive washing, the bound proteins were eluted with acidic glycine and sent for proteomic identification. Panel B shows a SYPRO ruby stained gel containing UBXN2A's partners that bound to UBXN2A on the magnetic beads. Eluted UBXN2A's partner proteins were analyzed by mass spectrometry-based proteomic approaches.[13] IgG controls were performed by incubation of Dynabead protein A magnetic beads and 10 μg of rabbit IgG. Using this approach, we identified several candidate proteins, including mot-2. Mot-2 showed a larger spectral count in the etoposide treated cells versus the control group in cytoplasmic fractions, indicating the abundance of mot-2 co-immunoprecipitated with UBXN2A upon genotoxic stress in HCT-116 cells.

FIG. 11 Transcript and protein expression of UBXN2A and mot-2 in colon cancer cell lines and human colon tumors. The RNA and protein expression levels of UBXN2A in HCT-116, HT29, LoVo, SW620, SW48, and SW480 colon cancer cell lines and the MCF7 breast cancer cell line were investigated. Panel A. First-strand cDNA was synthesized from the extracted RNA samples and 1/4 of the newly synthesized cDNA is amplified using PCR amplification method. We used the following forward and reverse primers to compare the RNA level of UBXN2A in above cell lines: UBXN2AF, (SEQ ID NO: 1) and UBXN2AR, 5'GTTGTTCAGTGGA ACAGCAGAC3' (SEQ ID NO: 2). Housekeeping gene GAPDH (RT-GAPDH Fwd, 5'-CAAC-TACATGGTTTAC ATGTTC-3' (SEQ ID NO: 3); RT-GAPDH Rev, 5'-GCCAGTGGACTCCACGAC-3' (SEQ ID NO: 4)) was used to analyze the relative expression of UBXN2A in cancer cell lines. Panel B. Cell lysates prepared from SW480, HT29, LoVo, T84, SW620, SW48, and HCT-116 were subjected to western blot analysis using anti-UBNX2A and anti-GAPDH antibodies. Panel C. Cell lysates of HCT-116 (WT-p53 or p53 –/–) cells as well as LoVo cells were subjected to indicated antibodies. Panel D. Tissue lysates of human colon tumors and their adjacent normal tissues in different stages (Tumor, node and metastasis or TNM) were subjected to WB using anti-mot-2 and anti-UBXN2A antibodies. Panel C and D illustrate the steady state levels of mot-2 and UBXN2A in a well differentiated (LoVo) and poorly differentiated (HCT-116) colon cancer cells as well as in human colon tissues.

FIG. 12: Annexin V staining and flow cytometry is a valid assay for measurement of early apoptosis. Un-transfected CCD-18Co, HCT-116, and SW48 cells were incubated with vehicle or staurosporine, a well-known inducer of apoptosis in a wide range of cell lines, for 24 hours. Subsequently, cells were stained with BD Biosciences Cy5 Annexin V and read on an Accuri C6 flow cytometer. Panel A. The histograms show a comparison of the distribution of Annexin V positive cells in un-transfected CCD-18Co, HCT-116 and SW48 cells (no gating). Panel B. The positive control, staurosporine (100 nM), was able to induce significant apoptosis in both a normal colon cell line (CCD-18Co) as well as HCT-116 and SW48 colon cancer cell lines. Panel C-D: We conducted a set of IP experiments to further confirm UBXN2A can only bind to the SBD domain and not the ATP domain. HCT-116 cells were transiently transfected with SBD domain or ATP domain of mot-2. After 36 hours, cell lysates were prepared followed by immunoprecipitation using anti-UBXN2A immobilized on magnetic protein G beads. Immunoprecipitation experiments verified UBXN2A binds to the SBD domain of mot-2 (amino acid residue 432-679) in HCT-116 cells and not the ATP domain (amino acid residue 1-437). This set of immunoprecipitation experiments verified results achieved in Y2H experiments. For panel D, we used an anti-Grp75 (mot-2) antibody from abcam (see table 1) enables to detect the N-terminus of mot-2 protein.

Figure 13:
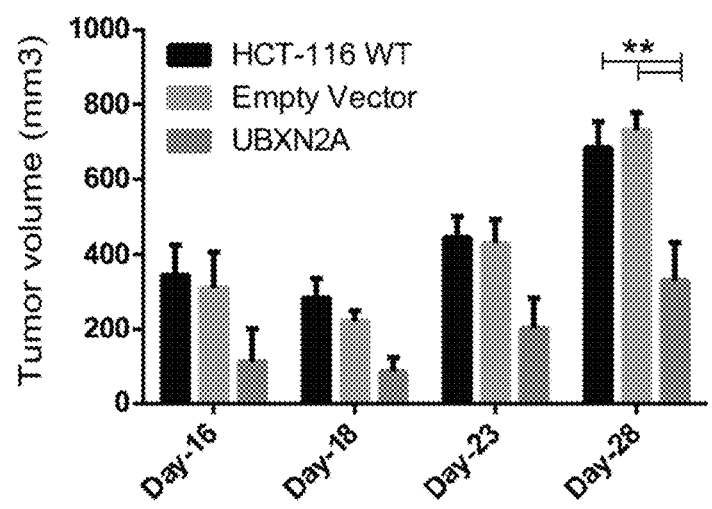
FIG. 13 shows overexpression of UBXN2A markedly reduces tumor growth in xenograft model in comparison to the untransfected cells (HCT-116 WT) and the transfected cells with empty vector.

FIG. 13: Overexpression of UBXN2A markedly reduces tumor growth in xenograft model in comparison to the untransfected cells (HCT-116 WT) and the transfected cells with empty vector. Tumor growth was monitored on the indicated days as explained in main FIG. 8. FIG. 5S shows growth rate of tumor volume±SE on the indicated days for three groups: 1) HCT-116 untransfected (HCT-116 WT), 2) HCT-116 expressing empty vector and 3) HCT-116 cells expressing (His) 6-tagged UBXN2A. Statistical comparisons indicates cells expressing (His) 6-tagged UBXN2A significantly slow tumor progression (** $P<0.01$, n=3).

Figure 14:
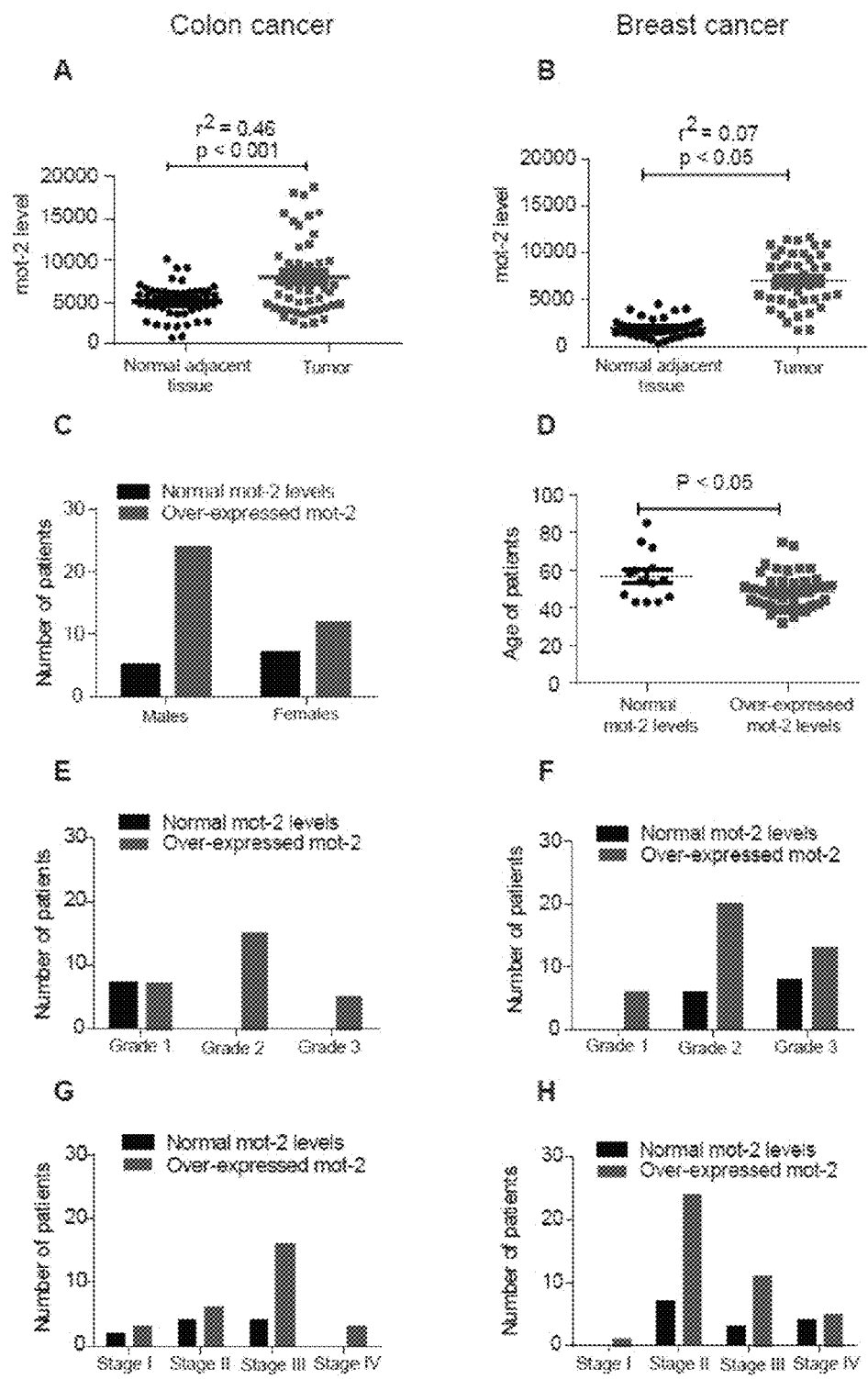
FIG. 14 shows how the heat shock protein mot-2 plays a critical role in tumorigenesis.

FIG. 14: The heat shock protein mot-2 plays a critical role in tumorigenesis. Equal amounts of tumor tissue lysates from 48 patients with colon cancer (A) and 55 patients with breast cancer (B) along with matched adjacent normal tissue lysates were probed with anti-mot-2 and anti-actin antibodies followed by quantitation and normalization of signals. (A-B) These two diagrams show densitometry-quantified signals of mot-2 expression in tumor tissue versus normal adjacent tissue. The expression of mot-2 in the tumor tissues of patients diagnosed with colon cancer (A) and breast cancer (B) was significantly higher as compared to normal tissues (Colon tumor: $R^2=0.46$ and $P<0.001$, Breast tumor: $R^2=0.07$ and $P<0.05$, correlation coefficient test for each pair of variables). (C) Overexpression of mot-2 in colon cancer is gender dependent. Higher numbers of male patients show overexpression of mot-2 as compared to female patients. (D) Overexpression of mot-2 in breast cancer is age dependent. The statistical analysis shows that a relatively higher number of young female patients showed over-expression of mot-2 levels. (E-H) Profiling of grade- and stage-dependent of tumors with colon (E and G) and breast (F and H) cancer showed that patients with mot-2 overexpression have been diagnosed with a higher grade and stage of tumors, indicating poorer survival. These clinical results confirm mot-2 as a potential target for the treatment of cancers and a promising prognostic factor.

FIG. 15: Induction of UBXN2A slows the growth of a colon cancer tumor ex vivo and in a mouse xenograft model by 50%. (A) A Tet-on regulated inducible HCT-116 colon cancer cell line was established successfully. 48 hours' incubation with Doxycycline (DOX, 10 mg/ml) induces an equal expression of GFP-empty (EMP) or GFP-UBXN2A in HCT-116 cells. Images were taken using an inverted fluorescent microscope. (B) WB showing the expression of GFP-empty and GFP-UBXN2A proteins in HCT-116 cells when treated with DOX for 48 hours. An anti-GFP antibody was used to detect the levels of GFP alone or of GFP-UBXN2A fusion proteins, while GAPDH was used as a loading control. (C) Inducible cells (GFP-EMP or GFP-UBXN2A) were treated with DOX for the indicated times. Cells were then stained with PerCP-Cy5.5 Annexin V antibody, and a total of 10,000 gated events were analyzed by flow cytometry. DOXinduced UBXN2A expression in 48 and 72 hours showed a significant increase in annexin binding in those cells. The data is shown as mean+SEM of three independent experiments in triplicate (n=3) where *$p<0.001$ using Tukey's modified student's t-test. (D) Inducible cells (GFP-EMP or GFP-UBXN2A) were treated with DOX for 48 hours, followed by staining with Alexa Fluor 546 anti-caspase-3 antibody. Cells were analyzed using flow cytometry and collected data was normalized with GFP-EMP (+DOX). The DOX-induced UBXN2A expression significantly increased caspase-3 levels (n=3, *$p<0.05$). (E) Inducible cells (GFP-EMP or GFP-UBXN2A) were treated with DOX for the indicated times. Immunofluorescence of p21 was performed. Intensity of fluorochrome signals from a confocal microscope were analyzed by the Image J (NIH, Bethesda, MD) program and plotted. The data was normalized with GFP-EMP (+DOX). The expression of UBXN2A significantly increased levels of p21 (n=100,*$p<0.001$). (FG) HCT-116 cells expressing GFP-EMP and GFP-UBXN2A under DOX were treated with 5-FU (100 μM) for 48 hours. Cells were then stained with Alexa Fluor 546 anticaspase-3 (F) or anti-cleaved PARP (G) antibodies, followed by flow cytometry analysis. The induced UBXN2A significantly enhanced 5-FU-induced increase in caspase-3 and cleaved PARP levels (n=3, *$p<0.05$). (H) Inducible HCT-116 cells were incubated with DOX and 5-FU for 48 hours, stained with Sytox Red, and then the population of dead cells was analyzed using flow cytometry. UBXN2A significantly enhanced 5-FU-induced cell death (n=3, *$p<0.05$). (I-J) $1\times10^7$ Tet-on inducible cells were injected subcutaneously into the lower flanks of nude mice. The animals with palpable tumors for early-stage tumor response were divided into two groups after injection to be fed with a standard diet (controls) or a DOX-containing diet (625 mg/kg). Tumor volumes in mm3 were determined with digital calipers by the formula Volume=(width) 2 ×length/2 every second day for 40 days. (K) Expression of GFP-empty or GFP-UBXN2A proteins in dissected xenografts confirmed successful tumor responses to DOX after 40 days. (L) Growth of tumors with and without DOX on day 40. Treatment with DOX significantly decreases tumor size and weight by more than 50%. The data is shown as mean+SEM of 9 mice (n=4 for control and n=5 for DOX) where *$p<0.05$ using Tukey's modified student's t-test.

Figure 16:
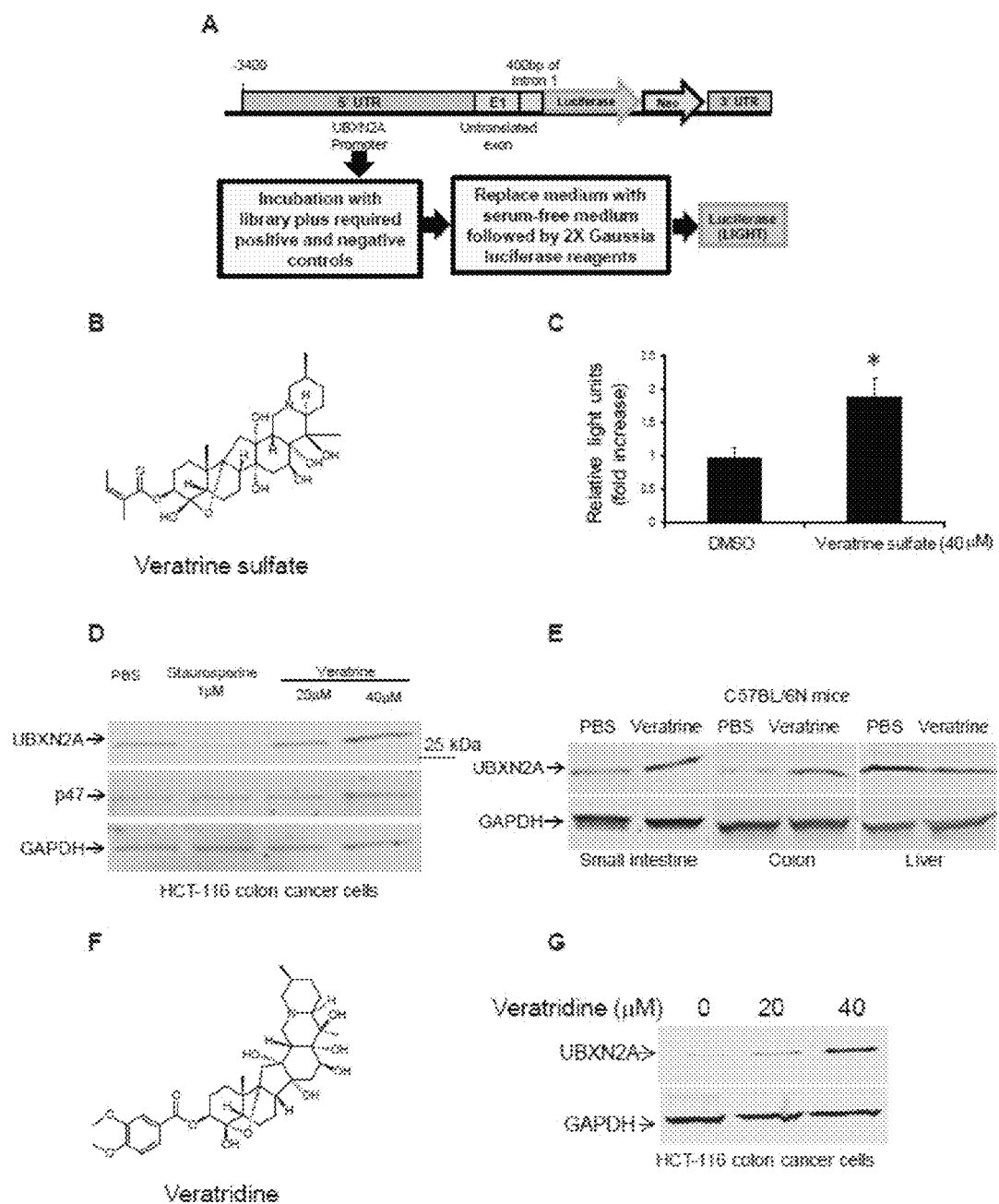
FIG. 16 shows the increase in UBXN2A level in vitro and in vivo for veratrine and its purified form VTD.

FIG. 16: Veratrine and its purified form VTD increase UBXN2A level in vitro and in vivo. (A) A cell-based screen was conducted in search of compounds that induce the expression of the UBXN2A gene. The 3.9K base of DNA upstream from the UBXN2A gene on human chromosome 2, including endogenous promoters and necessary enhancers as well as untranslated exon 1, was cloned into MCS-mGL.1, a Gaussia luciferase vector, and transiently transfected into HCT-116 colon cancer cells. We used empty MCS-mGL.1 for background expression. This cell line was used to screen over 1800 FDA (Food and Drug Administration) approved drugs, synthetic compounds, and natural products. A glow luciferase activity assay was conducted in triplicate. We found 12 potential candidates in the initial screen, which were confirmed again by the luciferase assay. (B-C) 40 μM Veratrine sulfate (an unpurified form of VTD) resulted in a ~twofold increase in luciferase activity when compared to control. (D) WB experiments showed incubation of HCT-116 with Veratrine for 24 hours leads to up-regulation of UBXN2A, while Veratrine has no effect on p47 (UBXN2C), another member of UBXD family. GAPDH was used as a loading control. Staurosporine, as an alkaloid, was used as a negative control. (E) IP injection of Veratrine (0.125 mg/kg) to C57Bl/6N mice for 28 days showed a selective upregulation of UBXN2A in small intestine and colon tissues, but no changes were observed in the liver of the same animal. (F) VTD is a naturally occurring plant alkaloid of steroidal structure, isolated from plants of the family Liliaceae. (G) HCT-116 cells were treated with VTD (20 and 40 μM) and cell lysates were subjected to WB. GAPDH was used as a loading control. VTD increases UBXN2A protein levels in a dose-dependent manner.

FIG. 17: Induction of apoptosis and in vitro cytotoxicity by VTD in a human cancer cell line with different statuses of p53 and mot-2. (A-D) Cells were treated with VTD for 24, 48, and 72 hours. After incubation, dead cells were washed off, and the remaining attached cells were calculated by counting in five random fields using the Axiovert 200 M inverted microscope and AxioVision software (cell detachment assay). The % of cells attached was calculated as % of control cells. VTD significantly decreases the % of cells attached in a dose-dependent manner in cancer cells with WTp53 (A: HCT-116, B: LoVo and C: U2OS) but not with mutant p53 (D: SW480). The data is shown as mean+SEM of three independent experiments (n=3, *p<0.05). (E-K) Cells were plated for 5 days, and the colonies of cells were treated with different concentration of VTD. The colonies of viable cells were stained with crystal violet dye and absorbance, as an index of measurement of colony forming units, was read at 562 nm (clonogenic survival assay). VTD induced a significant decrease in cell viability in a p53- and differentiation grade manner in HCT-116 poorly differentiated cells (E), HCT 116 p53+/−(F), HCT-116 p53−/− (G), LoVo well-differentiated cells (H), SW-480 (K), and two non-colon cancer cells: HepG2 (I) and U2OS (J). The data is shown as mean+SEM of three independent experiments (n=3, *p<0.05). (L) Determination of endogenous levels of mot-2, UBXN2A, HSC70, and p53 proteins in various cancer cell lines using WB. (M) HCT-116 cells were treated with VTD (10 and 30 µM) and cytoplasmic and nuclear fractions were subjected to WB. HSC70 and Orc-2 antibodies were used as cytoplasmic and nuclear markers, respectively. VTD increases p53 in both cytoplasm and nucleus compartments in a dose-dependent manner.

Figure 18:
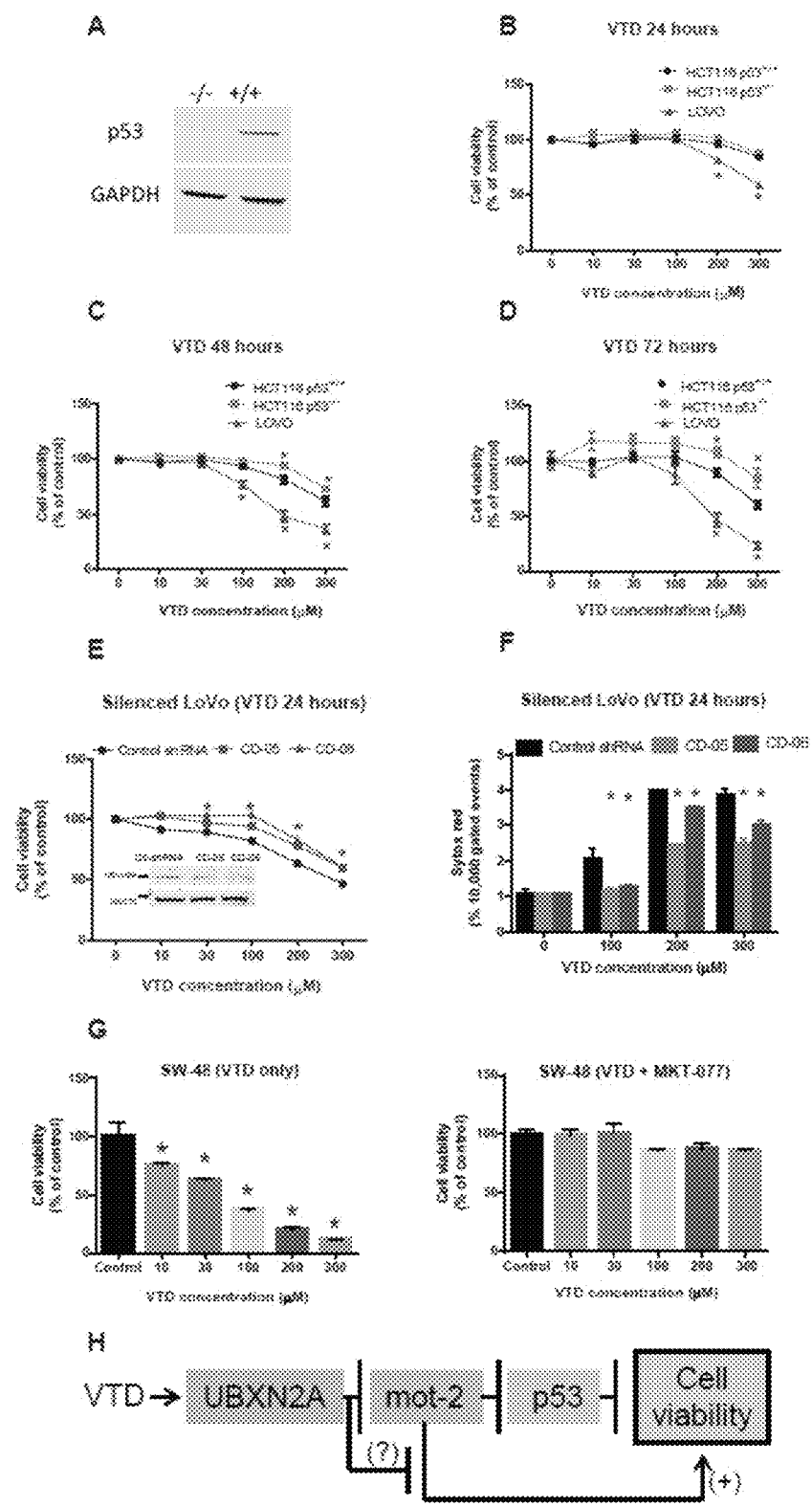
FIG. 18 shows VTD functions via the UBXN2A-mot-2-p53 axis.

FIG. 18: Veratridine (VTD) functions via the UBXN2A-mot-2-p53 axis. (A) WB confirmed the presence and the absence of p53 protein in HCT-116 p53$^{(+/+)}$ and HCT-116 p53$^{(-/-)}$ cancer cell lines, respectively. (B-D) The effect of VTD on the viability of well-differentiated (HCT-116 p53 $^{(+/+)}$ and HCT-116 p53$^{(-/-)}$ and poorly differentiated (LoVo) colon cancer cell lines was determined using an MTT assay. VTD's cytotoxic effect on all three cell lines was dose dependent in (B) 24 hours, (C) 48 hours, and (D) 72 hours. As compared to the HCT-116 p53$^{(+/+)}$ cells, HCT-116 p53 $^{(-/-)}$ cells showed more resistance to VTD's effects, whereas well-differentiated (LoVo) colon cancer cells showed the highest sensitivity to VTD. (E) LoVo cells were stably silenced for UBXN2A using a UBXN2A-shRNA along with a scrambled shRNA. Viability of UBXN2A-silenced cells was found to be significantly higher as compared to control cells upon treatment with VTD. (F) In another set of experiments, UBXN2A-silenced cells were treated with VTD (100, 200, and 300 µM) for 24 hours. Cells were then labelled with Sytox Red followed by flow cytometry analysis. Results showed silencing of UBXN2A significantly decreases cell death in response to VTD. (G) SW48 well-differentiated colon cancer cells with WT-p53 were treated with MKT-077 (5 mg/ml), an mot-2 inhibitor, along with VTD for 72 hours. A clonogenic survival assay showed VTD signifcantly decreases the colony number of SW-48. However, preincubation with MKT-077 neutralizes the cytotoxic effect of VTD. (H) This flowchart recapped the sequence of proteins which activate and function upon VTD exposure to decrease cell viability. The data is shown as mean±SEM of three independent experiments (n=3) in triplicate where *p<0.05 using Benferroni's modified student's t-test.

Figure 19:
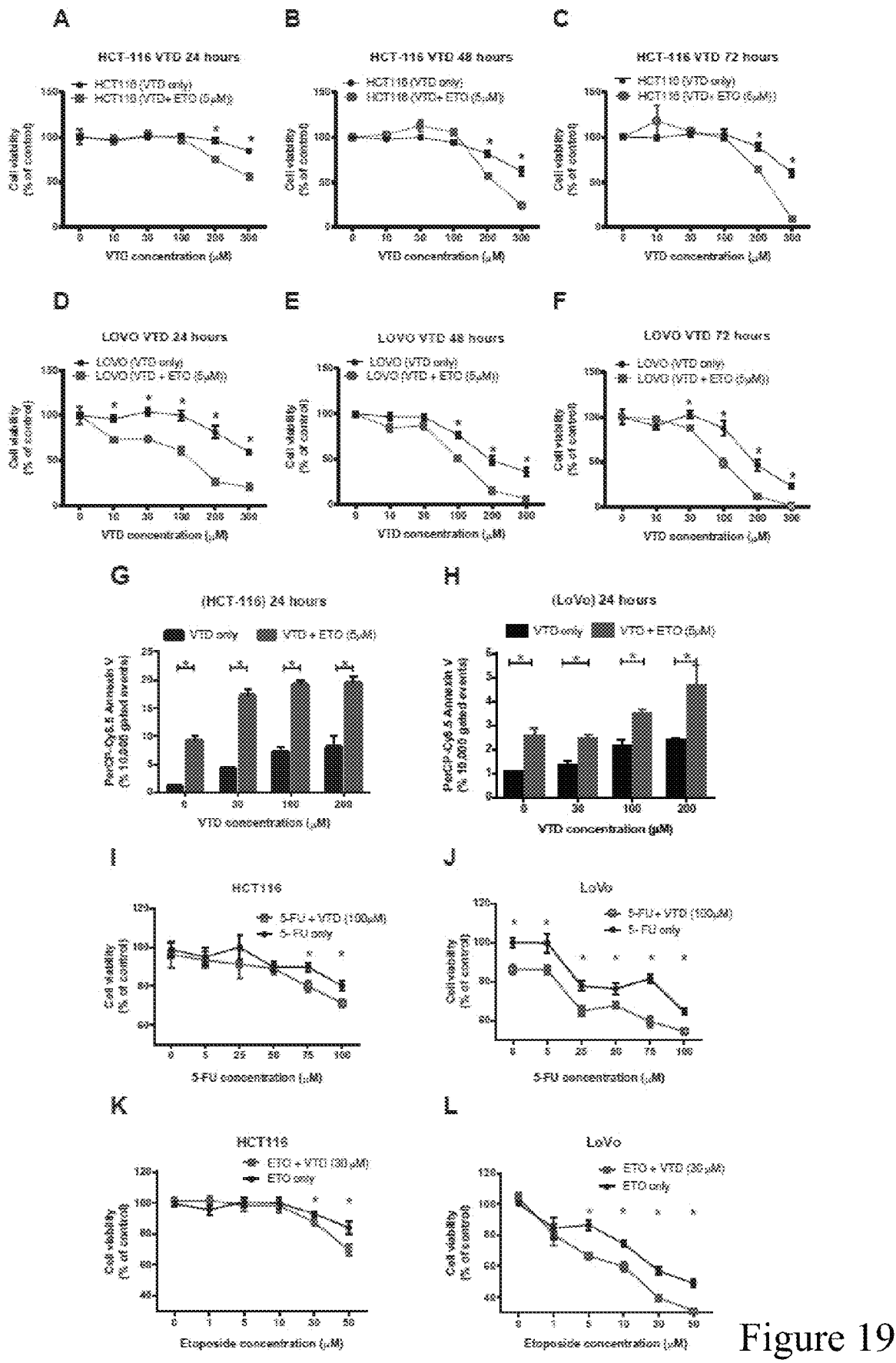
FIG. 19 shows the synergistic inhibitory effects of VTD and etoposide or 5-FU chemotherapeutic drugs on the growth of human colon cancer cells.

FIG. 19: Synergistic inhibitory effects of Veratridine (VTD) and etoposide or 5-FU chemotherapeutic drugs on the growth of human colon cancer cells. (A-H) (A-C) HCT-116 and (D-F) LoVo were treated with VTD (10-300 µM) for 24, 48, and 72 hours. A suboptimal dose of Etoposide (ETO) (511M) was added to cells for the last 24 hours only. The viability of cells was determined as % of control (untreated cells) using an MTT assay. The chemotherapeutic drug ETO significantly enhanced the VTD-induced decrease in cell viability of both poorly differentiated (HCT-116) and well-differentiated (LoVo) colon cancer cell lines in a time-dependent manner. (G-H) HCT-116 (G) and LoVo (H) cells were treated with VTD (10-200 µM) and a suboptimal dose of ETO (5 µM) for 24 hours. Cells were then stained with Annexin V apoptotic marker. ETO significantly sensitizes both poorly and well-differentiated colon cancer cells to VTD even at 30 mM. (I-L) HCT-116 and LoVo cells were treated with different doses of 5-FU (5-100 µM, I-J) and ETO (1-50 µM, K-L) along with VTD (30 µM and 100 µM respectively) for 24 hours. MTT assays showed the treatment with 5-FU and ETO with VTD decreased cell viability at much lower drug doses. Results were analyzed using CalcuSyn software to calculate the combination index (CI) to confirm and quantify the synergism observed with combination therapies (S6 and S7 and supplementary table 4). The data is shown as mean±SEM of three different experiments (n=3) where *p<0.001 using Benferroni's modified student's t-test.

Figure 20:
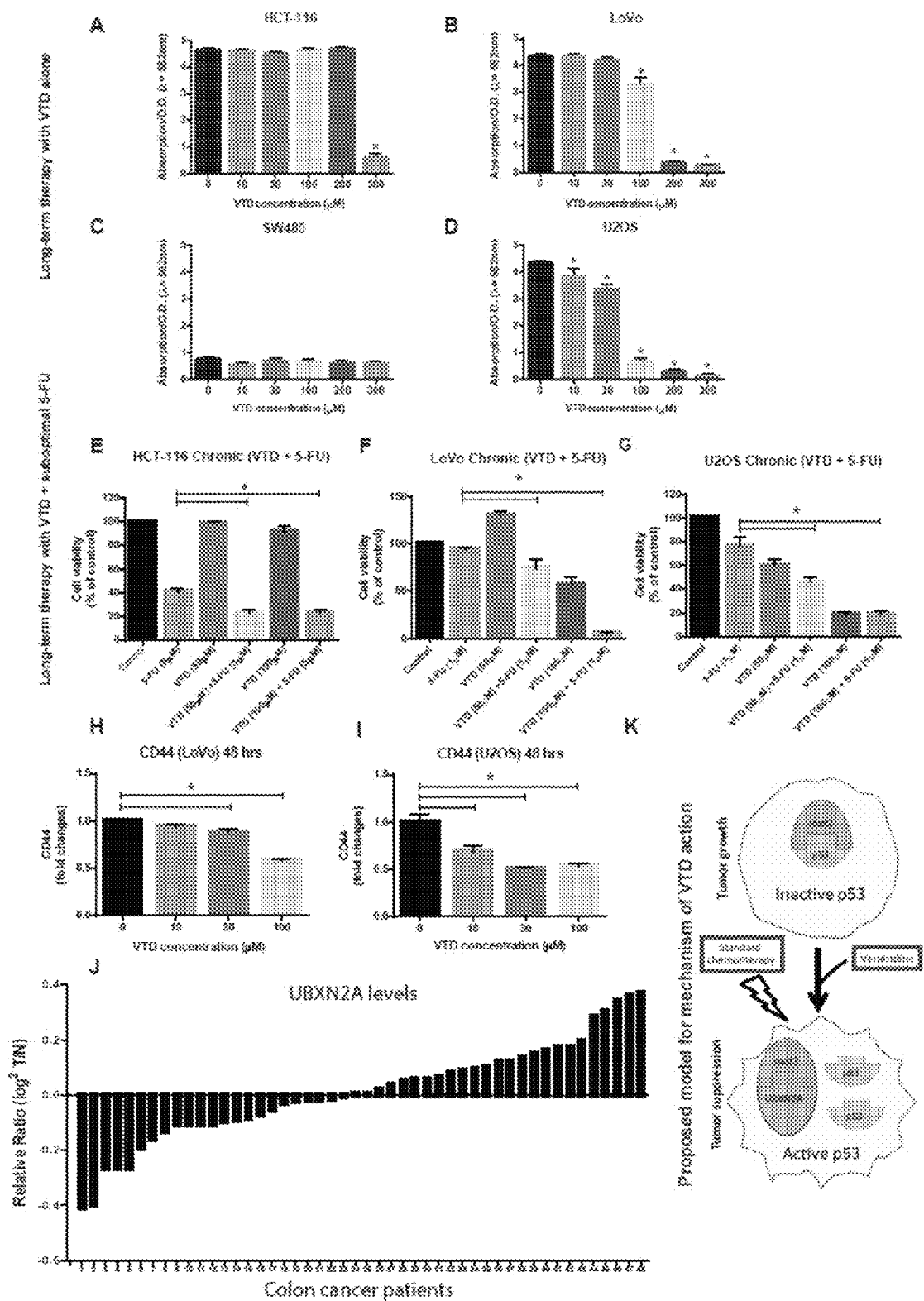
FIG. 20 shows the sensitization of colon cancer cells to a long-term suboptimal dose of 5-fluorouracil exposure when combined with VTD.

FIG. 20: Sensitization of colon cancer cells to a long-term suboptimal dose of 5-fluorouracil exposure when combined with VTD. (A-D) (A) HCT-116, (B) LoVo, (C) SW-480, and (D) U2OS were treated with VTD (10-300 µM) for 10 days. Colony formation assays showed VTD effectively reduces cell viability in a cell type-dependent manner. (E-G) (E) HCT-116, (F) LoVo, and (G) U-2OS were treated with suboptimal doses of 5-FU and VTD (50 and 100 µM) for 10 days. Clonogenic survival assays revealed an intermediate-dose of VTD significantly potentiates the standard chemotherapy used at very low dose (1-5-FU). (H-I) A series of flow cytometry assays using an antibody against the CD44 cancer stem cell marker illustrated that VTD can target CD44+ colon cancer stem cells and eventually eliminate them in a dose-dependent manner, implicating VTD as a potential cancer stem cell-targeting therapy. (J) Tumor tissue lysates from 48 patients with colon cancer along the matched adjacent normal colon tissue lysates were probed with anti-UBXN2A and anti-Actin antibodies, followed by quantitation and normalization of signals. UBXN2A expression shows a marked downregulation in ≥50% of patients with colon cancer. (I) The proposed mechanism action of VTD. VTD increases the expression of UBXN2A, which releases the p53 from mot-2's sequestration and, together with standard chemotherapy, can cause an effective tumor suppression.

PEG & PLE/PLE Modified of VTD Enhances UBXN2A

Figure 21:
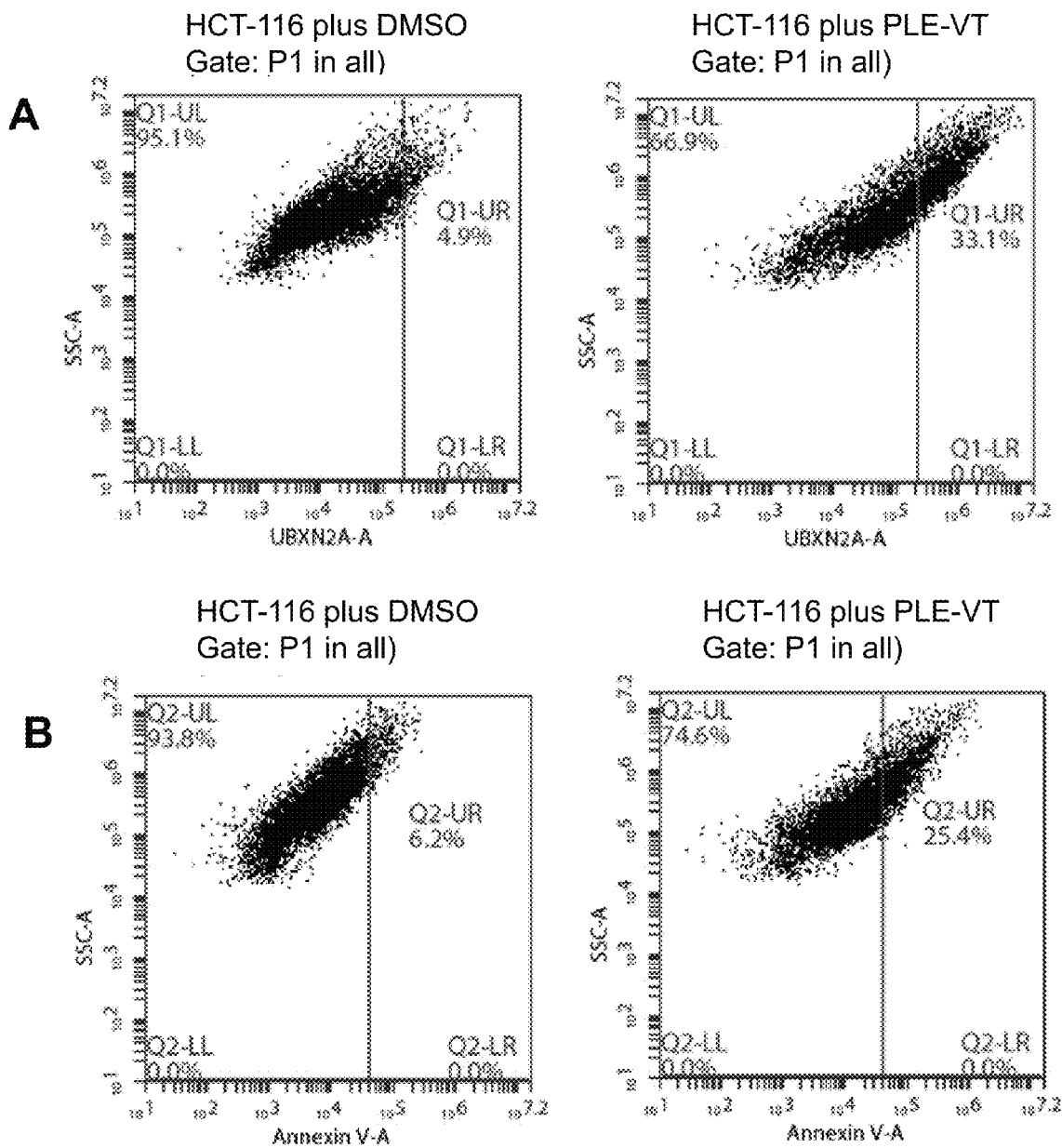
FIG. 21 shows flow-cytometry analysis of HCT-116 cells treated with Veratridine (VTD) conjugated on polymer PLE200.
Figure 21:
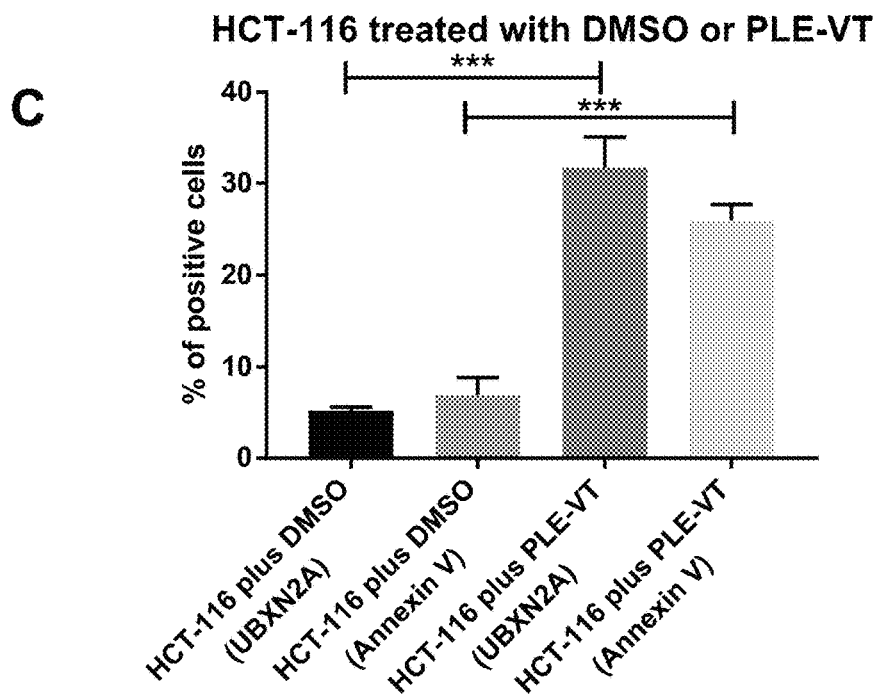
Figure 21:
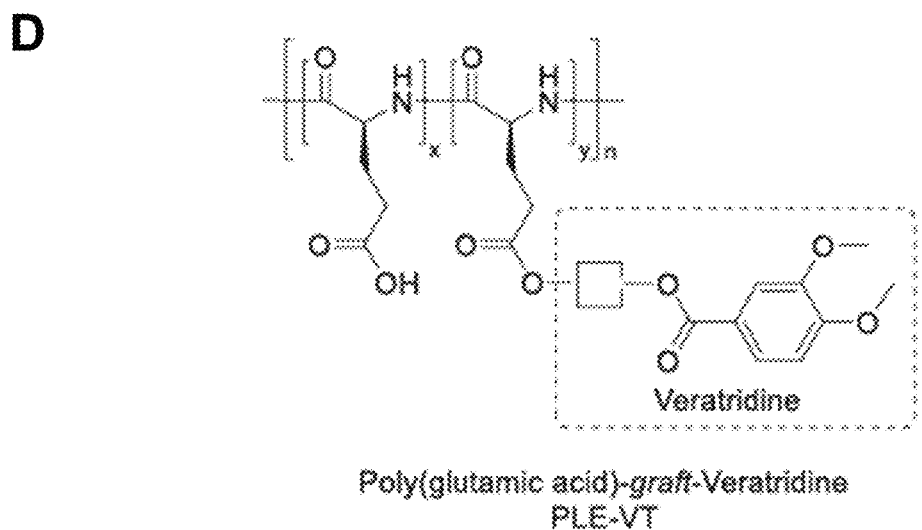
Figure 22:
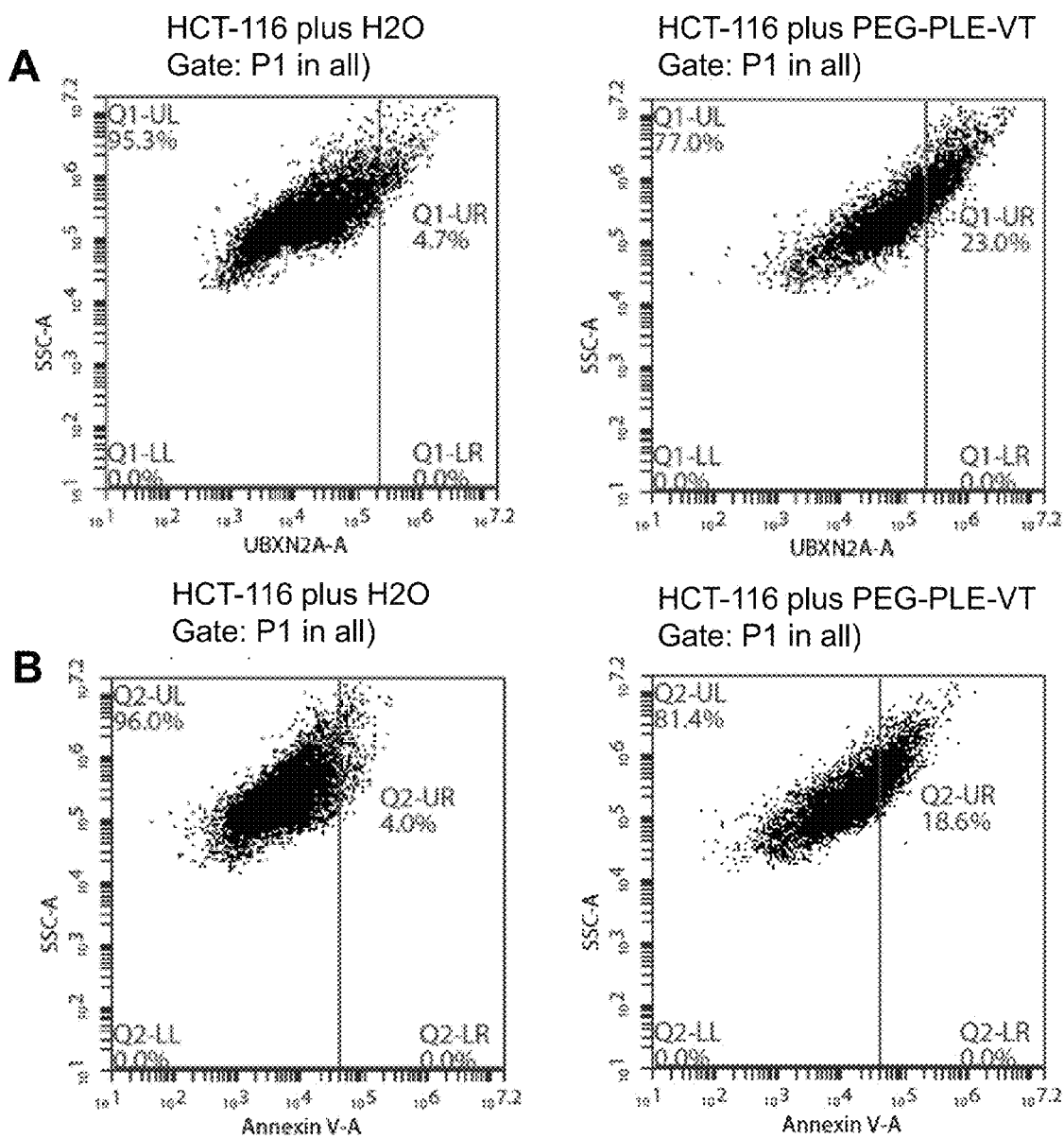
FIG. 22 shows flow-cytometry analysis of HCT-116 cells treated with Veratridine (VTD) conjugated on polymer PEG5k-b-PLE150.
Figure 22:
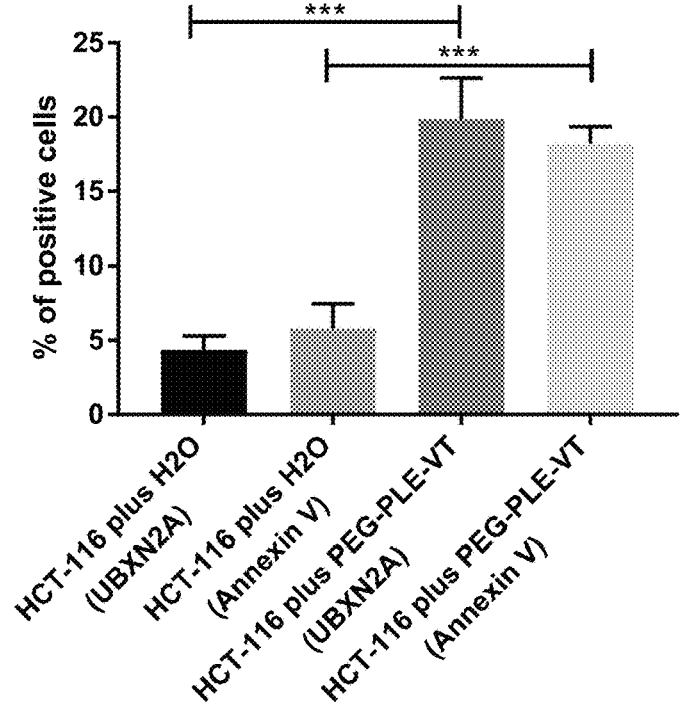
Figure 22:
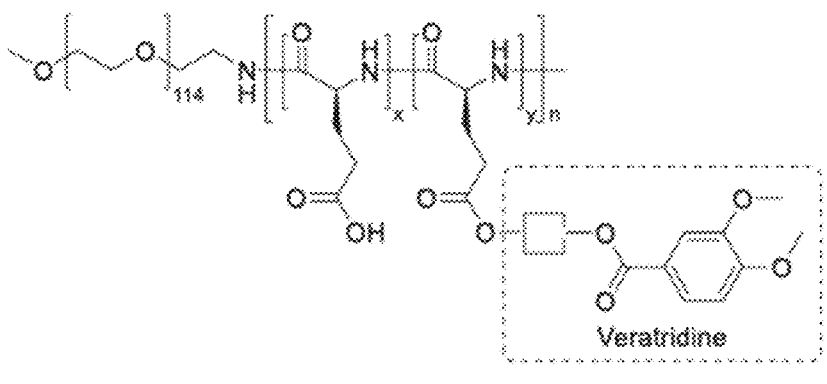

FIGS. 21 and 22 shows flow-cytometry analysis of HCT-116 cells treated with Veratridine (VTD) conjugated on polymer PLE200 (FIG. 21D) and PEG5k-b-PLE150 (FIG. 22D). HCT-116 colon cancer cell line were treated with 20 mM of two modified VTD (PLE-VT and PEG-PLE-VT) for 48 hours. Cells were collected followed by fixation, and then they were stained with anti-UBXN2A (secondary antibody the Alexa Fluor 546) and FITC Annexin V to be analyzed by BD Accuri C6 flow-cytometer (FIG. 21A-B and FIG. 22A-B). These data, as best shown in FIGS. 21C and 22C, indicate that this structural modification does not alter the biological activities of VTD toward UBXN2A and the Annexin V, apoptotic marker. Furthermore, the above modifications significantly decrease the Blood Brain Barrier (BBB) permeability to VTD.

Figure 23:
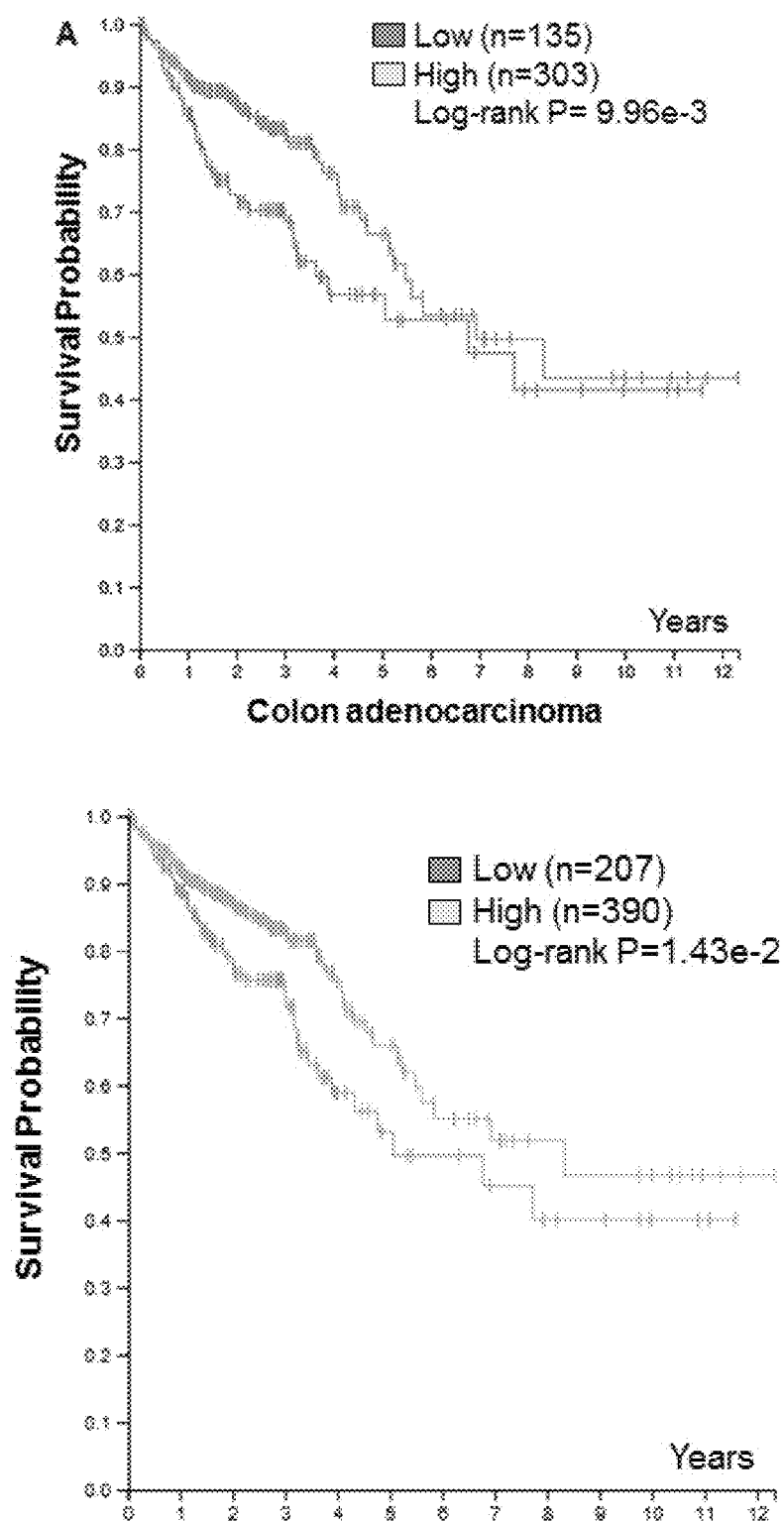
FIG. 23 shows graphs of the survival probably of human CRC with high and low UBXN2A expression.

FIG. 23 shows survival data from human cancer patients with high and low levels of UBXN2A expression. The data show that high level of UBXN2A can significantly improve survival probability of patients with colorectal cancer (colon adenocarcinoma and Colorectal cancer) in comparison to patients with low level of UBXN2A expression.

The cargo (VTD) is sealed inside the nanoparticles by the MMP-7 substrate or casein ("gate keeping" element), which keeps the cargo from fast release after injection as shown by preliminary data shown in FIGS. 24-30. The MMP-7 present in the cancerous tissue, but not in the normal tissue, will digest ("enzyme cleavage") the "gate keeping" element and release the cargo.

Figure 24:
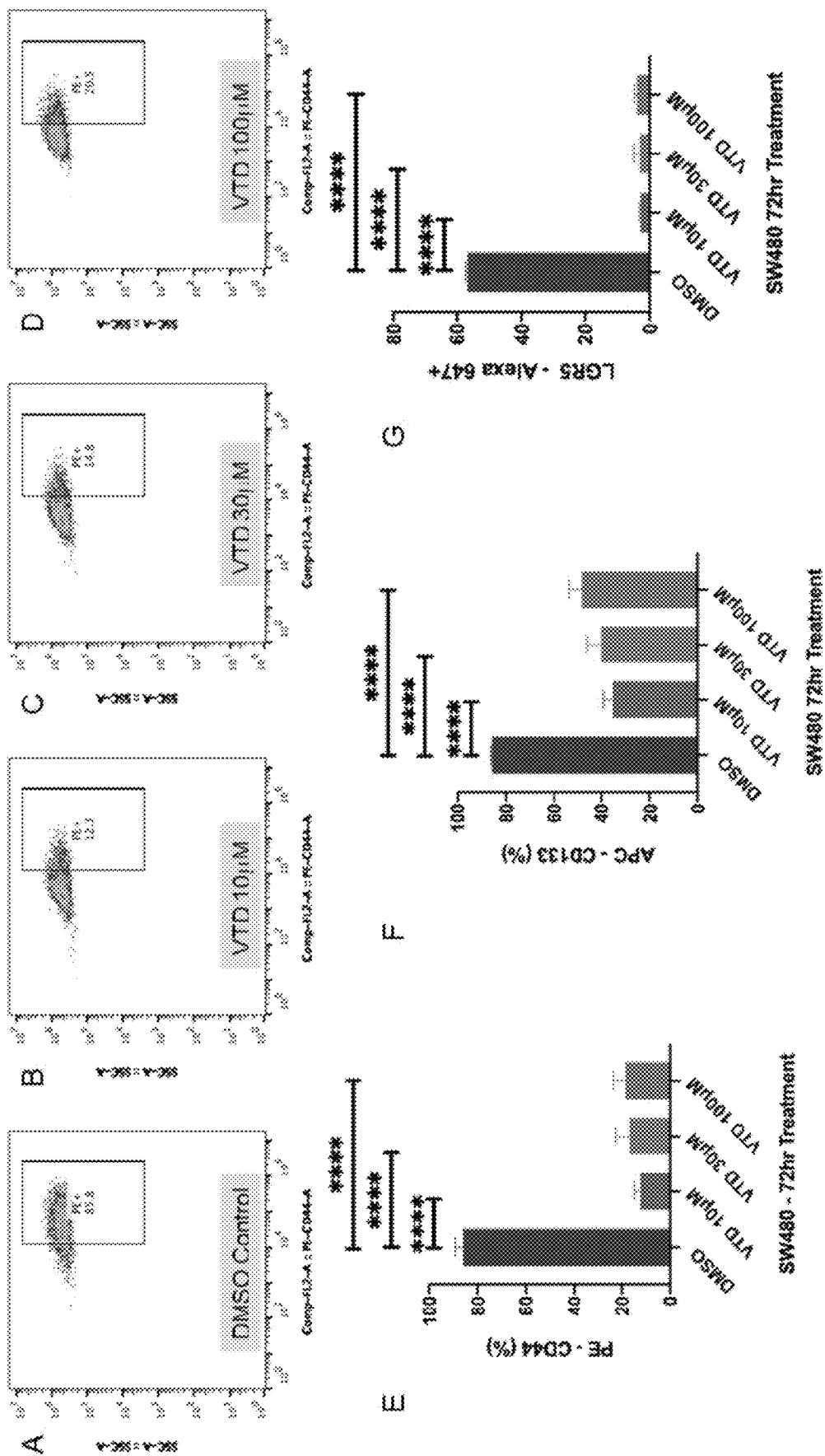
FIG. 24 shows data of the effect of VTD on stem cell populations in SW480 colon cancer cell lines.

VTD has been shown to target colon cancer stem cells, shown in FIG. 24. More specifically, VTD has been shown to reduce CD44+, CD133+ and LgR5+ stem cell populations in SW480 colon cancer cell line. FIG. 24 panels A-D are examples of FlowJo analysis of CD44 biomarker in SW480 cells treated with VTD for 72 hours. FIG. 24 panels F-G show bar graphs showing significant reduction of all three stem cell markers in VTD treated cells.

Figure 25:
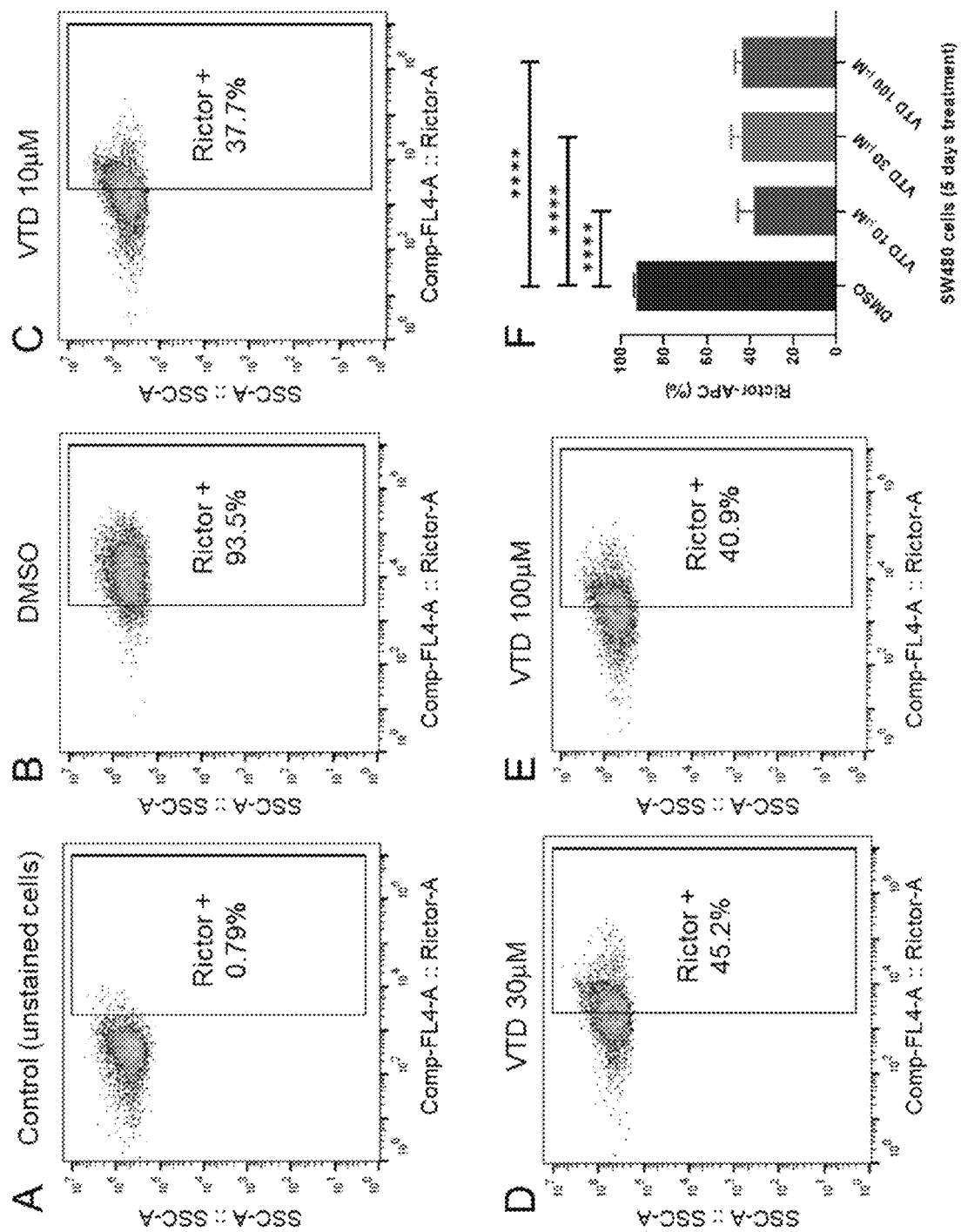
FIG. 25 shows data of the reduction of the level of Rictor proteins in SW480 metastatic colon cancer cells.

Further, VTD has been shown to significantly reduce the level of Rictor proteins in SW480 metastatic colon cancer cells, shown in FIG. 25. In panels A-E, SW480 cells were treated with VTD for 5 days (a semi-chronic treatment) and the cells were collected and subjected to flow-cytometry analysis using anti-Rictor antibody. Panel F of FIG. 25 shows that VTD significantly decreases Rictor proteins (N=3).

Figure 26:
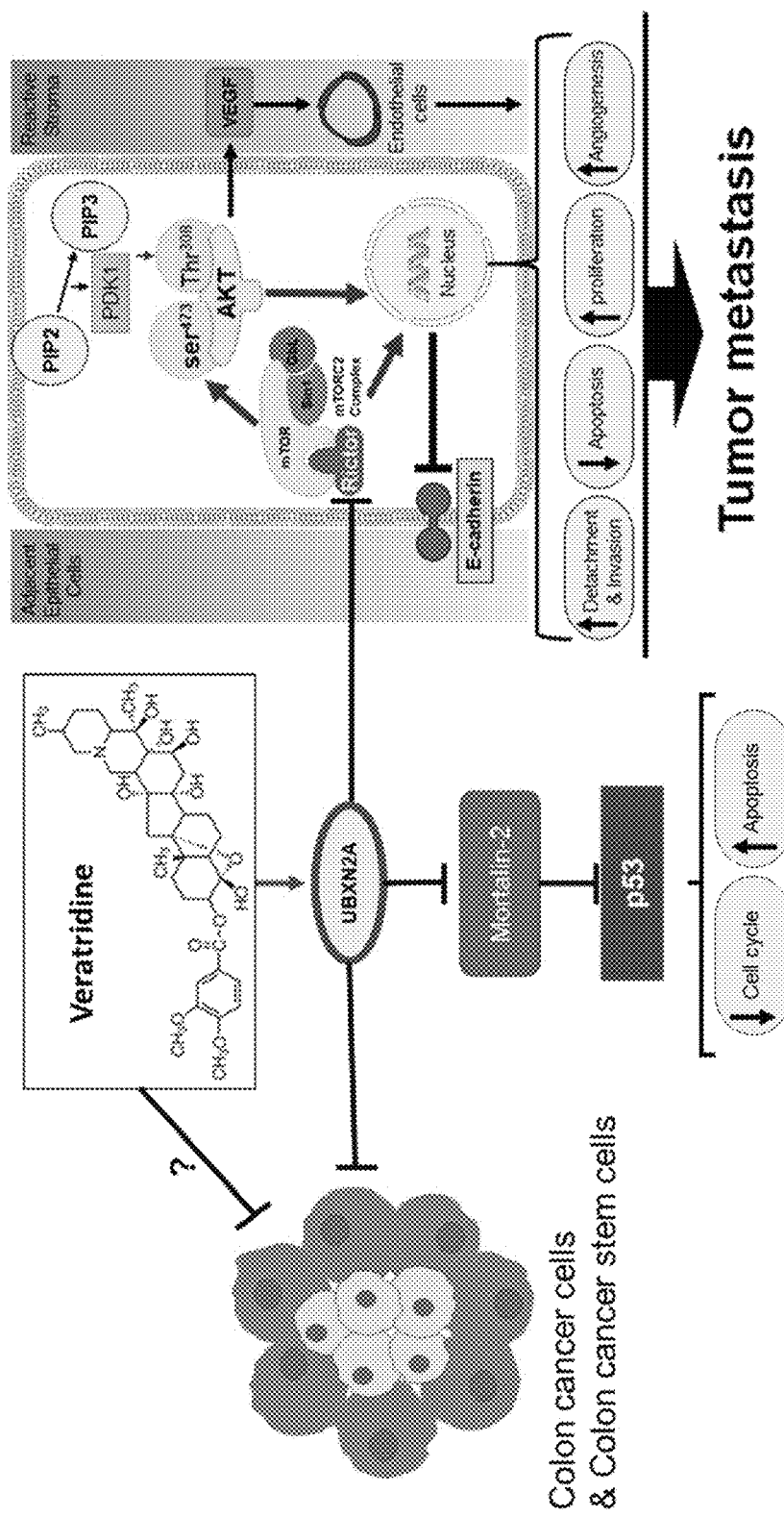
FIG. 26 shows veratridine-dependent upregulation of UBXN2A.

FIG. 26 shows VTD-dependent upregulation of UBXN2A, allows veratridine to target multiple tumorigenic pathways in cancer.

Figure 27:
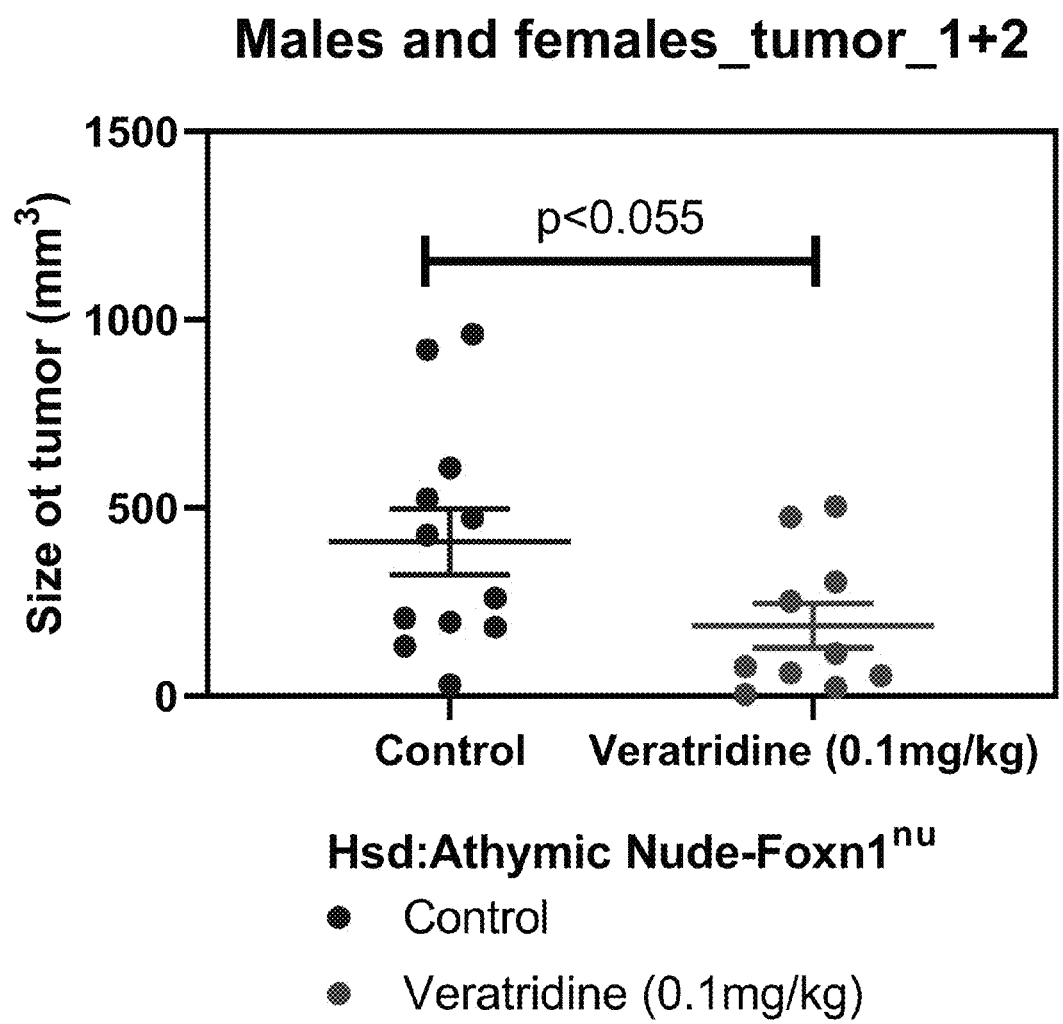
FIG. 27 shows data of the slowdown of growth of tumors in a xenograft mouse model.

FIG. 27 is an exemplary graph showing VTD slowdown growth of tumor in xenograft mouse model. Five week Hsd:Athymic Nude-Foxn1$^{nu}$ mice were implanted with $1 \times 10^6$ HCT-116-iRFP cancer cells at both flanks followed by IP injection of Ethanol (con) or Veratridine (VTD-0.1 mg/kg) every other day for 5 weeks. Twelve mice were used per treatment with 6 males and 6 females in each group.

Figure 28:
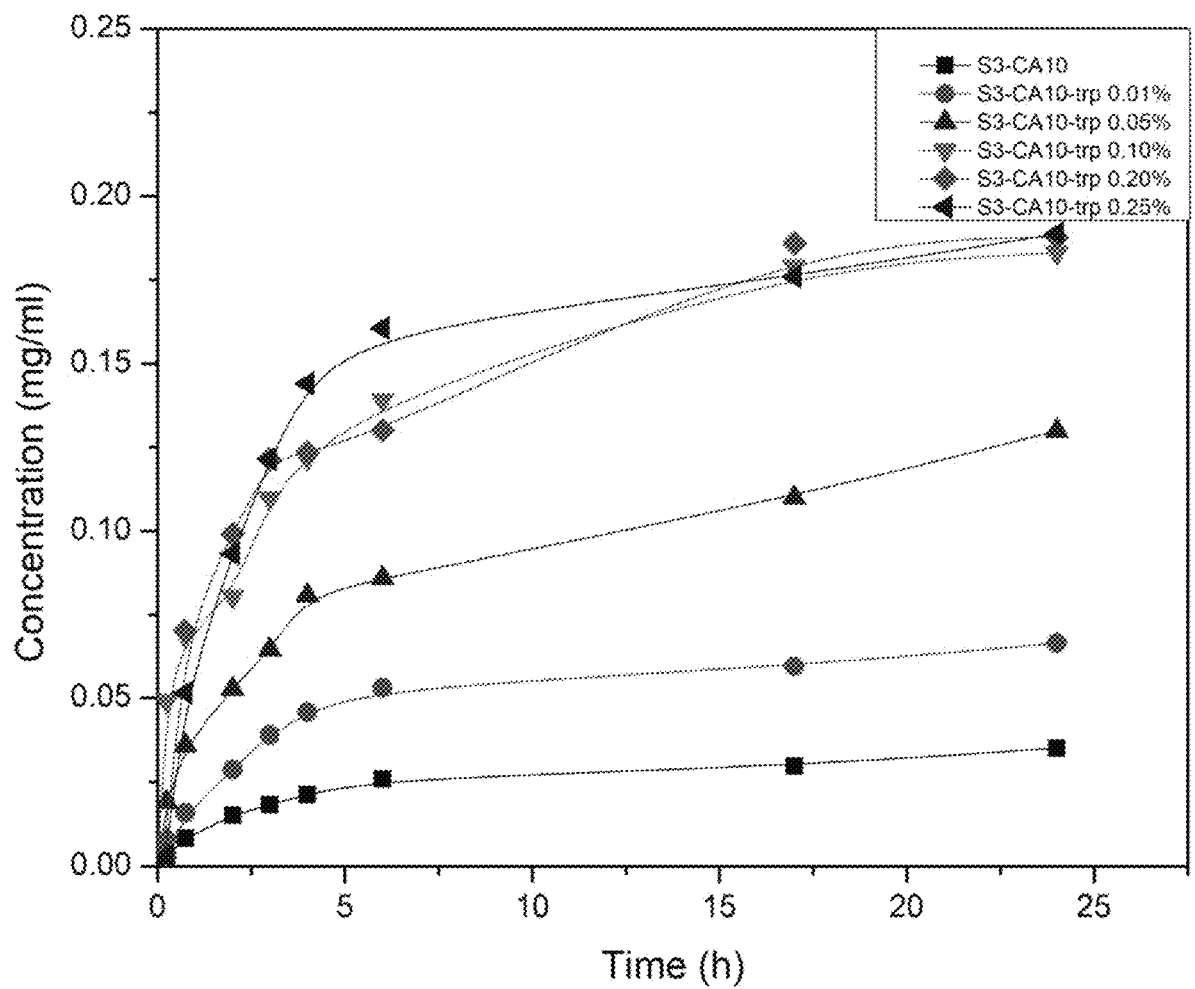
FIG. 28 shows the release of eugenol over time.

FIG. 28 shows Eugenol release from: S3-CA10-particles with covalently attached casein; S3-CA10-trp 0.01% -S3-CA10 particles treated with 0.01% trypsin; S3-CA10-trp 0.05% -S3-CA10 particles treated with 0.05% trypsin; 53-CA10-trp 0.10%-S3-CA10 particles treated with 0.01% trypsin; 53-CA10-trp 0.20%-S3-CA10 particles treated with 0.01% trypsin; and 53-CA10-trp 0.25%-S3-CA10 particles treated with 0.01% trypsin.

Figure 29:
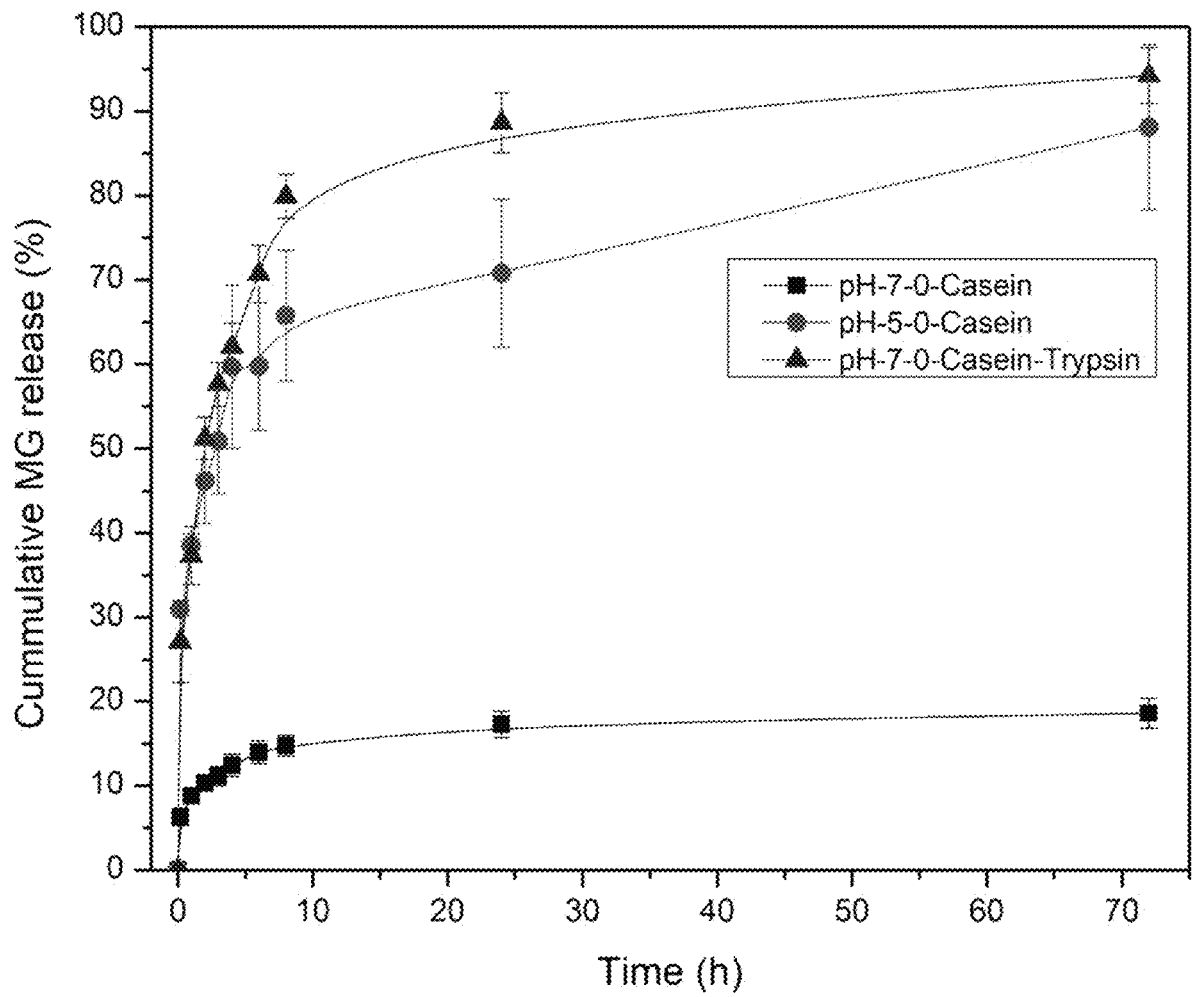
FIG. 29 shows the release of eugenol over time.

FIG. 29 shows Eugenol release from: Casein-coated hybrid silica-hydroxyapatite nanoparticles at pH=7; Casein-coated hybrid silica-hydroxyapatite nanoparticles at pH=5; and Casein-coated hybrid silica-hydroxyapatite nanoparticles at pH=7 in the presence of Trypsin.

Figure 30:
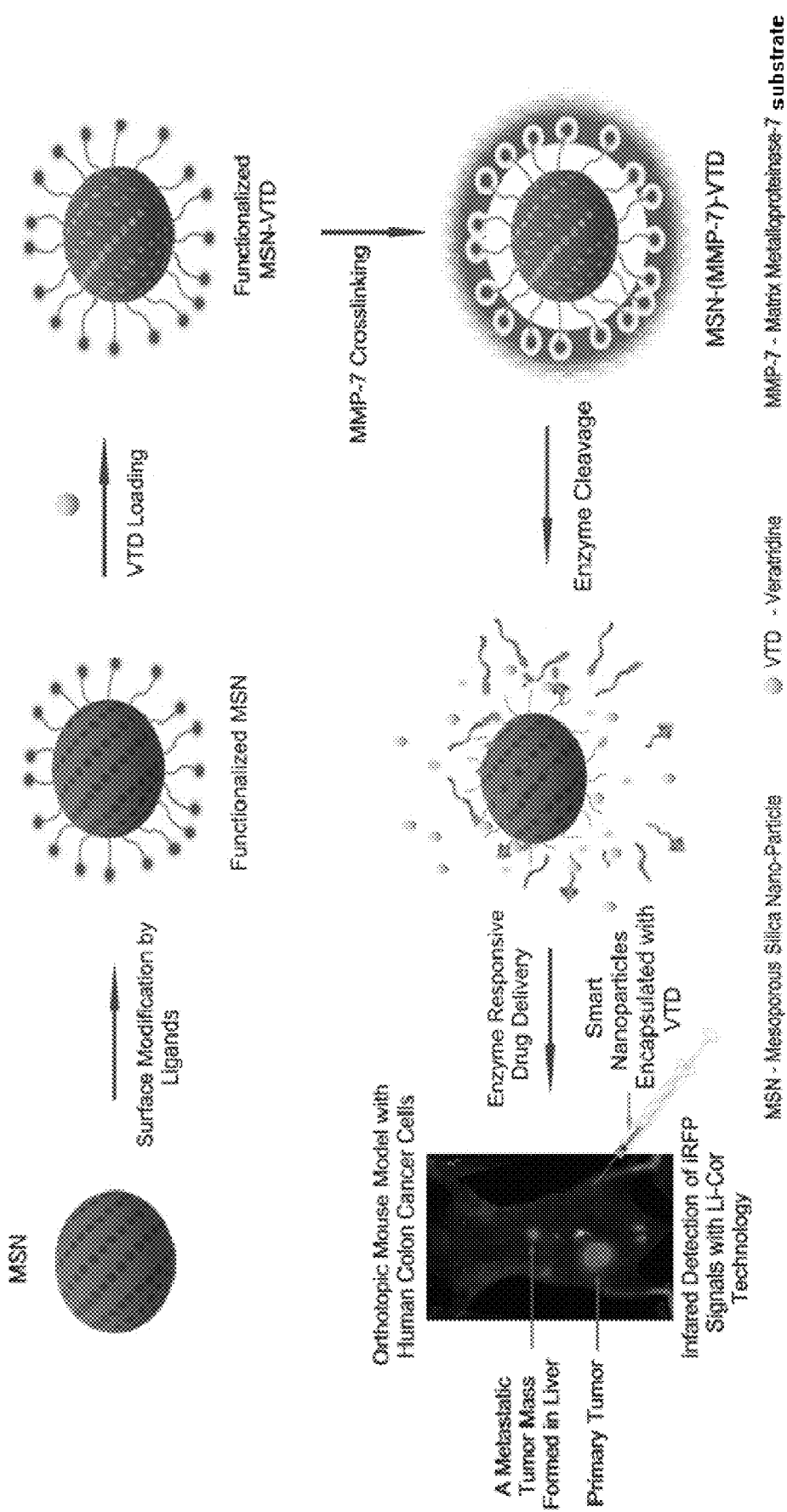
FIG. 30 is a schematic showing a nanotechnology delivery technique.

As shown in FIG. 30, the disclosed nanotechnology delivery technique will improve the stability and half-life of VTD in the circulation while enriching the concentration of PEG-VTD at the primary and secondary (liver and lung tissues) tumor sites.

Matrix metalloproteinases (MMPs) play an important role in the development and progression of CRC. MMP-1, -2, -3, -7, -9, -13, and MT1-MMP over expresses in human colorectal cancers. Expression levels of MMP-1, -2, -7, -9 and -13 are associated with poor prognosis in CRC patients while MMP-12 expression offers a protective role in CRC. Table 2 shows various matrix metalloproteases, where they are produced, and features thereof.

TABLE 2

Matrix metalloproteases and colorectal cancer

| Matrix metalloproteases | Produced by Tissues | Features |
| --- | --- | --- |
| MMP-7 | Exclusively by colorectal cancer cells | Abundantly expresses |
| MMP-3 | colorectal cancer | Microsatelite instability and poor prognosis |
| MMP-9 | primarily by inflammatory cells | early in the transition from colon adenoma to adenocarcinoma |
| MMP-12 | By the stromal cells surrounding a tumor or by the colorectal cancer cells themselves? | Inhibitory effect on angiogenesis and increases survival |
| MMP-1 (Collagenases) | Cancer cells | MMP-1 plays a role in initial stages of invasion |
| MMP-13 (Collagenases) | Cancer cells | Advanced cancer stage |
| MMP-2 (Gelatinases) | Cancer cells | Invasive CRC |
| MMP-9 (Gelatinases) | Cancer cells | MMP-9 is highly expressed in inflamed intestine |
| MMP-7 (Matrilysin) | Cancer cells | In ~80% of CRC. Advanced CRC and correlate with cancer progression |
| MMP-12 (Metalloelastase) | Cancer cells | MMP-12 is protective in CRC |

Although the present invention has been described with reference to preferred embodiments, persons skilled in the art will recognize that changes may be made in form and detail without departing from the spirit and scope of the invention.

What is claimed is:

1. A method of treating cancer in a subject, comprising: administering to the subject in need thereof, a composition comprising a veratridine (VTD) conjugate comprising a polyglutamic acid-VTD (PLE-VTD) conjugate or a polyethylene/polyglutamic acid-VTD (PEG-PLE-VTD) conjugate.

2. The method of claim 1, wherein the cancer is characterized by elevated mortalin-2 levels.

3. The method of claim 1, wherein the cancer comprises osteosarcoma or breast cancer.

4. The method of claim 1, wherein the composition has reduced neurotoxicity relative to a comparable dose of unmodified veratridine.

5. The method of claim 1, further comprising administering the composition in conjunction with at least one other treatment or therapy.

6. The method of claim 1, wherein the composition increases UBXN2A protein levels.

7. The method of claim 1, wherein the composition reduces the formation of electrophilic ortho-quinones in catechol metabolites the composition has reduced neurotoxicity relative to comparable dose of unmodified VTD.

8. The method of claim 1, wherein the composition suppresses the mTORC2 pathway.

9. The method of claim 1, wherein the subject has been shown to be resistant to one or more chemotherapy.

10. The method of claim 1, wherein the composition further comprises a pharmaceutically acceptable carrier.

11. The method of claim 10, wherein the pharmaceutically acceptable carrier comprises a mesoporous silica nanoparticle.

12. The method of claim 1, wherein the composition is administered intravenously, intraperitoneally, intramuscularly, subcutaneously, or transdermally.

13. A method of preventing cancer in a subject, comprising: administering to the subject in need thereof, a composition comprising a veratridine (VTD) conjugate comprising a polyglutamic acid-VTD (PLE-VTD) conjugate or a polyethylene/polyglutamic acid-VTD (PEG-PLE-VTD) conjugate.

14. The method of claim 13, wherein the cancer is characterized by elevated mortalin-2 levels.

15. The method of claim 13, wherein the cancer comprises osteosarcoma or breast cancer.

16. The method of claim 13, wherein the subject has a high risk of developing a cancer characterized by elevated mortalin-2 levels.

17. The method of claim 13, wherein the subject has a high risk of developing osteosarcoma or breast cancer.

18. The method of claim 13, further comprising administering the composition in conjunction with at least one other treatment or therapy.

19. The method of claim 13, wherein the composition increases UBXN2A protein levels.

20. The method of claim 13, wherein the composition is administered intravenously, intraperitoneally, intramuscularly, subcutaneously, or transdermally.

* * * * *